US009636143B2

(12) United States Patent
Weisbrod et al.

(10) Patent No.: US 9,636,143 B2
(45) Date of Patent: May 2, 2017

(54) TROCAR AND WOUND CLOSURE DEVICE

(71) Applicant: Gordian Surgical Ltd., Misgav (IL)

(72) Inventors: Hagay Weisbrod, Kibbutz Kinneret (IL); Oded Elish, Kiryat-Tivon (IL)

(73) Assignee: Gordian Surgical Ltd., Misgav (IL)

( * ) Notice: Subject to any disclaimer, the term of this patent is extended or adjusted under 35 U.S.C. 154(b) by 0 days.

(21) Appl. No.: 14/686,823

(22) Filed: Apr. 15, 2015

(65) Prior Publication Data
US 2015/0216514 A1 Aug. 6, 2015

Related U.S. Application Data

(63) Continuation of application No. PCT/IL2014/050833, filed on Sep. 17, 2014.
(Continued)

(51) Int. Cl.
*A61B 17/10* (2006.01)
*A61B 17/34* (2006.01)
(Continued)

(52) U.S. Cl.
CPC ...... *A61B 17/3423* (2013.01); *A61B 17/0057* (2013.01); *A61B 17/0218* (2013.01);
(Continued)

(58) Field of Classification Search
CPC . A61B 17/0469; A61B 17/3417; A61B 17/34; A61B 2017/348; A61B 2017/349
See application file for complete search history.

(56) References Cited

U.S. PATENT DOCUMENTS 5,417,699 A * 5/1995 Klein ................. A61B 17/0057
112/169
5,792,152 A * 8/1998 Klein ................. A61B 17/0057
606/139
(Continued)

FOREIGN PATENT DOCUMENTS

WO WO 2015/040617 3/2015

OTHER PUBLICATIONS

International Search Report and the Written Opinion Dated Dec. 29, 2014 From the International Searching Authority Re. Application No. PCT/IL2014/050833.
(Continued)

Primary Examiner — Ashley Fishback

(57) ABSTRACT

A trocar adapted for insertion through a fascia layer of an abdominal wall, comprising a proximal end configured for handling by a user; a distal end configured for insertion into tissue; and a shaft extending in between the proximal end and distal end, wherein the shaft comprises a narrow portion proximal to the distal end, the narrow portion defining at least one recess shaped and sized to receive fascia tissue, the recess ending, at a distal end, with a generally proximally facing surface of the shaft configured directly below the narrow portion, the proximally facing surface and the narrow portion shaped and sized to stabilize the trocar in the abdominal wall by the fascia. In some embodiments, a trocar and external cannula assembly are provided. In some embodiments, the trocar and/or trocar and external cannula assembly are configured for deployment of one or more anchors and/or sutures in the tissue.

117 Claims, 51 Drawing Sheets

Related U.S. Application Data

(60) Provisional application No. 61/878,660, filed on Sep. 17, 2013.

(51) Int. Cl.
  *A61B 17/04* (2006.01)
  *A61B 17/00* (2006.01)
  *A61B 17/02* (2006.01)

(52) U.S. Cl.
  CPC ...... *A61B 17/0401* (2013.01); *A61B 17/0469* (2013.01); *A61B 17/0482* (2013.01); *A61B 17/3417* (2013.01); *A61B 17/3421* (2013.01); *A61B 17/3468* (2013.01); *A61B 17/3478* (2013.01); *A61B 17/3462* (2013.01); *A61B 2017/00637* (2013.01); *A61B 2017/00663* (2013.01); *A61B 2017/047* (2013.01); *A61B 2017/0409* (2013.01); *A61B 2017/0417* (2013.01); *A61B 2017/0445* (2013.01); *A61B 2017/0464* (2013.01); *A61B 2017/0472* (2013.01); *A61B 2017/346* (2013.01); *A61B 2017/3454* (2013.01); *A61B 2017/3482* (2013.01); *A61B 2017/3484* (2013.01); *A61B 2017/3488* (2013.01)

(56) References Cited

U.S. PATENT DOCUMENTS

| | | |
|---|---|---|
| 5,810,848 A | 9/1998 | Hayhurst |
| 5,860,993 A | 1/1999 | Thompson et al. |
| 5,871,490 A | 2/1999 | Schulze et al. |
| 6,312,448 B1 | 11/2001 | Bonutti |
| 6,610,072 B1 | 8/2003 | Christy et al. |
| 6,972,027 B2 | 12/2005 | Fallin et al. |
| 7,390,329 B2 | 6/2008 | Westra et al. |
| 7,824,419 B2 | 11/2010 | Boraiah |
| 8,109,943 B2 | 2/2012 | Boraiah et al. |
| 2009/0281568 A1 | 11/2009 | Cendan et al. |
| 2010/0262166 A1 | 10/2010 | Boraiah et al. |
| 2011/0224495 A1 | 9/2011 | Carter et al. |
| 2012/0296374 A1* | 11/2012 | Ziobro ............ A61B 17/0057 606/214 |
| 2016/0000460 A1 | 1/2016 | Weisbrod et al. |

OTHER PUBLICATIONS

International Preliminary Report on Patentability Dated Mar. 31, 2016 From the International Bureau of WIPO Re. Application No. PCT/IL2014/050833.

\* cited by examiner

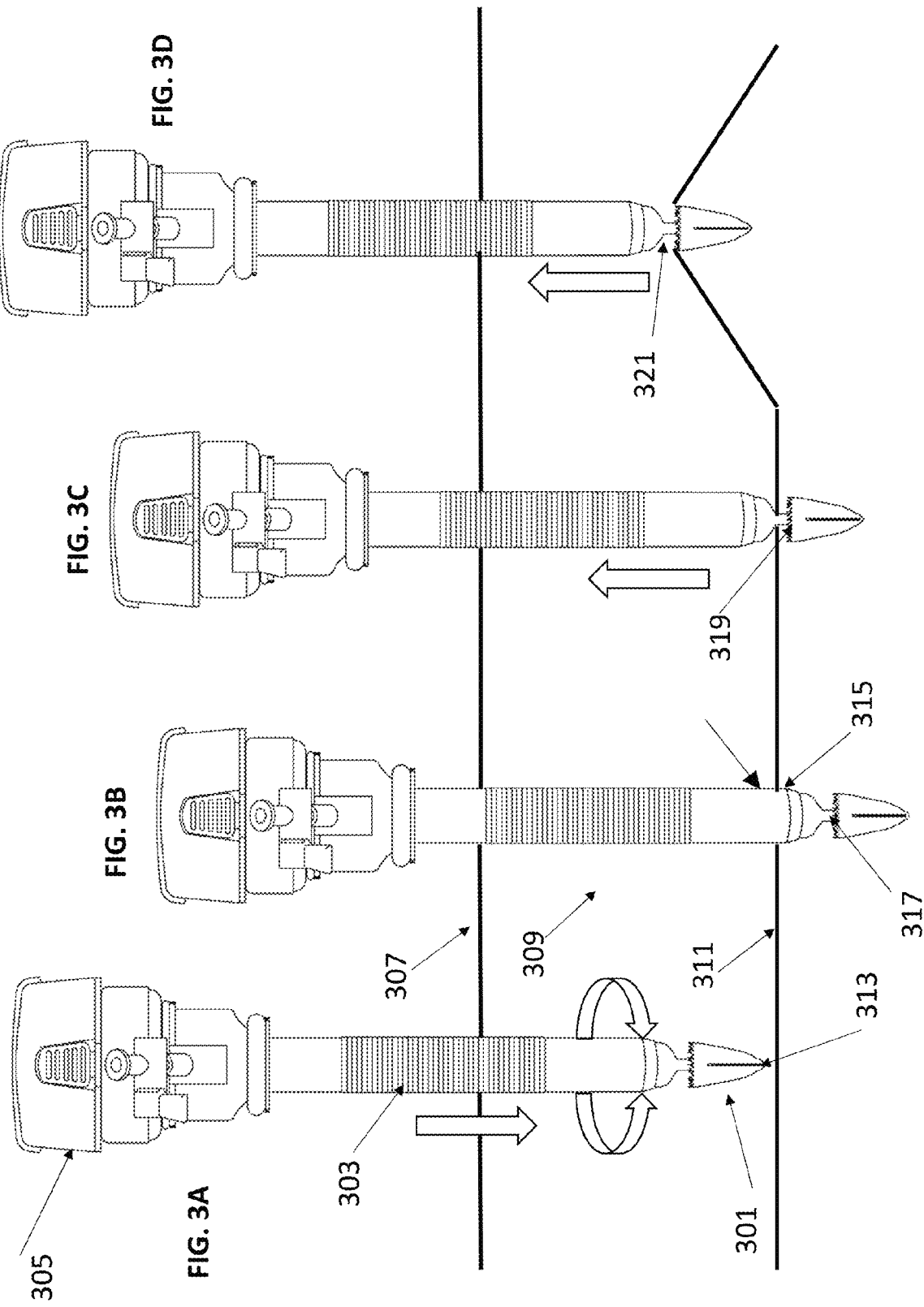

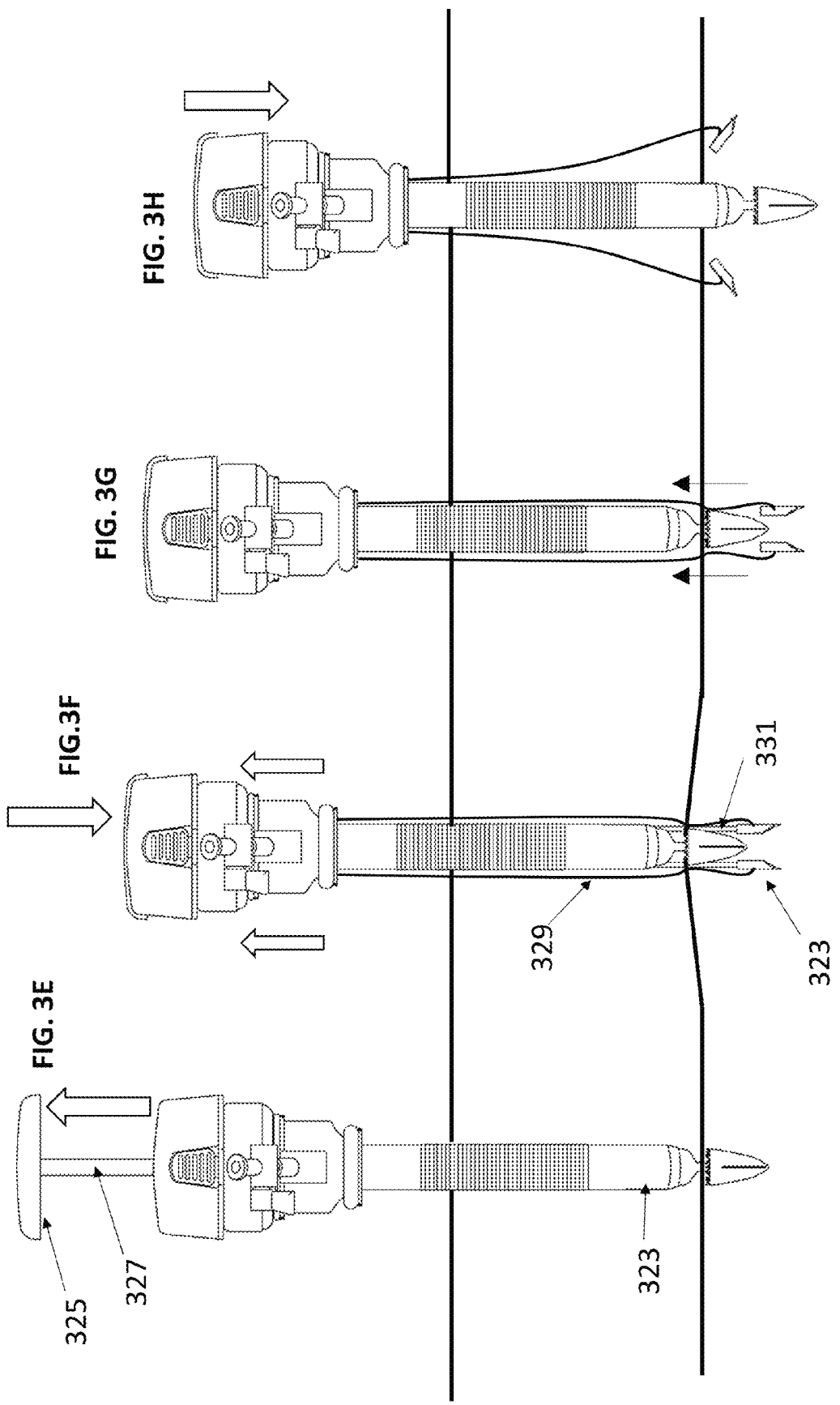

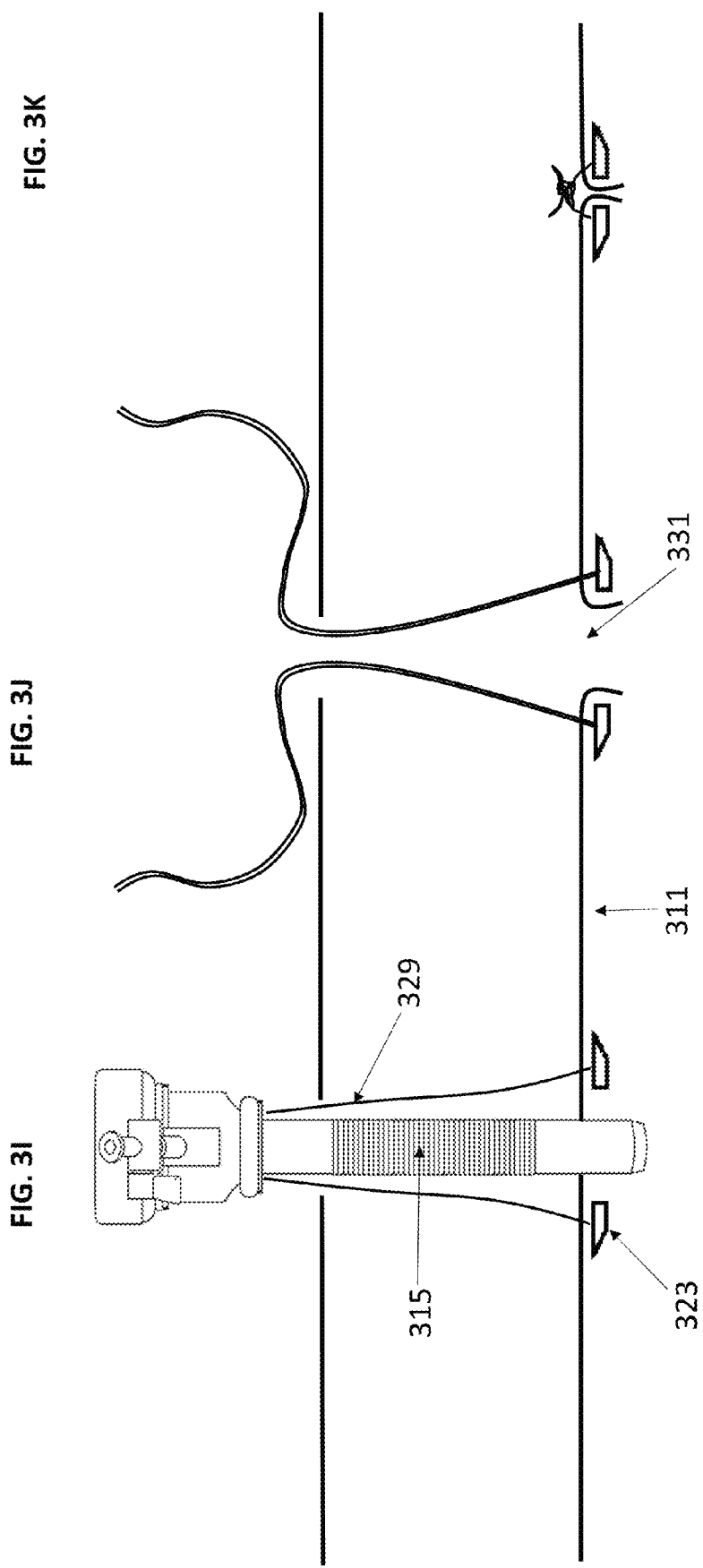

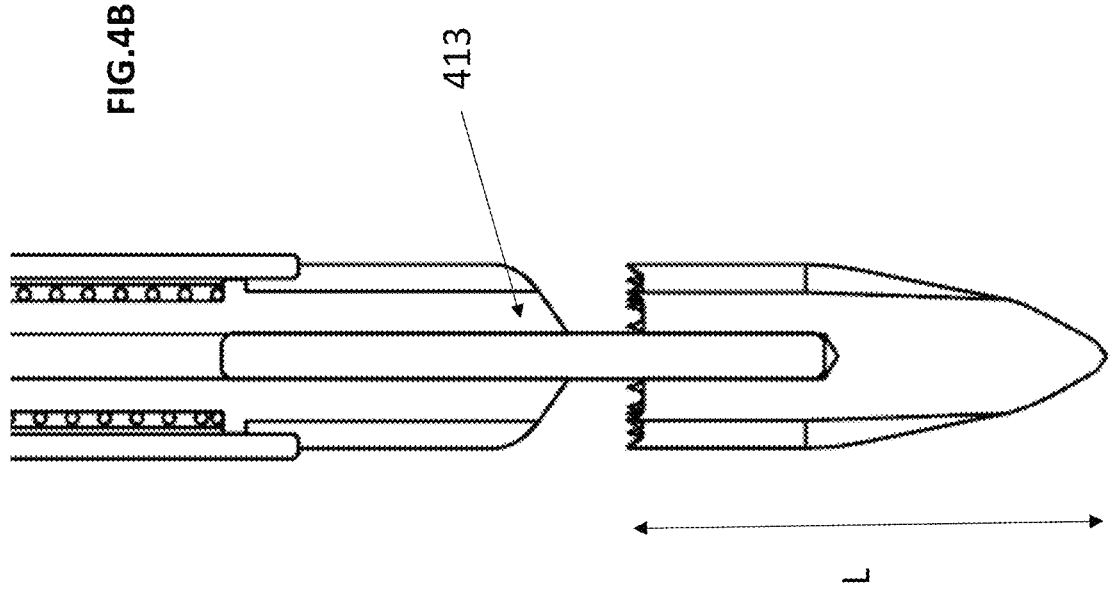

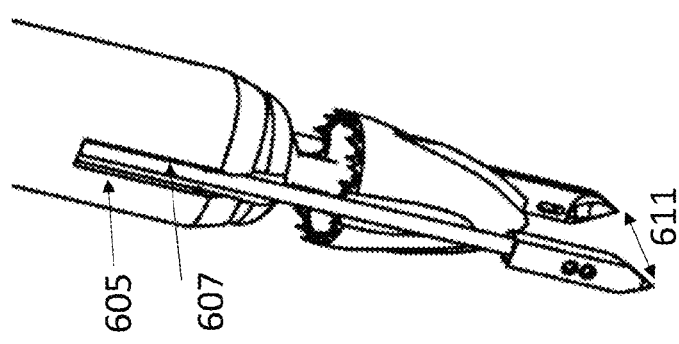
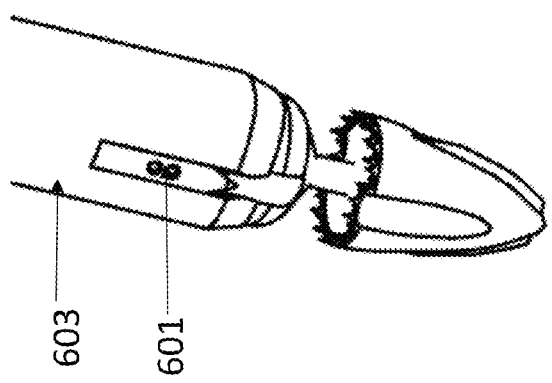
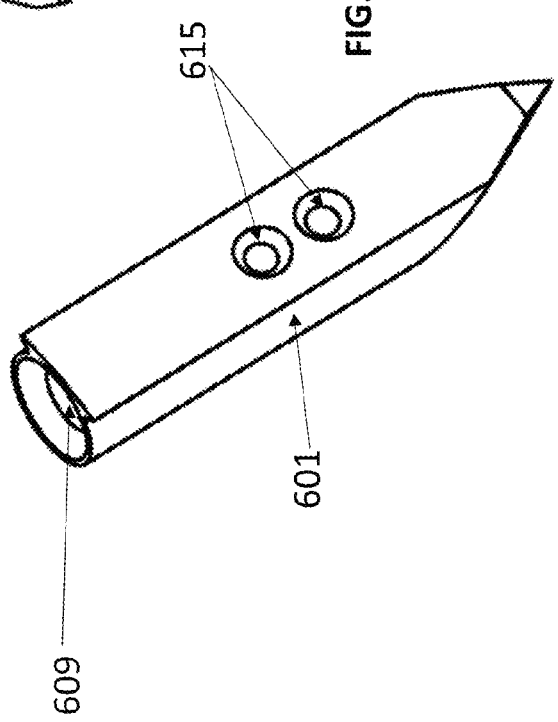

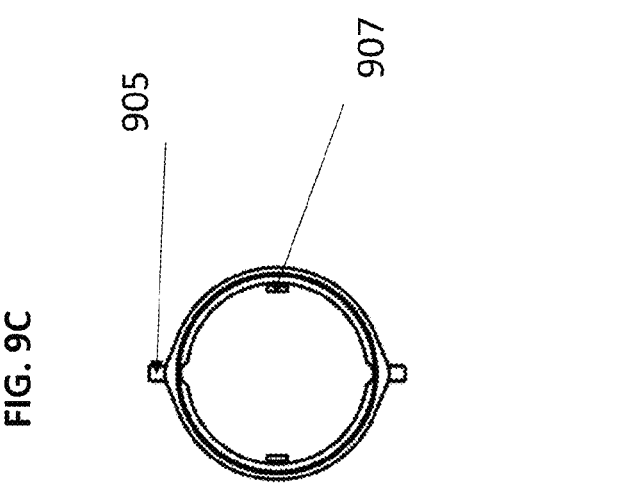
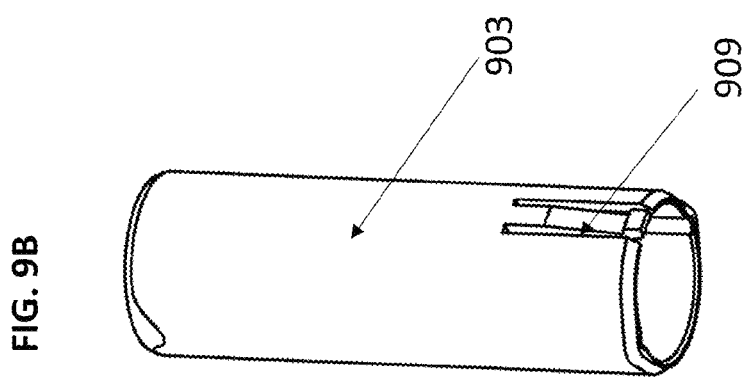
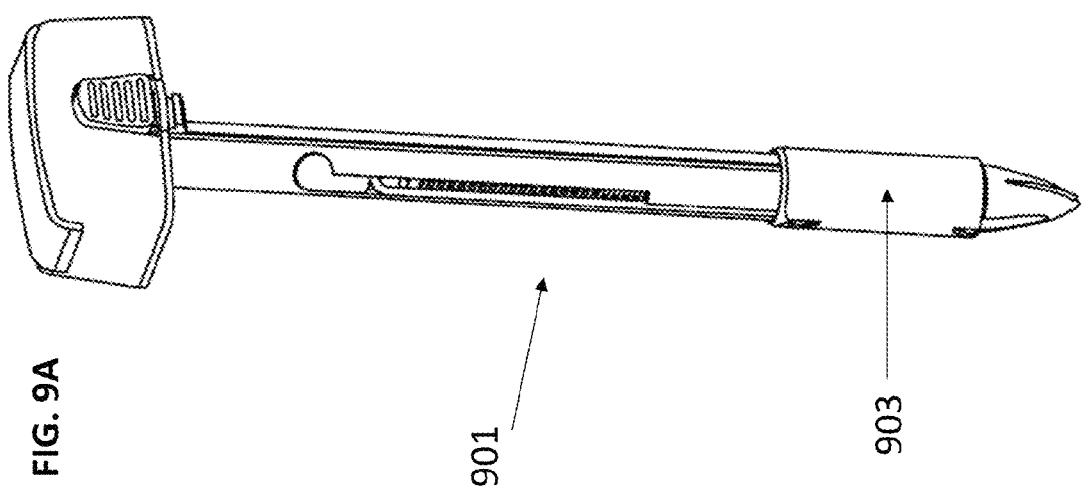

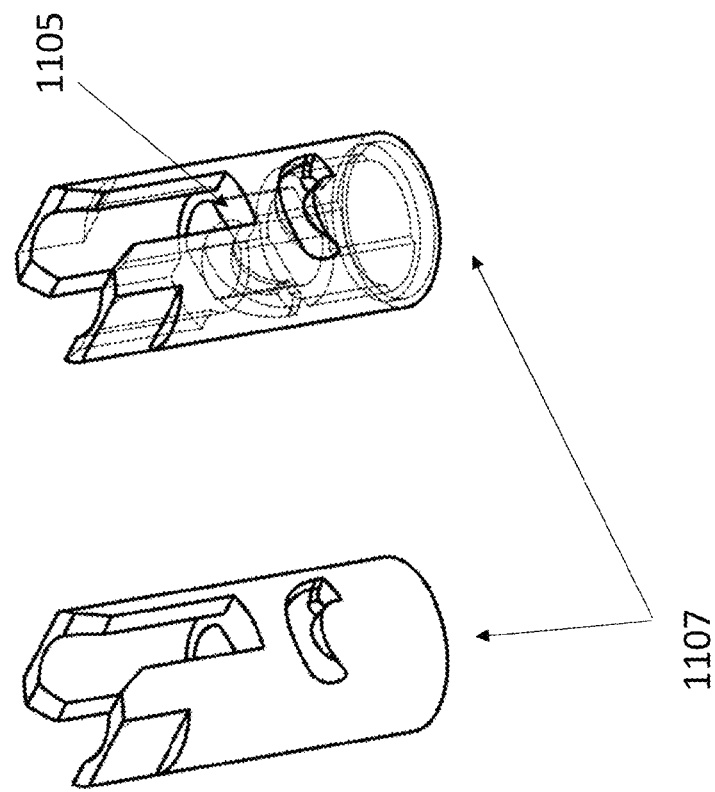
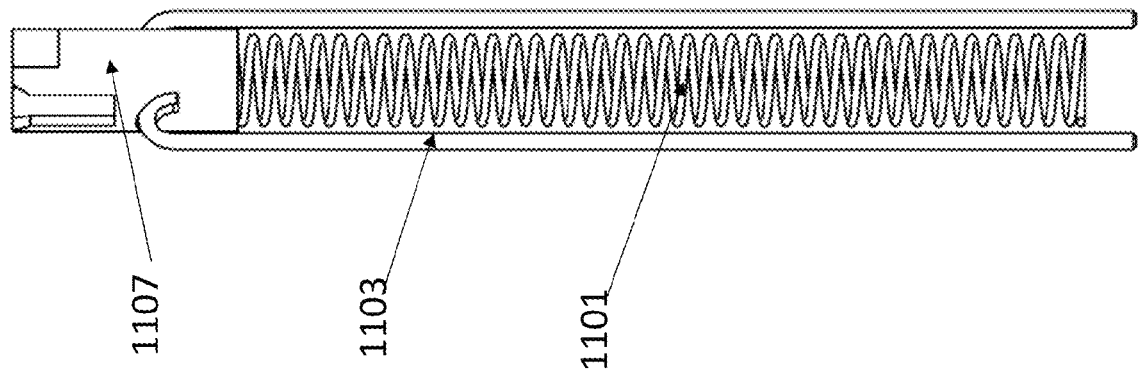

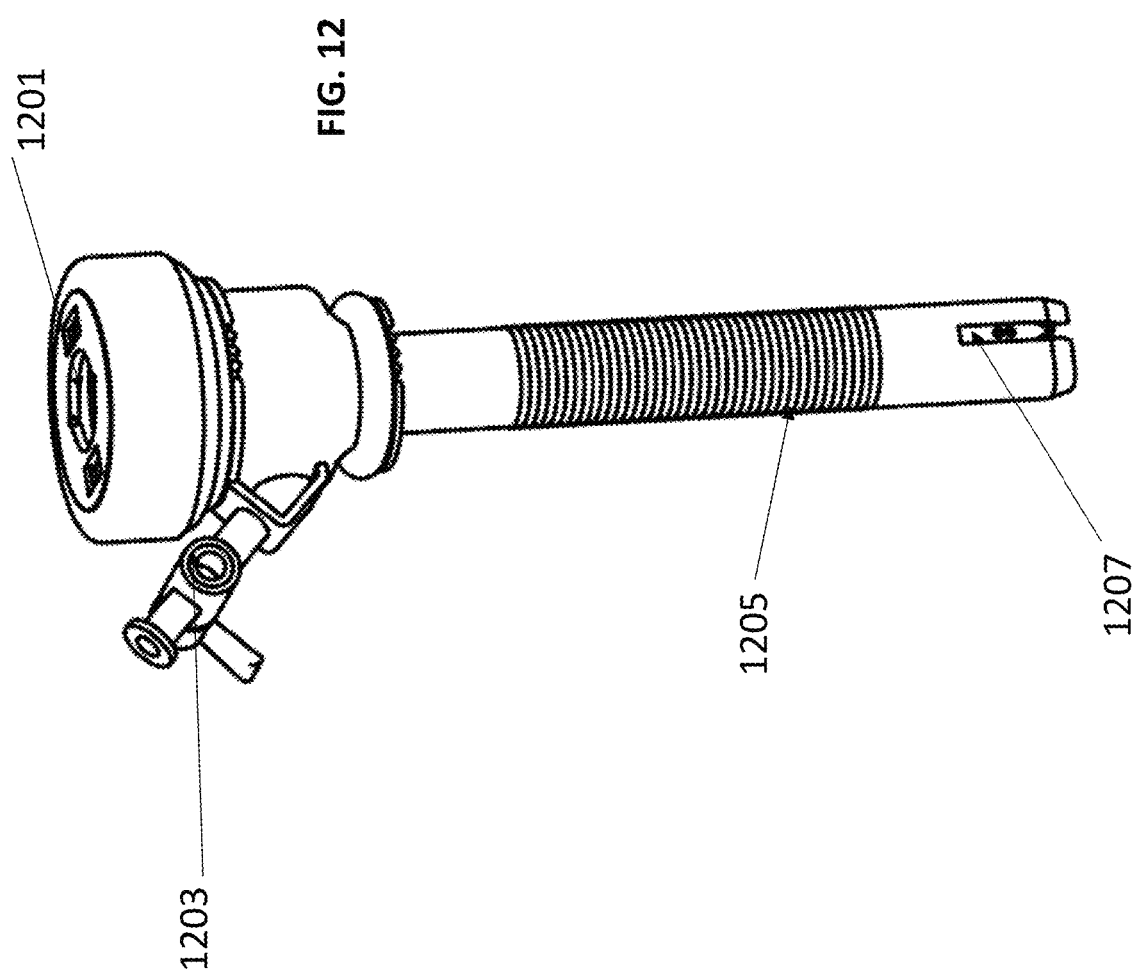

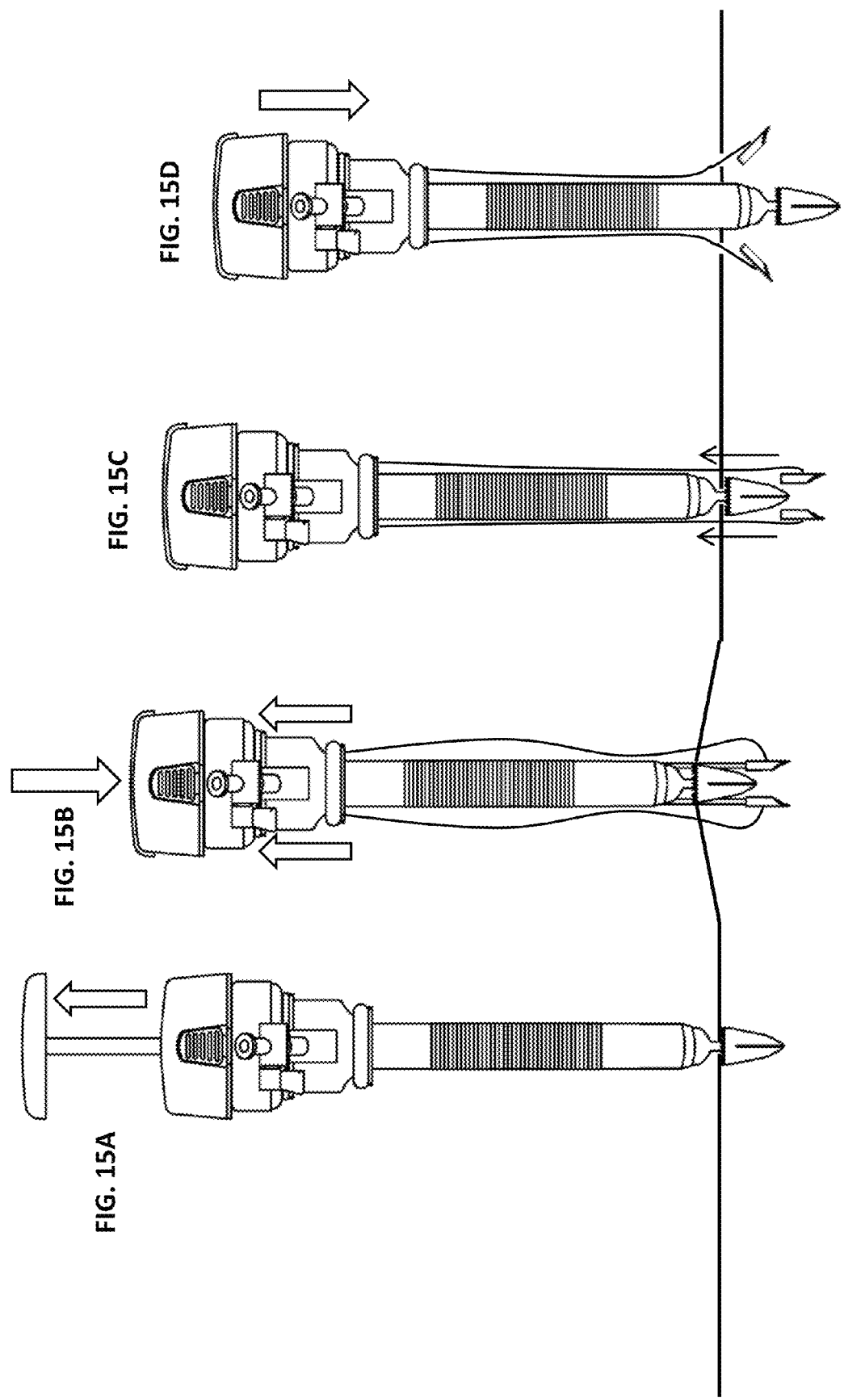

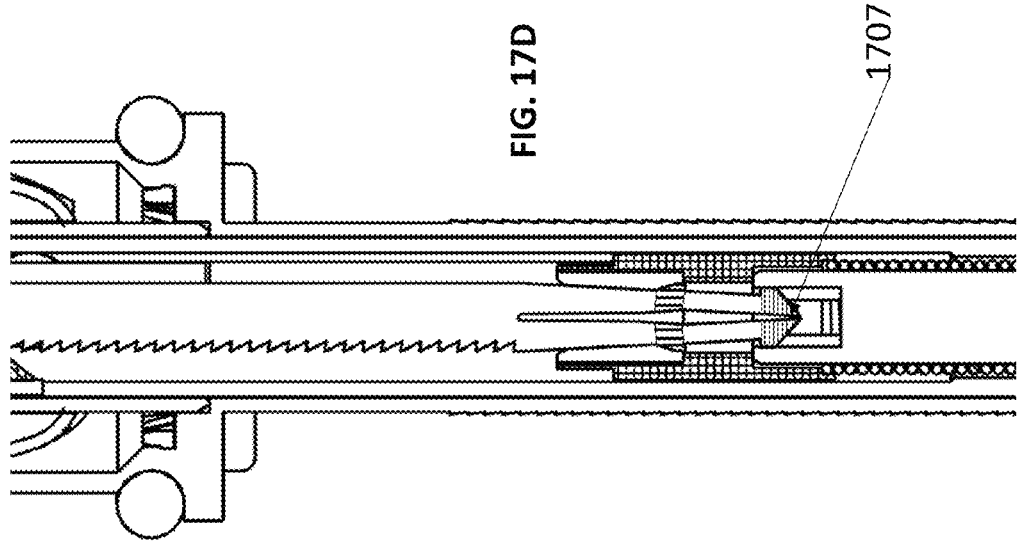
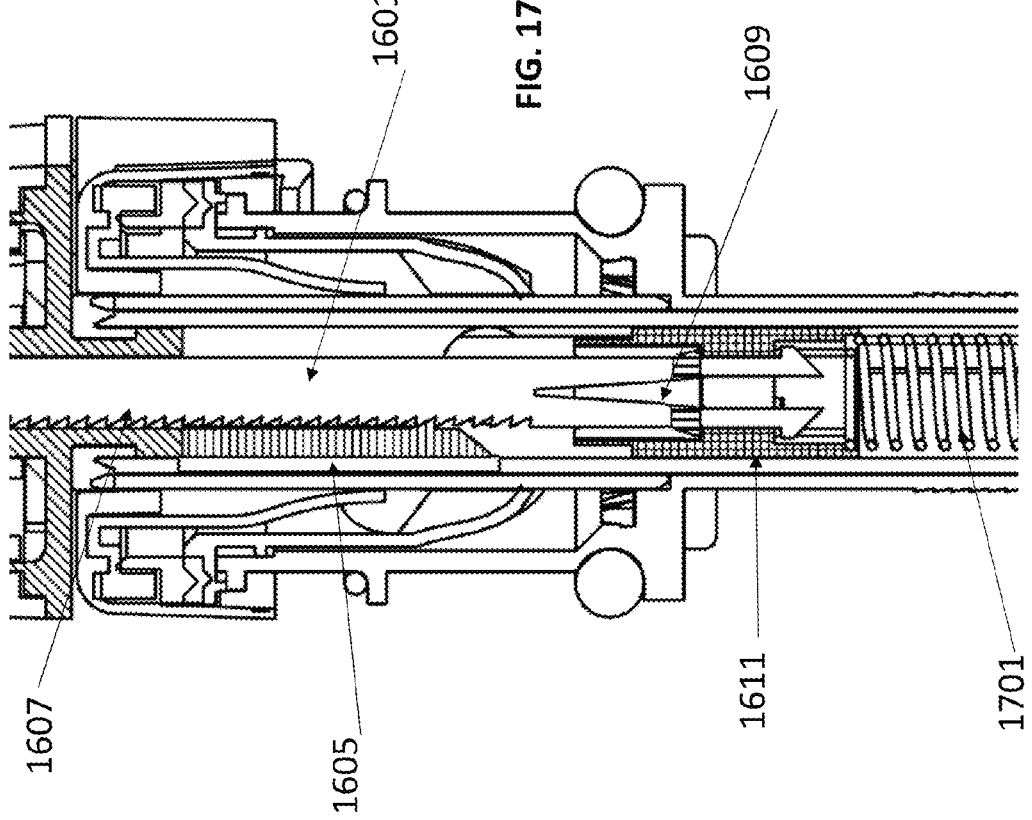

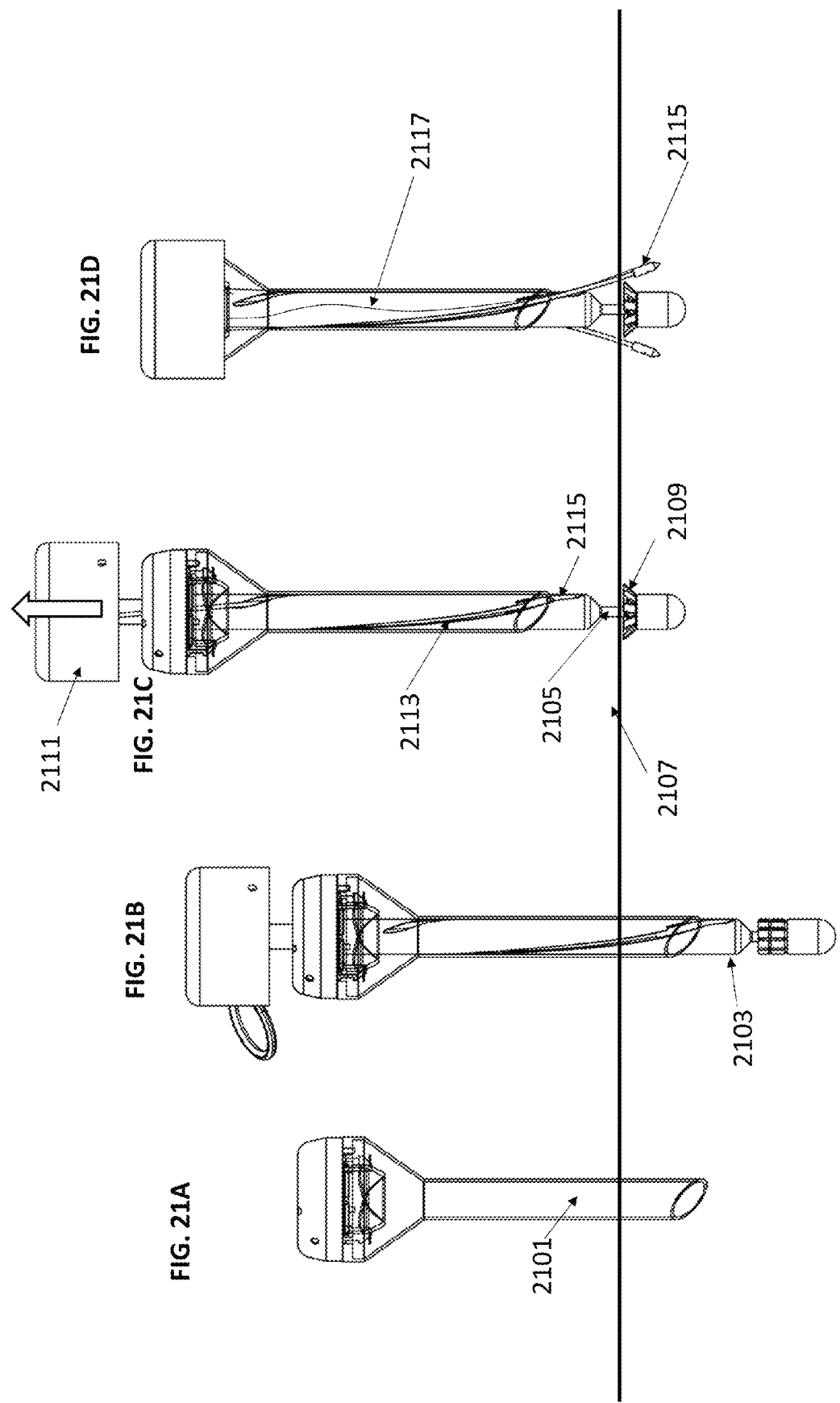

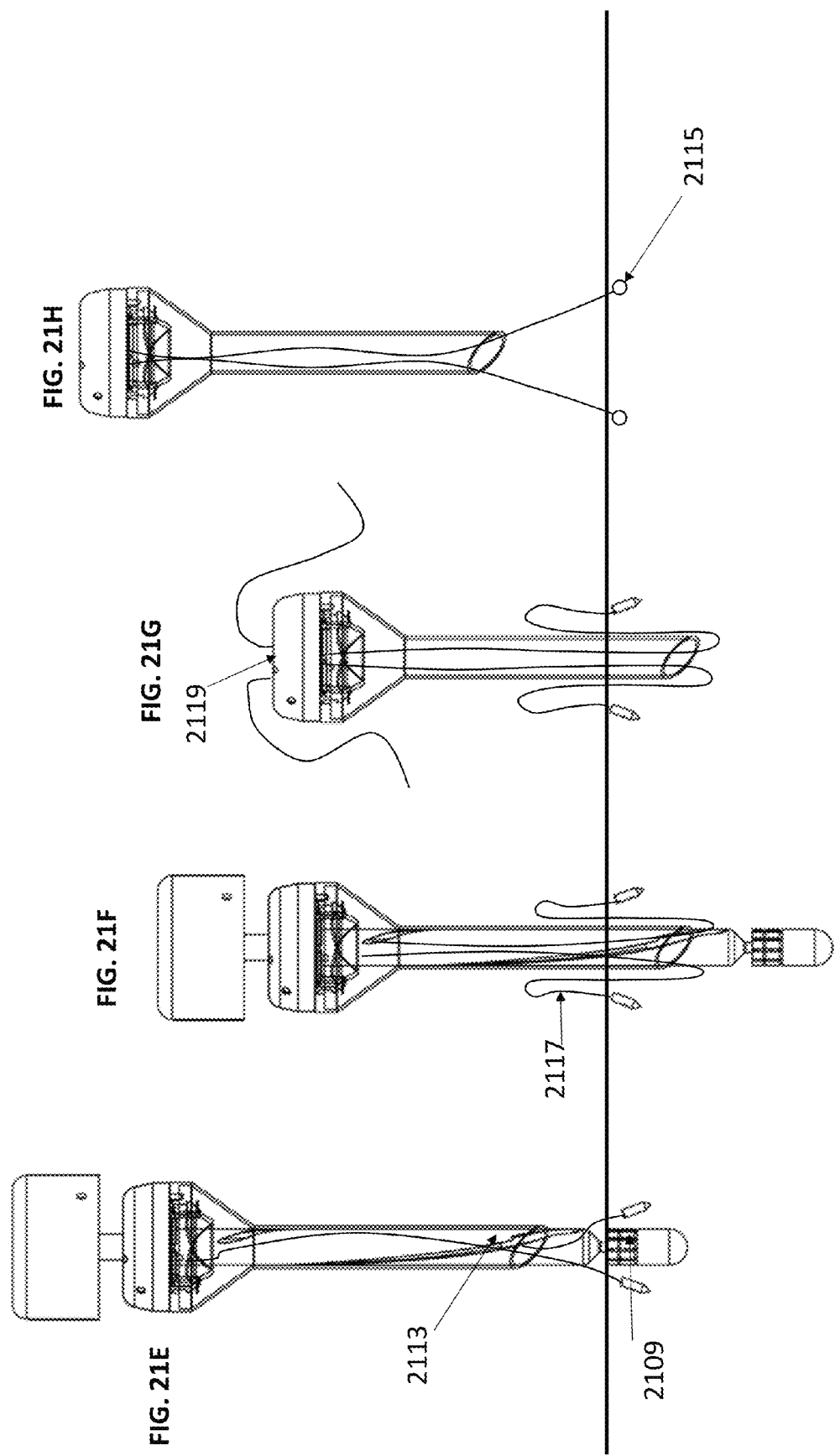

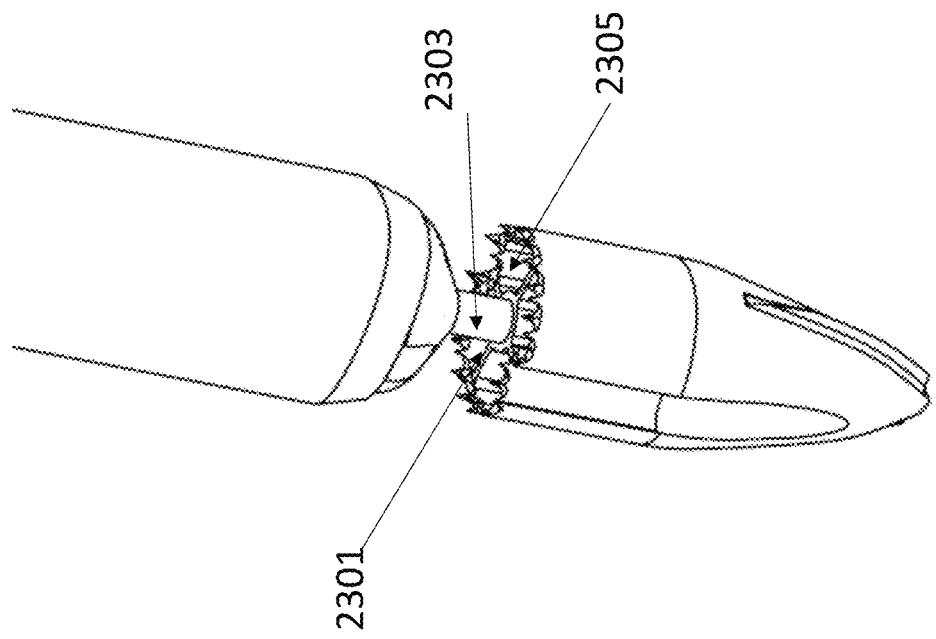

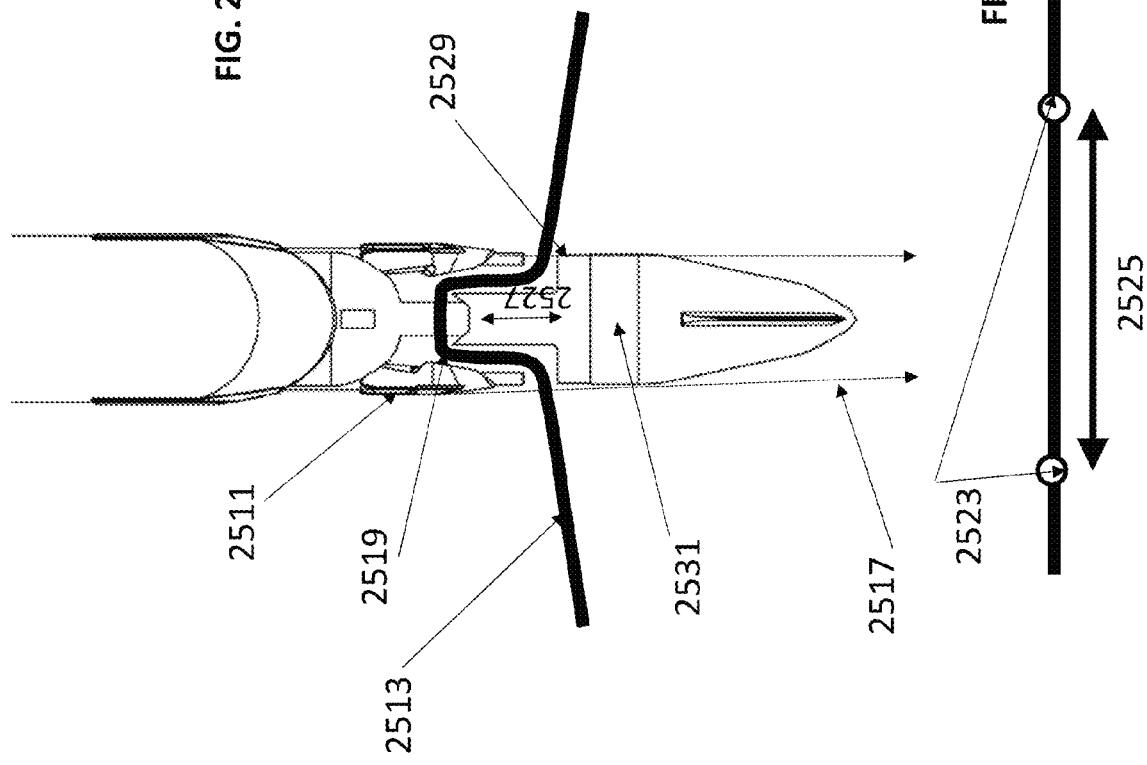
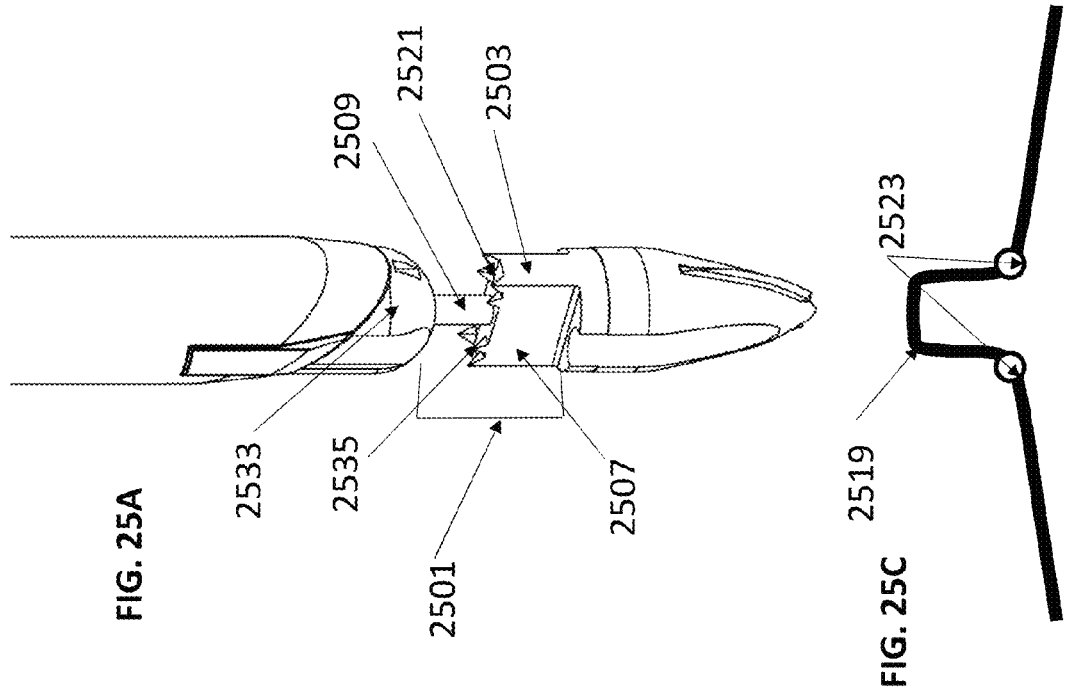

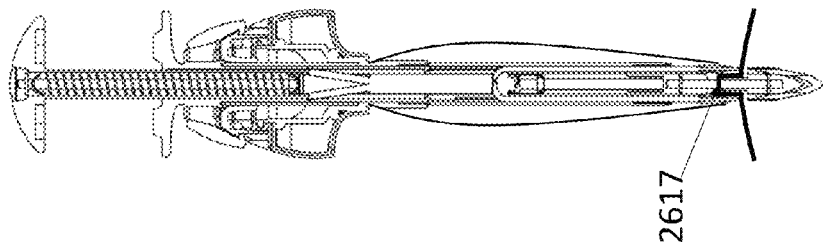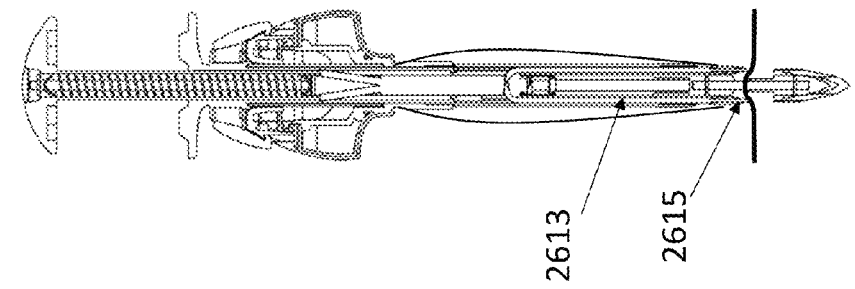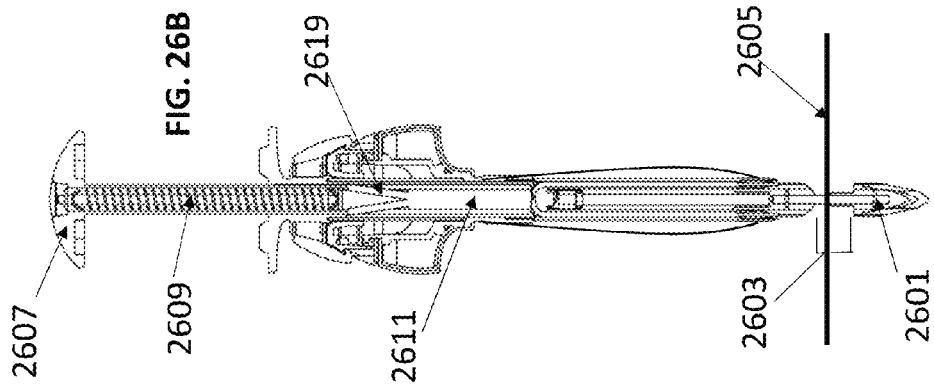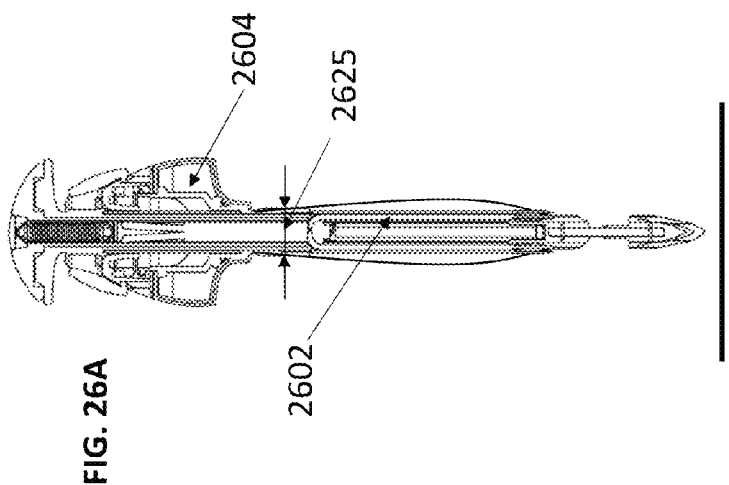

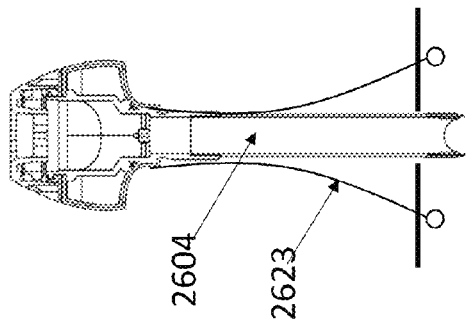
FIG. 26I
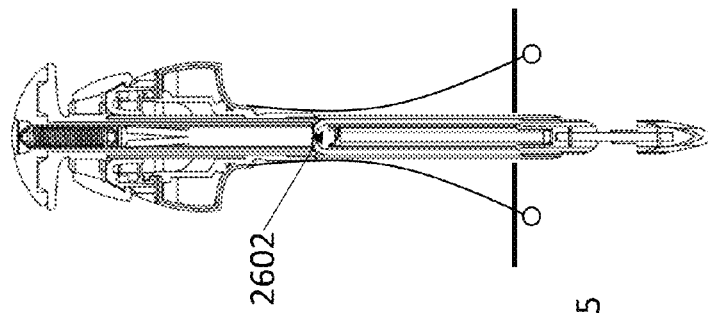
FIG. 26H
FIG. 26G
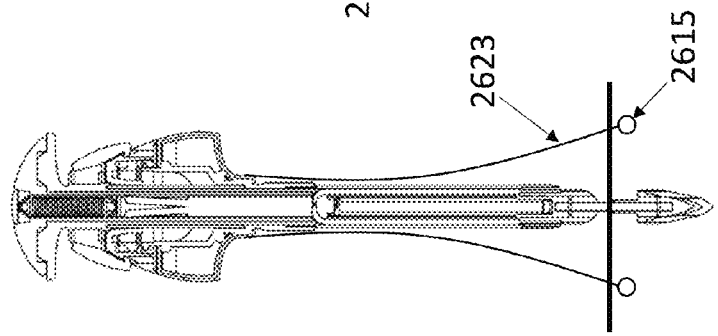
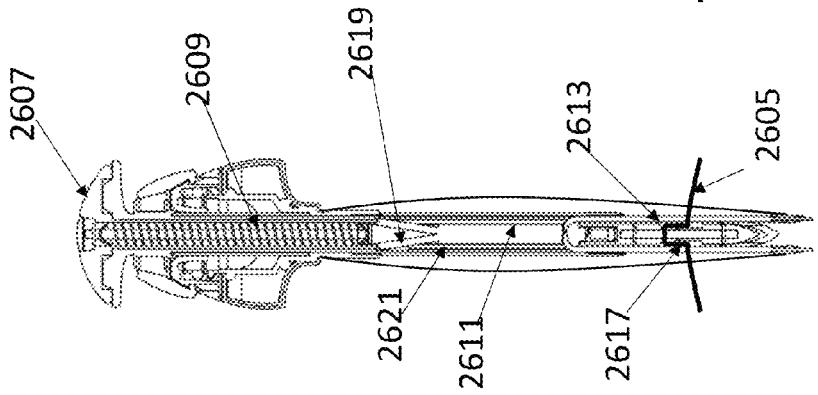
FIG. 26F
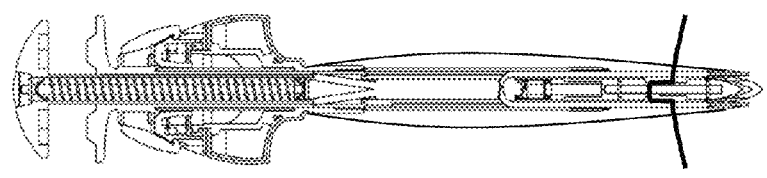
FIG. 26E

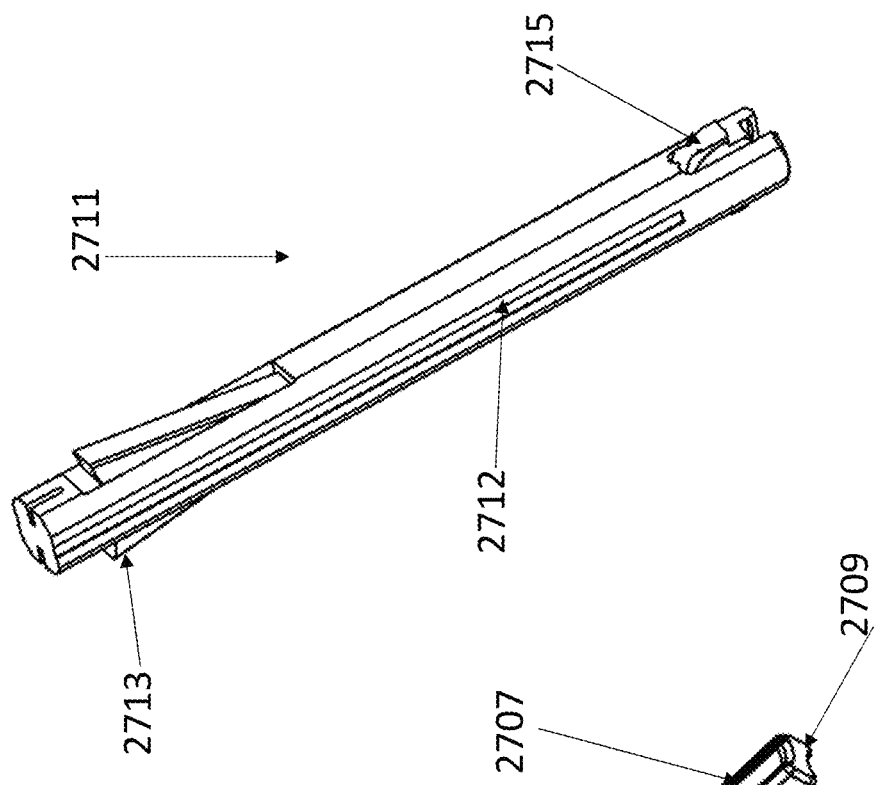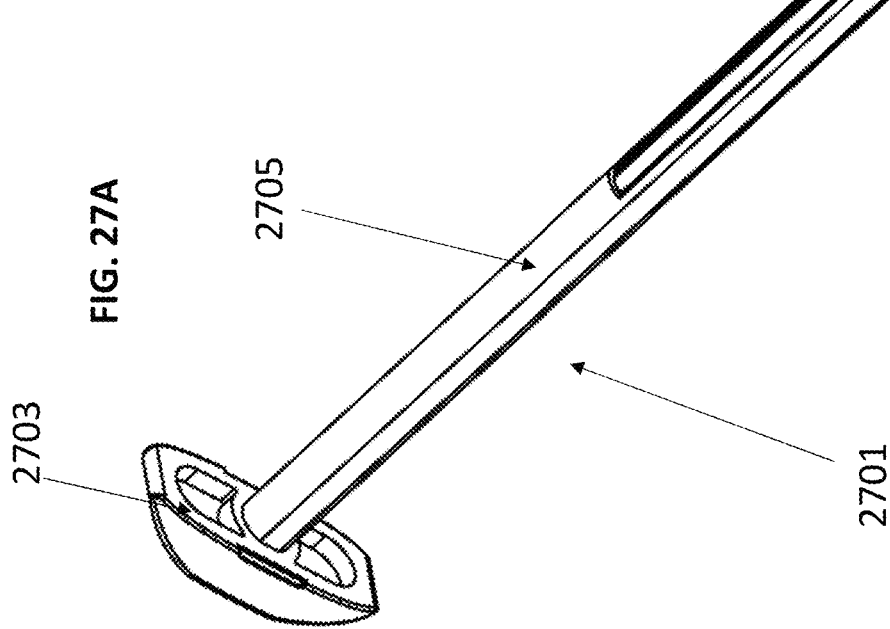

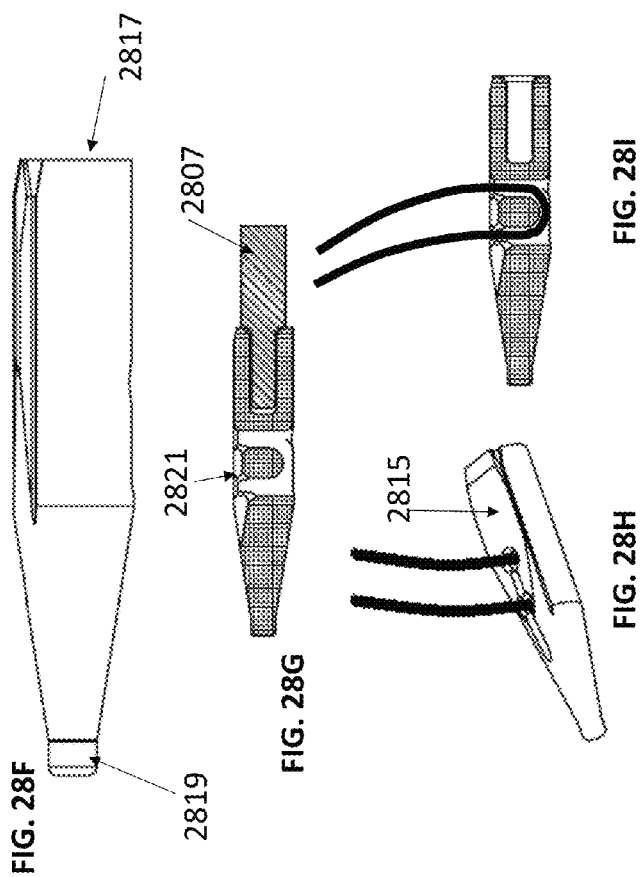
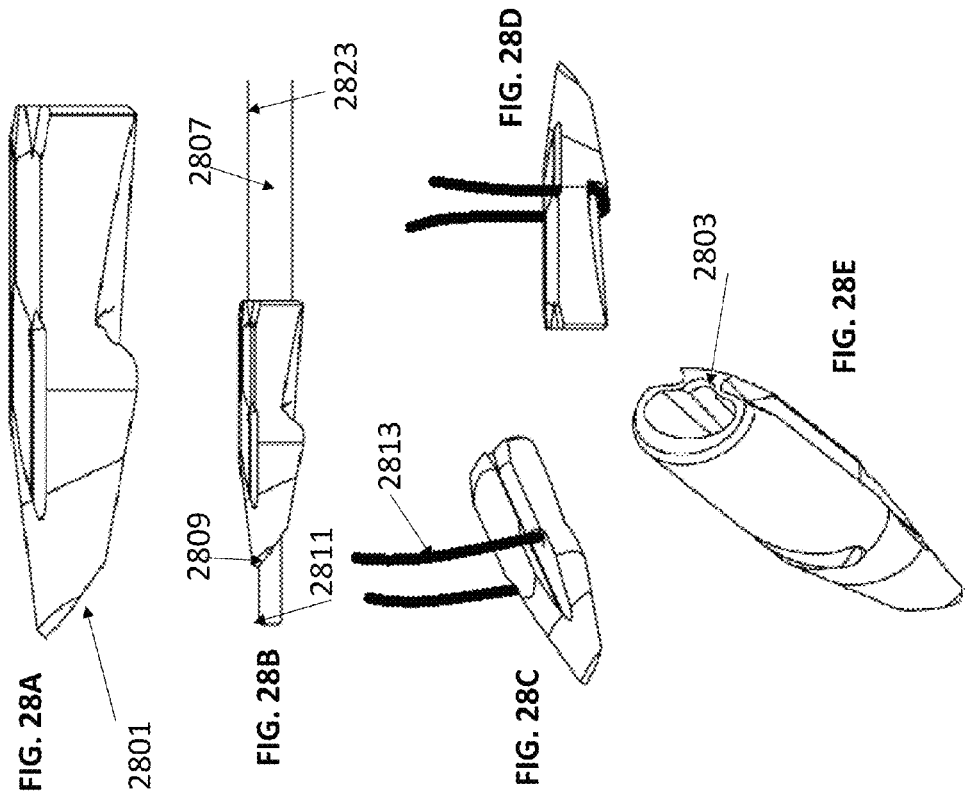

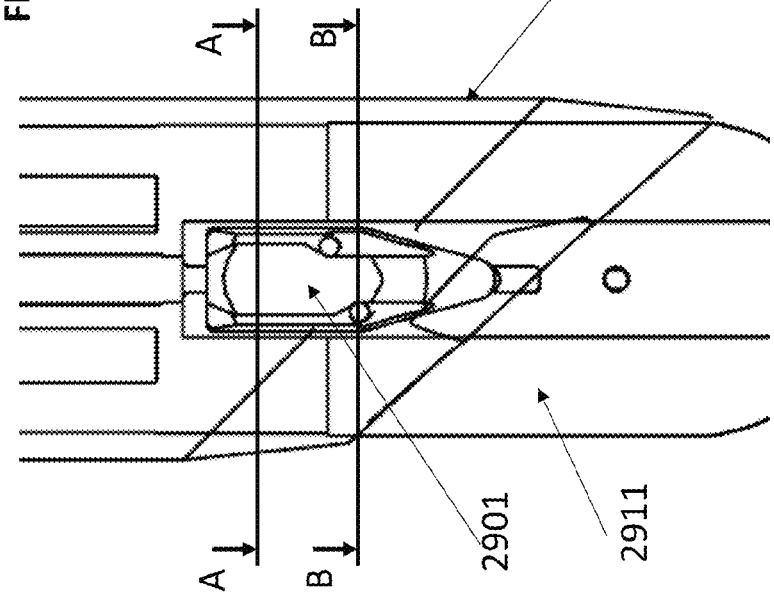
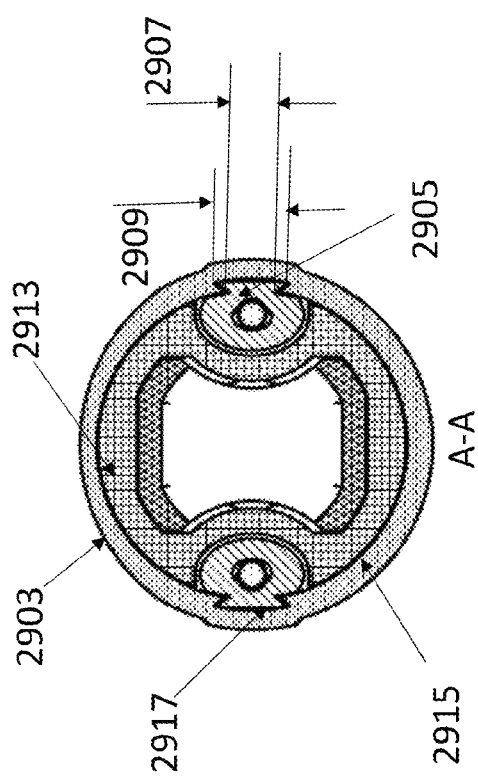
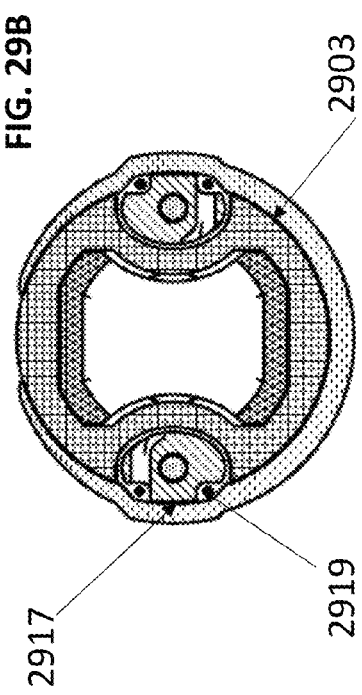
FIG. 29C
FIG. 29A
FIG. 29B

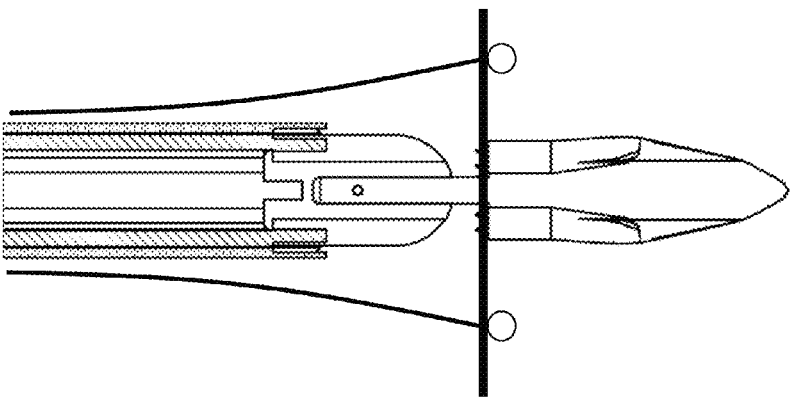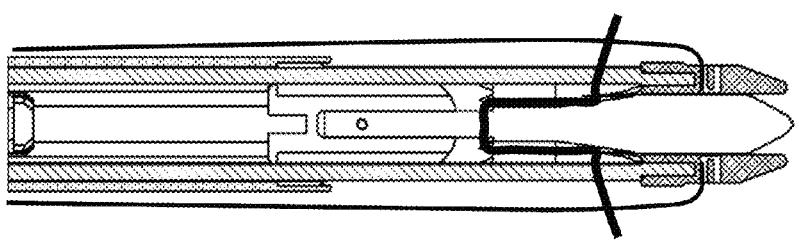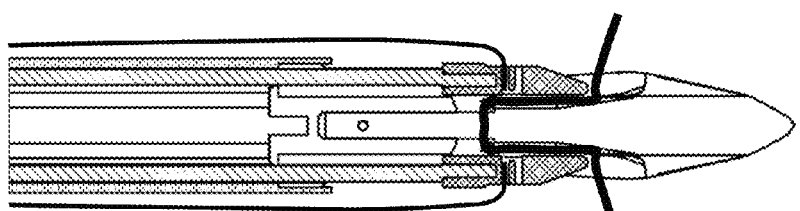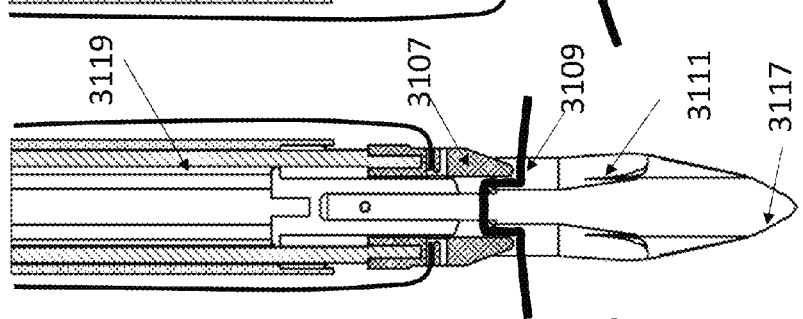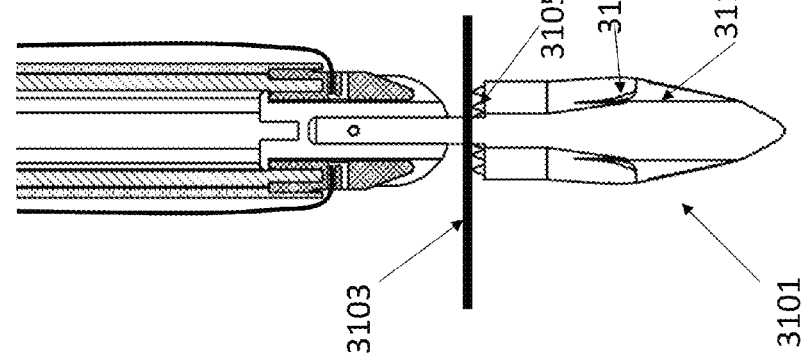

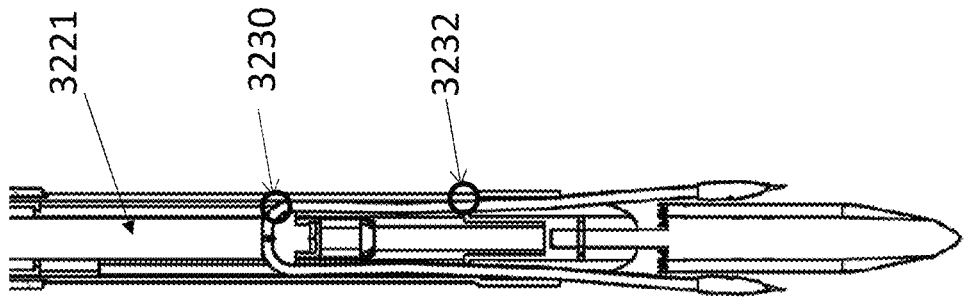
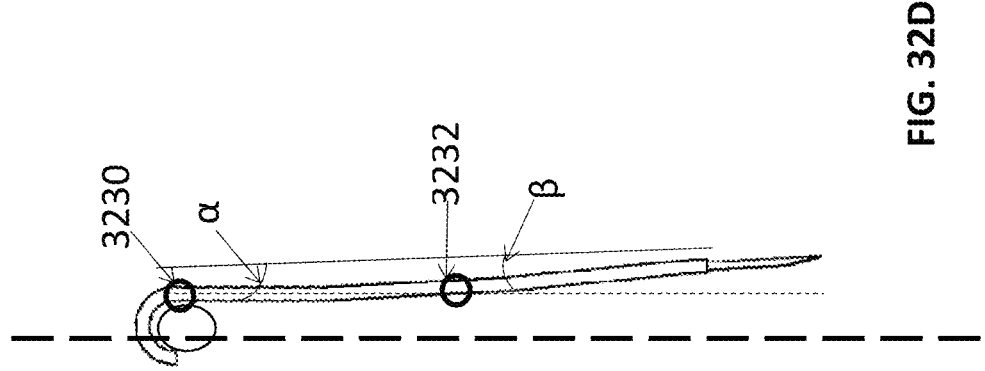
FIG. 32D
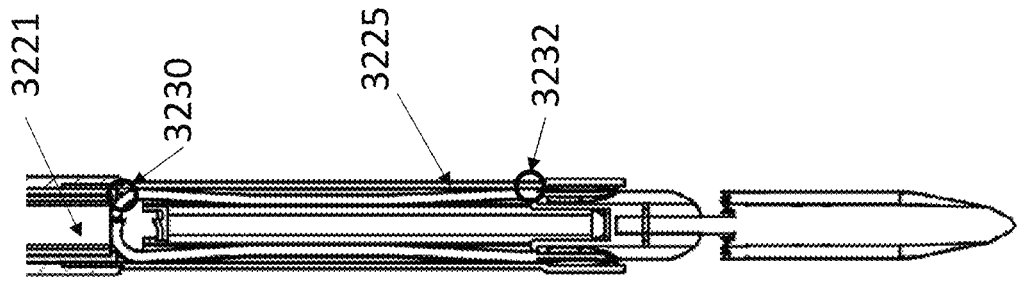
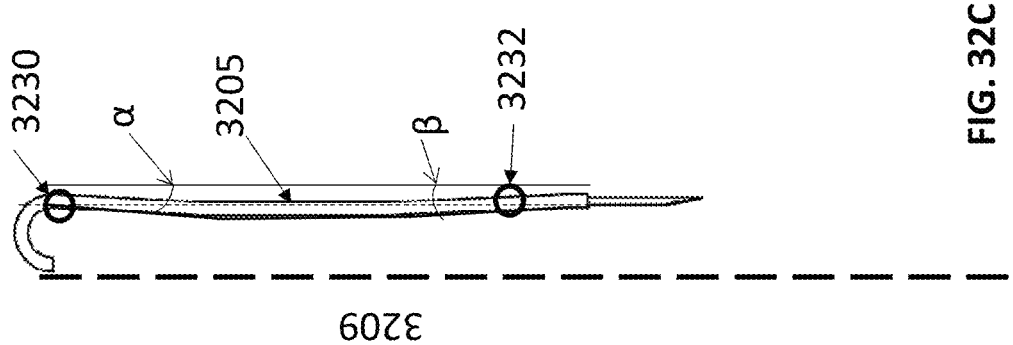
FIG. 32C

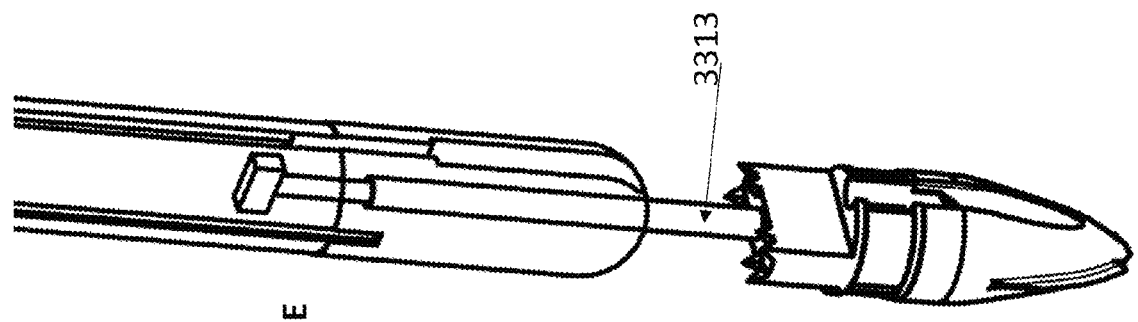
FIG. 33E
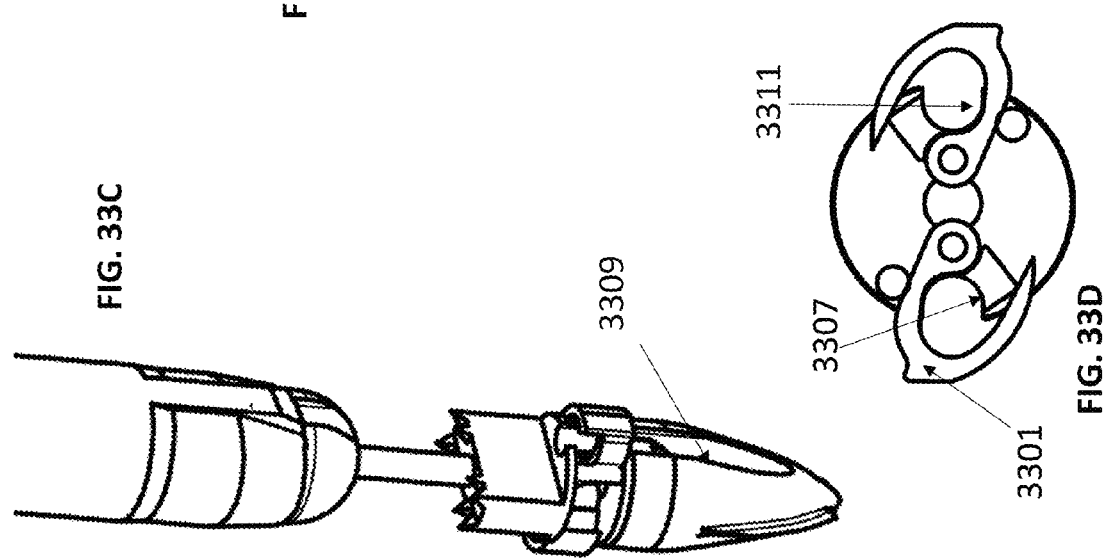
FIG. 33C
FIG. 33D
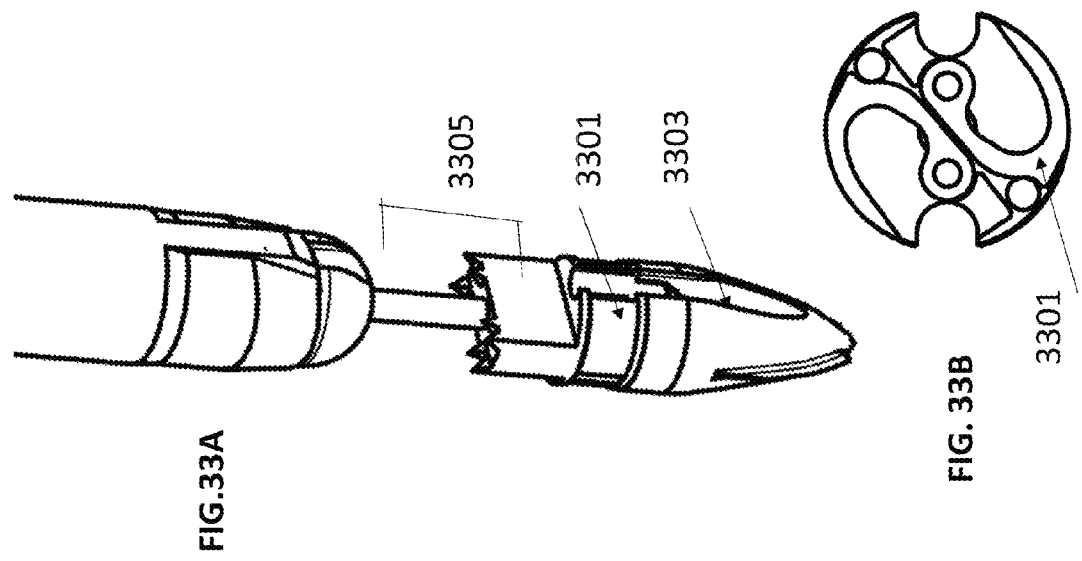
FIG. 33A
FIG. 33B

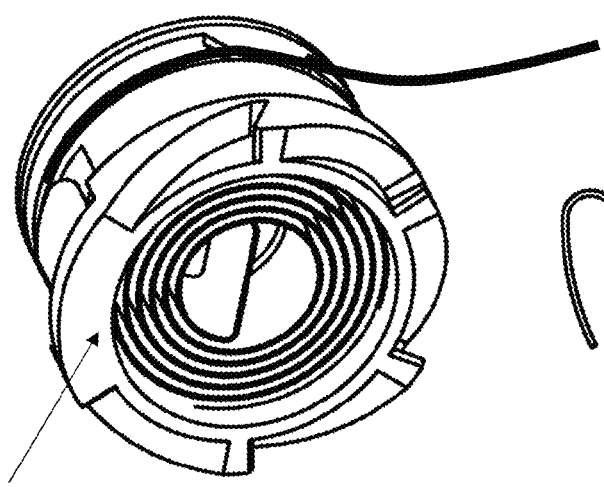
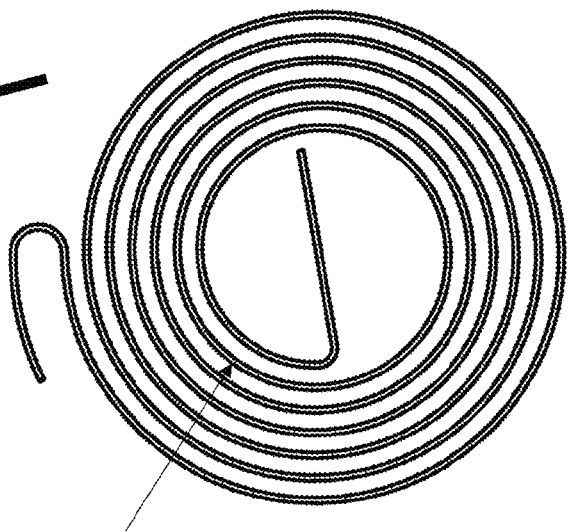
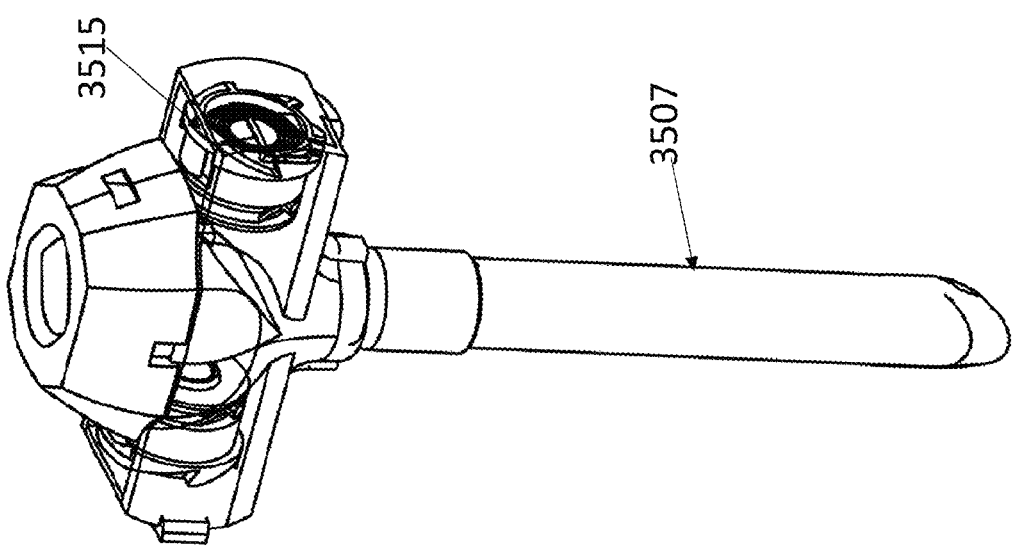

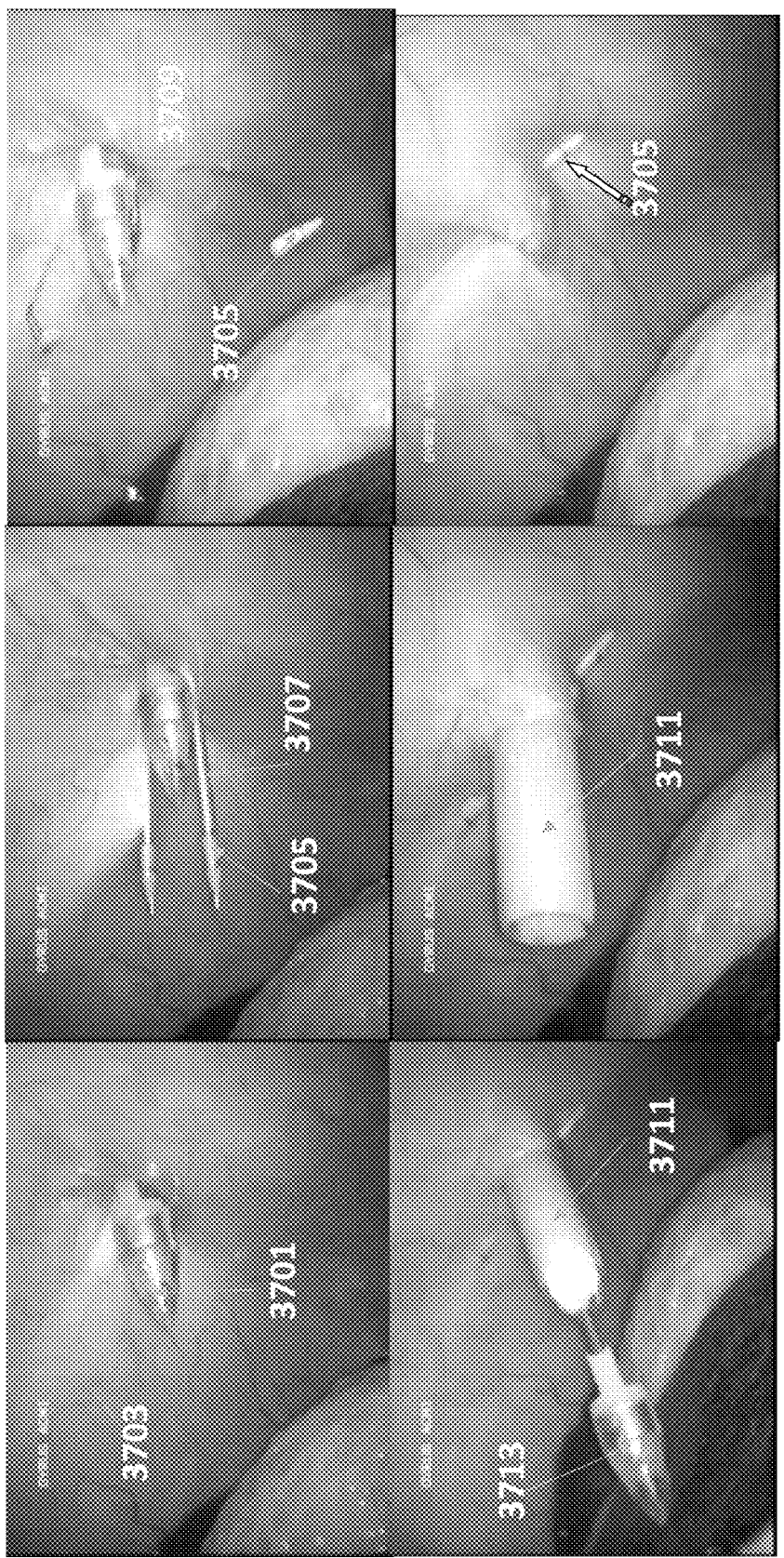

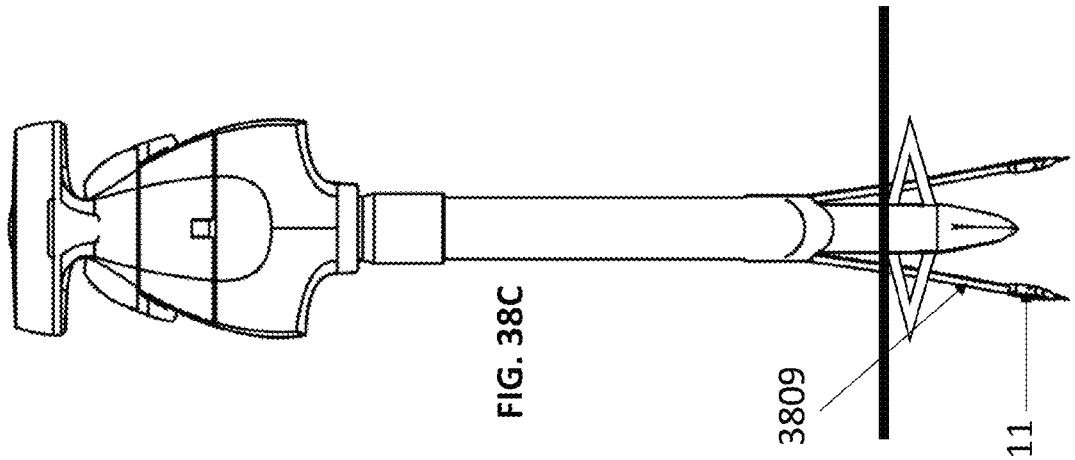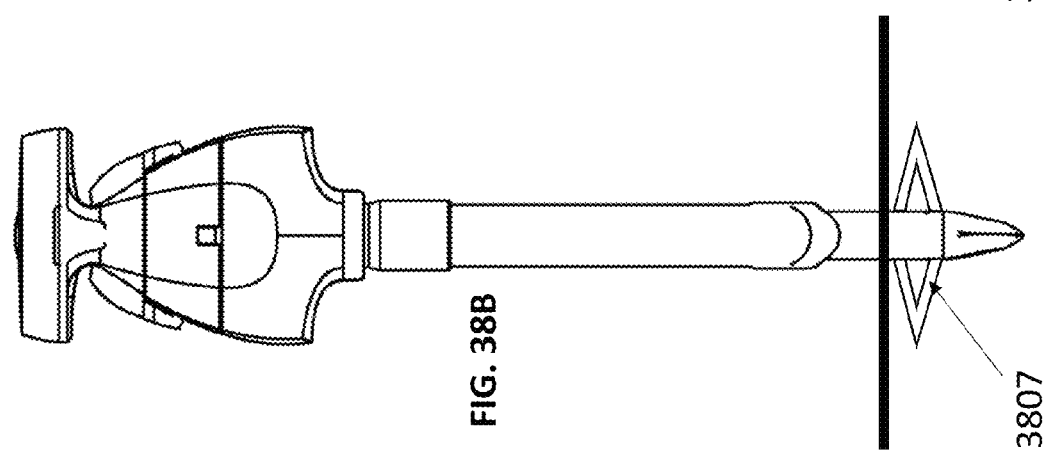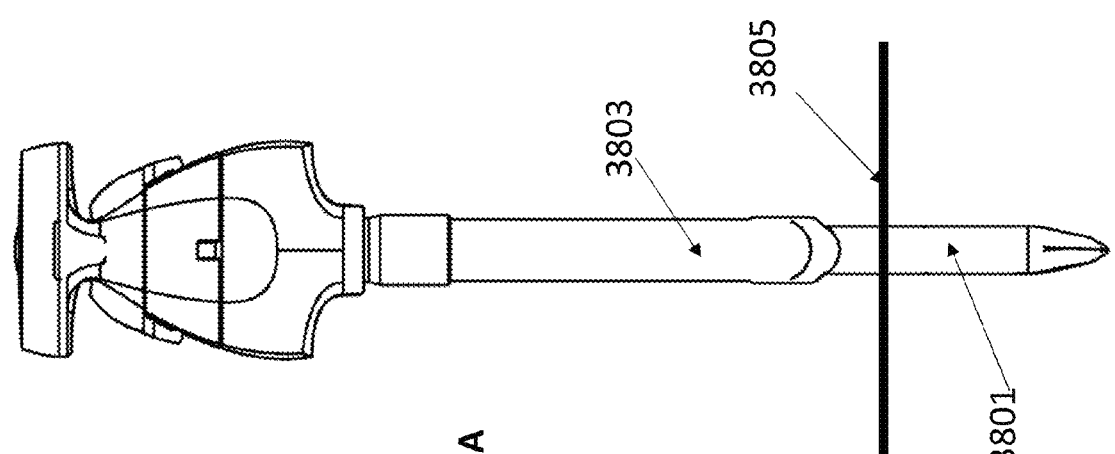

TROCAR AND WOUND CLOSURE DEVICE

RELATED APPLICATIONS

This application is a Continuation of PCT Patent Application No. PCT/IL2014/050833 filed on Sep. 17, 2014, which claims the benefit of priority under 35 USC §119(e) of U.S. Provisional Patent Application No. 61/878,660 filed on Sep. 17, 2013. The contents of the above applications are all incorporated by reference as if fully set forth herein in their entirety.

FIELD AND BACKGROUND OF THE INVENTION

The present invention, in some embodiments thereof, relates to a trocar, and, more particularly, but not exclusively, to a trocar and external cannula assembly for use in a laparoscopic procedure.

Laparoscopic surgery commonly includes the use of a trocar for introducing a laparoscope or other surgical instruments through an incised port in the abdominal wall. Following the procedure, various techniques may be used to provide wound closure, with or without visual control. Sufficient closure of the port is of major significance for prevention of complications such as hernia.

The following publications disclose a trocar wound closure device:

European patent publication number EP0568098 A2 to Greenwald et al. discloses "A trocar wound closure device (10) includes an elongated body (12) having a distal end (20) for insertion through a trocar puncture wound, a proximal end (14), and a first (70) and second (72) retractable needle holders disposed at the distal end (20) of the body (12). The needle holders (70, 72) are movable between a retracted position and an extended position. An actuator (32) disposed at the proximal end (14) of the body (12) moves the needle holders (70,72) from the retracted position to the extended position, so that the needle holders (70,72) can be retracted to allow the device (10) to be inserted through a trocar wound preferably through a cannula inserted into the wound, and extended to position the needles (56,58) adjacent the wound, to allow the wound to be sutured."

U.S. Pat. No. 8,109,943 to Boraiah et al. discloses "systems and methods for suture anchor deployment. A system according to the present invention is a trocar system that includes a cannula assembly and an obturator assembly, the cannula assembly providing a needle assembly and the obturator assembly providing a needle actuation mechanism. The obturator assembly may be at least partially inserted into the cannula assembly and arranged to operatively couple the needle actuation mechanism to the needle assembly. The needle assembly includes at least one needle, each needle having disposed near its distal tip a suture anchor. A method according to the present invention includes steps for deploying and/or depositing at least one suture anchor in or through an organ of the human body."

SUMMARY OF THE INVENTION

The present invention, in some embodiments thereof, relates to a trocar, and, more particularly, but not exclusively, to a trocar and external cannula assembly for use in a laparoscopic procedure.

According to an aspect of some embodiments of the invention there is provided a trocar adapted for insertion through a fascia layer of an abdominal wall, comprising: a proximal end configured for handling by a user; a distal end configured for insertion into tissue; and a shaft extending in between the proximal end and distal end; wherein the shaft comprises a narrow portion proximal to the distal end, the narrow portion defining at least one recess shaped and sized to receive fascia tissue, the recess ending, at a distal end of the recess, with a generally proximally facing surface of the shaft configured directly below the narrow portion, the proximally facing surface and the narrow portion shaped and sized to stabilize the trocar in the abdominal wall by the fascia. In some embodiments, the proximally facing surface comprises a tissue engaging geometry configured to restrict movement of the fascia tissue received within the recess away from the recess. In some embodiments, a length of the narrow portion is between 0.5-30 mm, and the recess is initiated at a distance of at least 0.5 mm from a longitudinal axis of the shaft, the recess having a depth of at least 1 mm in the radial direction. In some embodiments, a summed cross sectional area of the narrow portion is at least 50% less than a summed cross sectional area of at least one of a shaft portion configured above the narrow portion, and a shaft portion configured below the narrow portion on which the generally proximally surface is defined. In some embodiments, the narrow portion is long enough so as to receive a fascia tissue portion having a thickness of at least 0.5 mm. In some embodiments, the shaft is cylindrical, and the at least one recess is circumferential. In some embodiments, a diameter of a shaft portion configured directly below the narrow portion is larger than the diameter of the wound in the fascia layer so that tissue that has been stretched by the shaft portion during insertion springs back around the narrow portion when the narrow portion is positioned in fascia. In some embodiments, the tissue engaging geometry of the generally proximally facing surface comprises one or more projections. In some embodiments, the projections have tips in the direction of the fascia which prick the fascia to increase resistance. In some embodiments, a shaft portion configured above the narrow portion comprises a conical profile or a hemispherical profile increasing in diameter in the proximal direction, to provide increasing resistance during insertion of the apparatus into the abdominal wall.

In some embodiments, the trocar comprises at least one anchor thrusting element advanceable distally relative to the trocar shaft, and an anchor advancing mechanism. In some embodiments, the anchor advancing mechanism comprises a sliding element operably coupled to a handle for manipulation by a user, the sliding element comprising a geometry suitable to force the at least one anchor thrusting element distally when advanced within the shaft of the trocar. In some embodiments, the trocar comprises a spring and the at least one anchor thrusting element is automatically retracted by the spring, the spring configured not to resist advancement of the anchors into the tissue. In some embodiments, the trocar is configured to provide wound closure by further comprising at least one suture anchor and a suture coupled to the anchor. In some embodiments, the trocar comprises at least one proximally facing cutting element positioned distally to the narrow portion, the cutting element shaped to interact with the anchor to assist the anchor to penetrate the tissue. In some embodiments, the trocar further comprises one or more needles for deploying a suture in a tissue, the needles positioned within a trocar shaft portion configured below the narrow portion, with a sharp end of the needles facing the proximal direction. In some embodiments, the generally proximally facing surface comprises an expandable structure which when expanded increases the contact with fascia tissue facing the abdomen. In some embodiments, the expandable structure comprises a closed configuration for insertion or removal of the trocar, and an open configuration for preventing the trocar from being pulled in the proximal direction away from the fascia. In some embodiments, the structure is transformable into its open configuration by pulling the trocar in the proximal direction, against the fascia layer. In some embodiments, the expandable structure defines at least one frame through which an anchor is passed to be deployed in the tissue. In some embodiments, the expandable structure comprises a set of wings rotatable between a closed position and an open position in which they extend radially outwards relative to the shaft to define the frame. In some embodiments, the expandable structure comprises a set of arms configured to be axially compressed towards each other to define the frame. In some embodiments, a distal tip of the trocar is sharp enough to form the puncture wound upon insertion of the trocar into the abdominal wall. In some embodiments, a distal shaft portion of the trocar comprises one or more recesses shaped to form a tissue fold when the trocar is inserted into the tissue, the tissue fold formed between at least one of the narrow portion and the recessed shaft portion configured below the narrow portion, and the anchor.

According to an aspect of some embodiments of the invention there is provided a kit for use in a laparoscopic procedure, the kit comprising: a trocar, and an external cannula sized to receive the trocar, the cannula comprising at least one of anchors and sutures removably coupled to an inner wall of the cannula, wherein the trocar comprises an anchor advancing mechanism, the mechanism comprising at least one anchor thrusting element configured for extending externally to a shaft of the trocar to engage the anchor of the external cannula and advance the anchor into the tissue. In some embodiments, the anchor thrusting element is shaped as a rod, and a distal surface of the rod engages a proximal surface of the anchor. In some embodiments, the kit further comprises a plurality of external cannulas in which the trocar can be inserted. In some embodiments, a coupling between the anchors and the external cannula is structured not to interfere with insertion of the trocar into the cannula and advancement of the trocar to a ready to use position, in which the anchor thrusting element is located substantially above the anchor. In some embodiments, the anchor advancing mechanism is contained within a shaft of the trocar until operated to advance the anchors into the tissue. In some embodiments, the mechanism further comprises a sliding element operably coupled to a handle for manipulation by a user, the sliding element comprising a geometry suitable to force the anchor thrusting elements distally when advanced within the shaft of the trocar. In some embodiments, the anchors are configured to apply force on the tissue when advanced into the tissue without directly penetrating the tissue, forming a tissue fold between at least one of the narrow portion and a recessed shaft portion configured below the narrow portion, and the anchor. In some embodiments, the anchor comprises a hollow body shaped and sized to receive an anchor thrusting element, and at least one surface adapted for abutting against the fascia in a deployed position of the anchor. In some embodiments, the trocar comprises at least one proximally facing cutting element positioned distally to the narrow portion, the cutting element shaped to interact with the anchor to assist the anchor to penetrate the tissue. In some embodiments, the trocar comprises recesses alongside the walls of the shaft in which the anchor thrusting elements are advanced or retracted, the recesses configured in parallel to a longitudinal axis of the shaft. In some embodiments, the trocar shaft further comprises a spring, and the anchor thrusting elements are automatically retractable by the spring, the spring configured not to resist advancement of the anchors into the tissue. In some embodiments, an inner wall of the external cannula comprises at least one elongate recess in which at least a portion of the anchor is received, the recess defining a path for advancement of the anchor towards the tissue. In some embodiments, the recess is trapezoidal and defines a dovetail coupling between the anchor and the cannula. In some embodiments, at least one of the anchors and the sutures are absorbable in tissue. In some embodiments, a lumen of the external cannula is dimensioned for passing a laparoscope through. In some embodiments, the kit further comprises a sleeve for spatially orienting the trocar within the external cannula. In some embodiments, the sleeve seals a lumen between the trocar and cannula for preventing from gas to escape from within the abdomen. In some embodiments, a maximal diameter of the shaft together with the external cannula is between 15-30 mm.

According to an aspect of some embodiments of the invention there is provided an external cannula for positioning in an abdominal wall, the cannula comprising: at least one anchor removably attached to the cannula; at least one suture coupled to the anchor; an axially extending lumen sized for receiving a trocar, the trocar configured to engage the at least one anchor.

According to an aspect of some embodiments of the invention there is provided a method for deploying at least one of suture anchors and sutures at a fascia layer of the abdominal wall, comprising: positioning a trocar adapted for insertion into an abdominal wall such that a surface defined by a narrow portion of a shaft of the trocar abuts against a surface of the fascia facing the abdomen, and the narrow portion is surrounded by fascia tissue; deploying at least one of suture anchors or sutures into the fascia. In some embodiments, at least one of suture anchors and sutures are deployed at a predefined depth with respect to the fascia layer. In some embodiments, positioning further comprises slightly stretching the fascia tissue against the surface defined below the narrow portion, by pulling the trocar in the proximal direction. In some embodiments, a single trocar is inserted into a plurality of external cannulas, each cannula positioned at a different port, to deploy suture anchors separately at each port.

According to an aspect of some embodiments of the invention there is provided a method for providing sensible feedback to a user for positioning a trocar adapted for insertion into an abdominal wall, the trocar comprising a shaft formed with a narrow portion in proximity to a distal end of the trocar; comprising: inserting the trocar through an abdominal wall; pulling the trocar in the proximal direction until encountering resistance formed by a surface of the shaft defined below the narrow portion abutting against a fascia layer of the abdominal wall; and positioning the trocar so that the fascia layer enters one or more recesses defined by the narrow portion. In some embodiments, the method further comprises deploying anchors at the fascia layer.

According to an aspect of some embodiments of the invention there is provided a method of increasing a distance between suture anchors during deployment of the suture anchors in the tissue, comprising crimping the tissue to a substantial upside down U shape; penetrating the crimped tissue at the bases of the upside down U shape using the suture anchors, and deploying the anchors in the tissue; releasing the tissue fold to have the suture anchors deployed at a larger distance from each other in comparison to a distance between the suture anchors that would have been obtained without the tissue fold. In some embodiments, crimping is obtained by advancing the suture anchors before penetrating the tissue to force the tissue into a recess of an anchor deploying apparatus.

According to an aspect of some embodiments of the invention there is provided an apparatus adapted for insertion in a fascia layer of an abdominal wall, comprising: a proximal end configured for handling by a user; a shaft comprising a distal end configured for insertion into tissue; at least one anchor for deployment into the tissue, the anchor removably coupled to the shaft; wherein the distal end of the shaft comprises at least one proximally facing element which interacts with the anchor to assist the anchor to penetrate the tissue by contacting the tissue from two substantially opposite directions. In some embodiments, the proximally facing element comprises proximally facing cutting edge or tip.

According to an aspect of some embodiments of the invention, there is provided an apparatus adapted for insertion in a puncture wound of at least 3 mm in diameter in a fascia layer of an abdominal wall, comprising: a proximal end configured for handling by a user, a shaft, and a distal end configured for insertion into tissue, wherein the shaft comprises a narrow portion proximal to the distal end, the narrow portion having a length ranging between 0.5-20 mm, the narrow portion defined by at least one recess, the recess initiated at a distance of at least 0.5 mm from a longitudinal axis of the shaft, the recess having a depth of at least 1 mm in the radial direction for receiving at least a portion of fascia layer tissue that springs back around the shaft. In some embodiments, a periphery of the narrow portion is smaller than a periphery of at least one of a shaft portion configured above the narrow portion, and a shaft portion configured below the narrow portion. In some embodiments, a summed cross sectional area of the narrow portion is at least 50% less than a summed cross sectional area of at least one of a shaft portion configured above the narrow portion, and a shaft portion configured below the narrow portion. In some embodiments, the narrow portion is long enough so as to receive fascia tissue having a thickness of at least 0.5 mm. In some embodiments, the shaft is cylindrical. In some embodiments, the at least one recess is configured circumferentially around the shaft. In some embodiments, a diameter of the narrow portion is shorter than the diameter of the wound in the fascia layer so that tissue that has been stretched by the shaft springs back around the narrow portion. In some embodiments, a surface defined by the narrow portion below the narrow portion which faces a proximal direction comprises one or more projections. In some embodiments, the projections have tips in the direction of the fascia which prick the fascia to increase resistance. In some embodiments, the projections are distributed circumferentially around a perimeter of the surface. In some embodiments, a geometry of the apparatus provides an indication of a current depth of the apparatus with respect to the tissue to a user. In some embodiments, a shaft portion configured above the narrow portion comprises a conical profile increasing in diameter in the proximal direction, to provide increasing resistance during insertion of the apparatus into the abdominal wall. In some embodiments, the distal end of the apparatus is bladed for incising the puncture wound in the fascia. In some embodiments, the distal end is bladeless. In some embodiments, a pulling force of up to 40 N can be applied to the apparatus without causing a proximal facing surface of the shaft defined below the narrow portion to pass back through the wound in the tissue, the surface being larger than the wound for resisting the pulling. In some embodiments, the shaft comprises a hollow lumen for insertion of the apparatus over a guide wire. In some embodiments, a proximal facing surface of the shaft defined below the narrow portion comprises an expandable structure configured for abutting against a surface of the fascia facing the abdomen. In some embodiments, the expandable structure comprises segmented leaflets. In some embodiments, the expandable structure comprises a closed configuration for insertion or removal of the apparatus, and an open configuration for preventing the apparatus from being pulled in the proximal direction. In some embodiments, the expandable structure is transformable into its open configuration by pulling the apparatus in the proximal direction, against the fascia layer. In some embodiments, a distance between a surface defined below the narrow portion and the distal end ranges between 10-50 mm. In some embodiments, the apparatus comprises at least one of sutures and suture anchors for deploying into the fascia for providing wound closure. In some embodiments, at least one of a distance between the narrow portion and a distal tip of the apparatus, and a distance range of the suture anchors during deployment determines a position of the at least one of sutures and suture anchors with respect to the fascia. In some embodiments, the apparatus comprises anchor thrusting elements for delivering the anchors towards the fascia. In some embodiments, the shaft comprises recesses alongside the walls of the shaft for receiving the thrusting elements. In some embodiments, the recesses are configured in parallel to a longitudinal axis of the shaft, so that anchors are deployed in parallel to the axis. In some embodiments, the recesses are arched so that anchors are deployed at an angle to a longitudinal axis of the shaft. In some embodiments, the shaft further comprises a spring, and the anchor thrusting elements are automatically retractable by the spring. In some embodiments, the device further comprises a cannula external to the apparatus. In some embodiments, the cannula comprises the at least one of sutures and suture anchors. In some embodiments, the sutures are threaded through the anchors. In some embodiments, at least one of the anchors and the sutures are absorbable in tissue. In some embodiments, the external cannula is dimensioned for passing a laparoscope through. In some embodiments, the apparatus comprises a ratchet based anchor applicator. In some embodiments, the ratchet prevents upward movement of anchor thrusting elements during anchor deployment. In some embodiments, the apparatus further comprises a sleeve for spatially orienting the apparatus within the external cannula. In some embodiments, the sleeve seals a lumen between the apparatus and cannula for preventing from gas to escape from within the abdomen. In some embodiments, the apparatus comprises one or more needles for deploying a suture in a tissue. In some embodiments, the needles are positioned within a shaft portion configured below the narrow portion, with a sharp end of the needles facing the proximal direction. In some embodiments, the apparatus comprises a removal configuration in which the needles are retracted along with the apparatus, while the suture remains within the tissue. In some embodiments, the tissue is fascia layer.

According to an aspect of some embodiments of the invention there is provided a method for deploying at least one of suture anchors and sutures at a fascia layer of the abdominal wall, comprising: positioning an apparatus adapted for insertion into an abdominal wall for providing wound closure such that a surface defined by a narrow portion of a shaft of the apparatus abuts against a surface of the fascia facing the abdomen, and the narrow portion is surrounded by fascia tissue; and deploying at least one of suture anchors or sutures into the fascia. In some embodiments, at least one of suture anchors and sutures are deployed at a predefined depth with respect to the fascia layer. In some embodiments, positioning further comprises slightly stretching the fascia tissue against the surface defined below the narrow portion, by pulling the apparatus in the proximal direction. In some embodiments, the apparatus in inserted through an external cannula, and deploying comprises forcing anchors positioned at the external cannula to advance towards the fascia. In some embodiments, a single apparatus is inserted into a plurality of external cannulas, each cannula positioned at a different port, to deploy suture anchors separately at each port.

According to an aspect of some embodiments of the invention there is provided a method for providing sensible feedback to a user for positioning an apparatus adapted for insertion into an abdominal wall, the apparatus comprising a shaft formed with a narrow portion in proximity to a distal end of the apparatus; comprising: inserting the apparatus through an abdominal wall, pulling the apparatus in the proximal direction until encountering resistance formed by a surface of the shaft defined below the narrow portion abutting against a fascia layer of the abdominal wall; and positioning the apparatus so that the fascia layer springs back around the narrow portion. In some embodiments, the apparatus is adapted for anchor deployment, and the method further comprises deploying anchors at the fascia layer. In some embodiments, increased resistance is provided by the proximal facing shaft surface comprising one or more projections which prick into the fascia.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

Figure 4A:
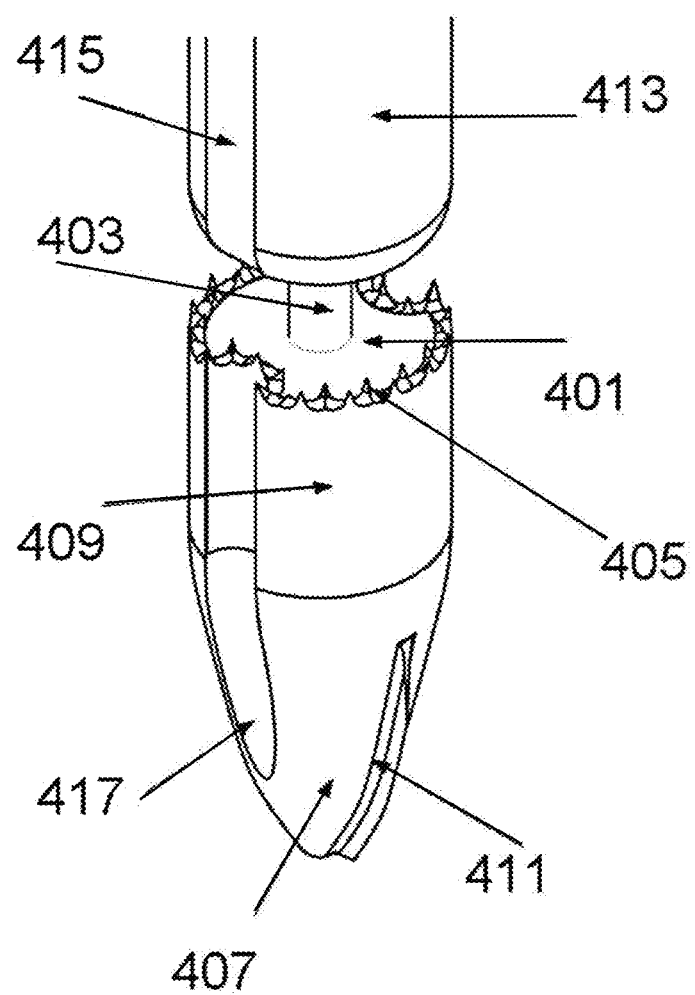
Figure 5B:
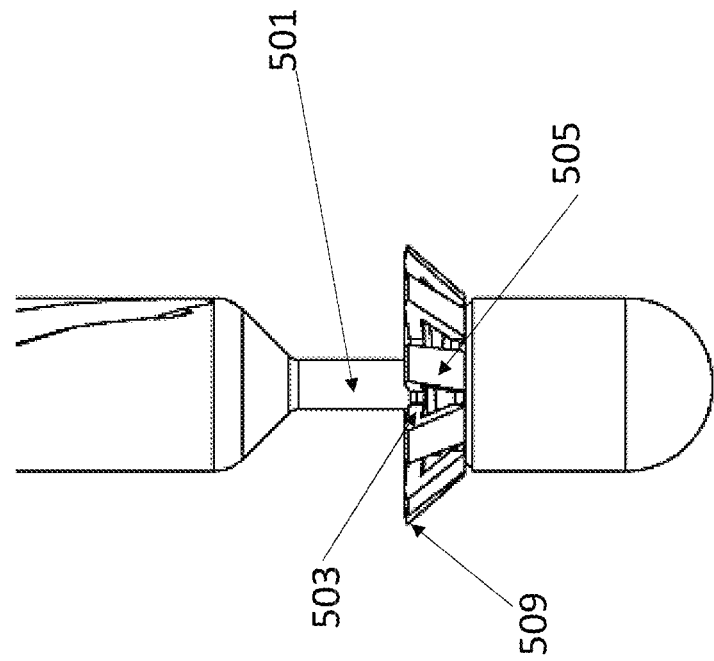
Figure 5A:
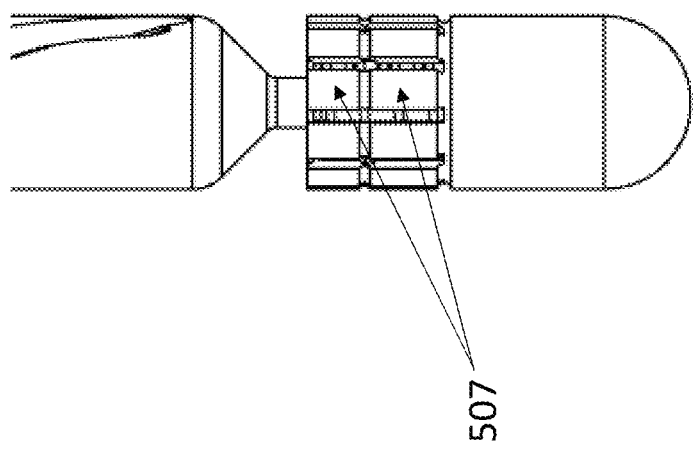
Figures 7A, 7B:
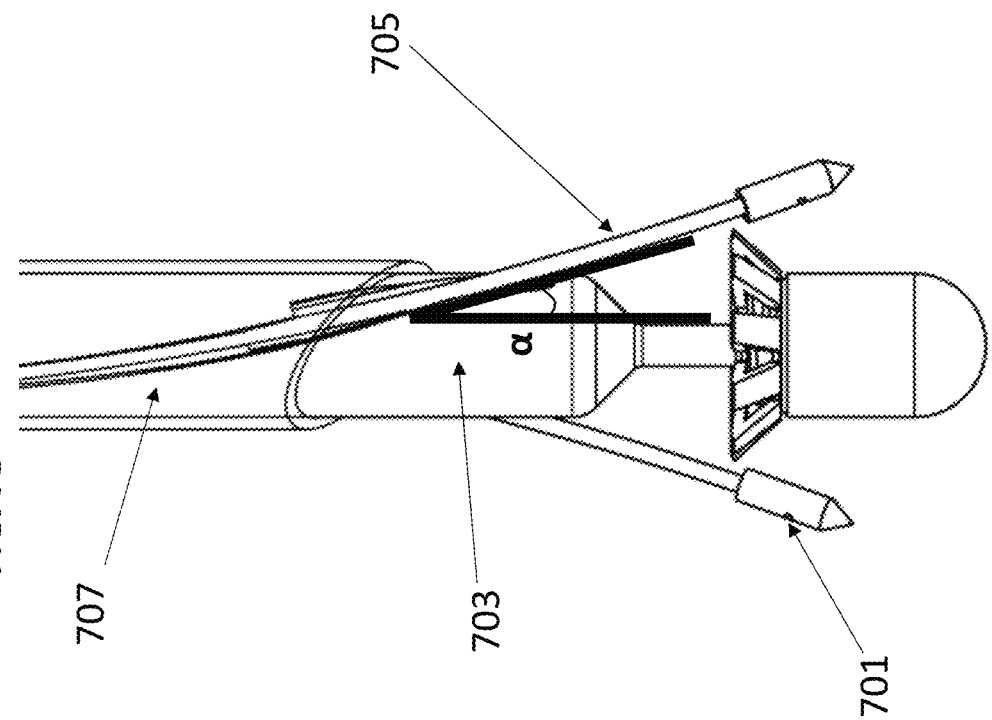
Figure 8B:
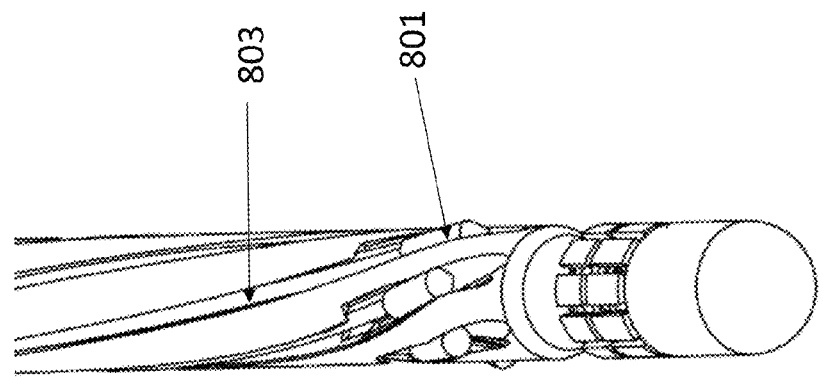
Figure 8A:
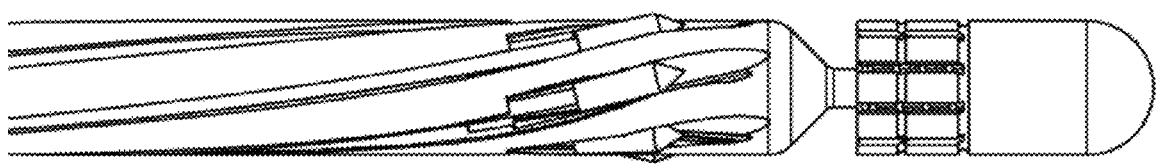
Figure 10:
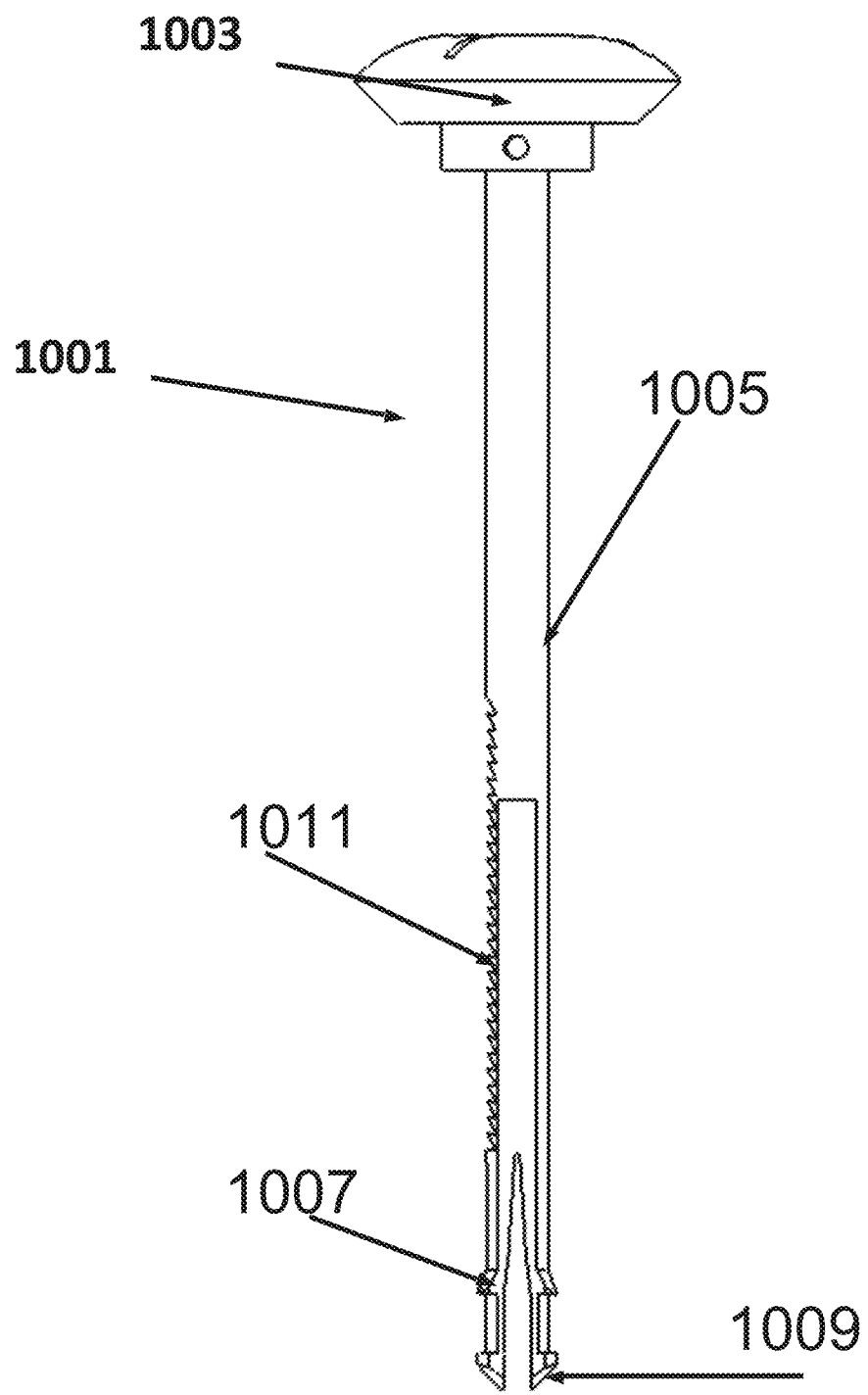
Figure 13:
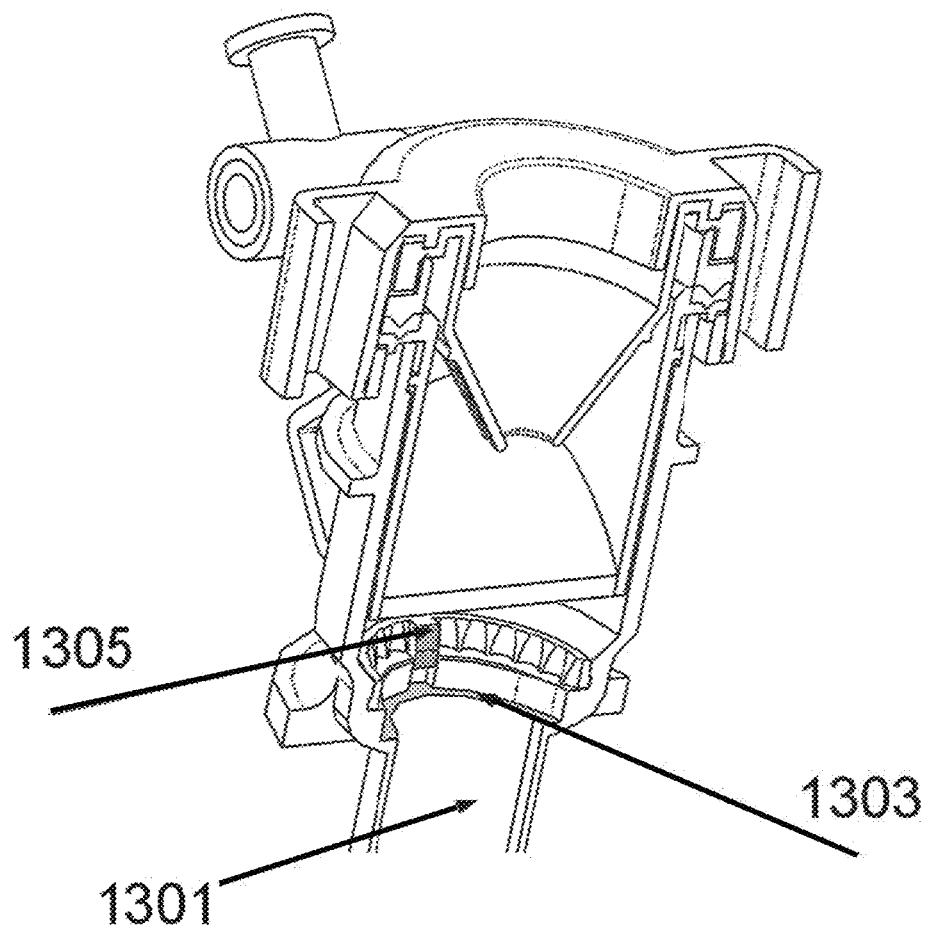
Figure 14:
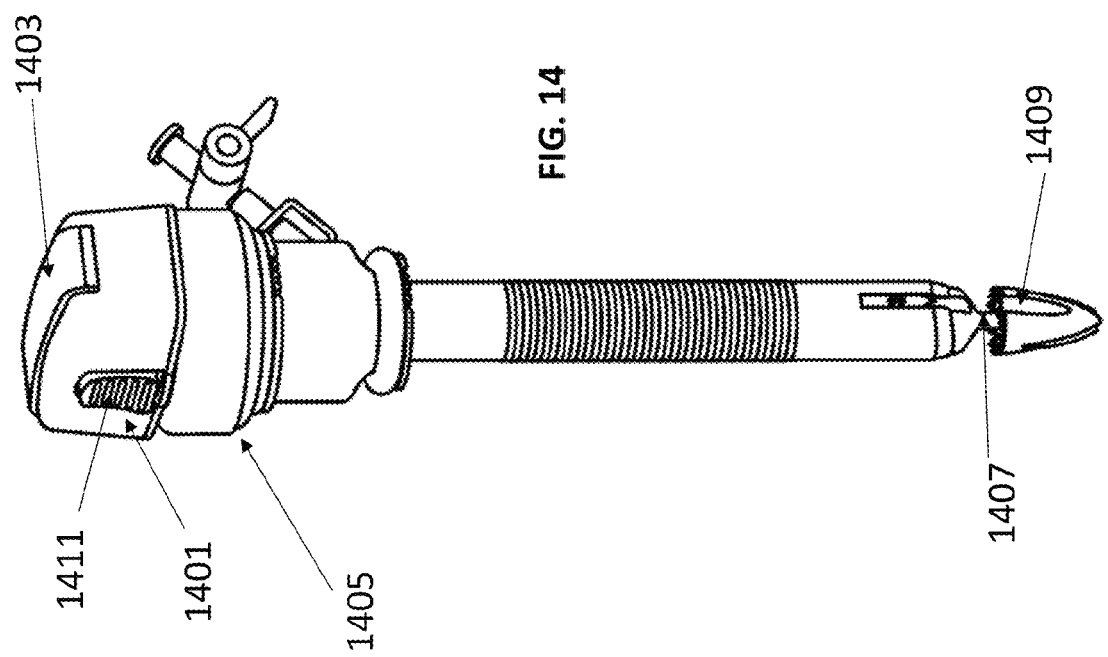
Figure 16C:
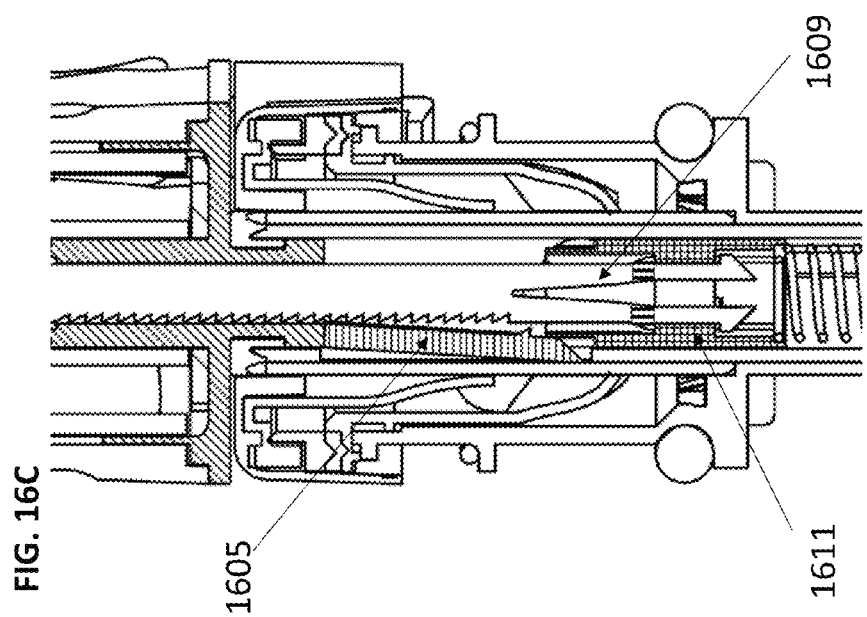
Figure 16B:
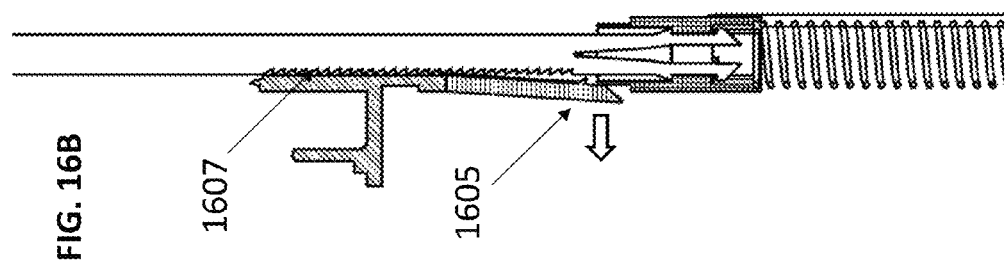
Figure 16A:
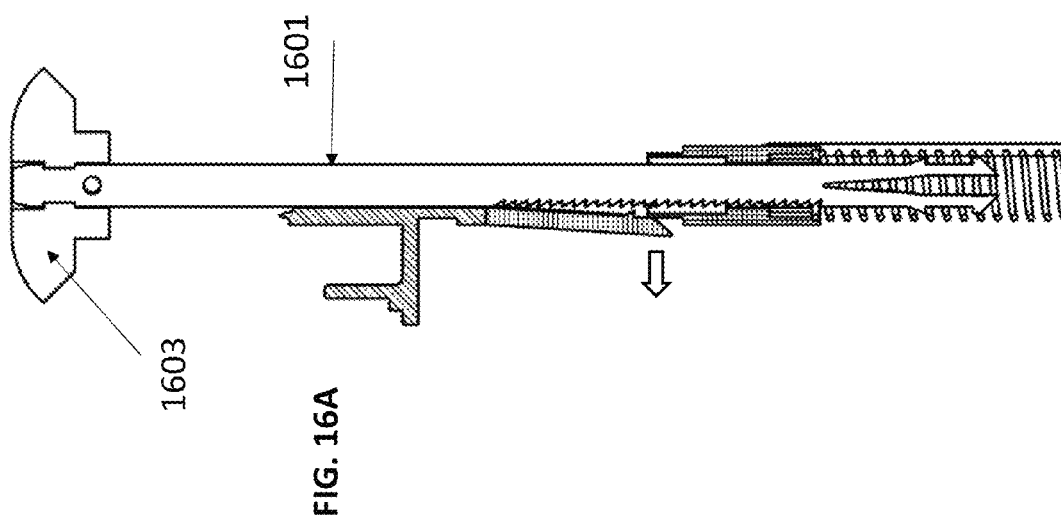
Figure 18:
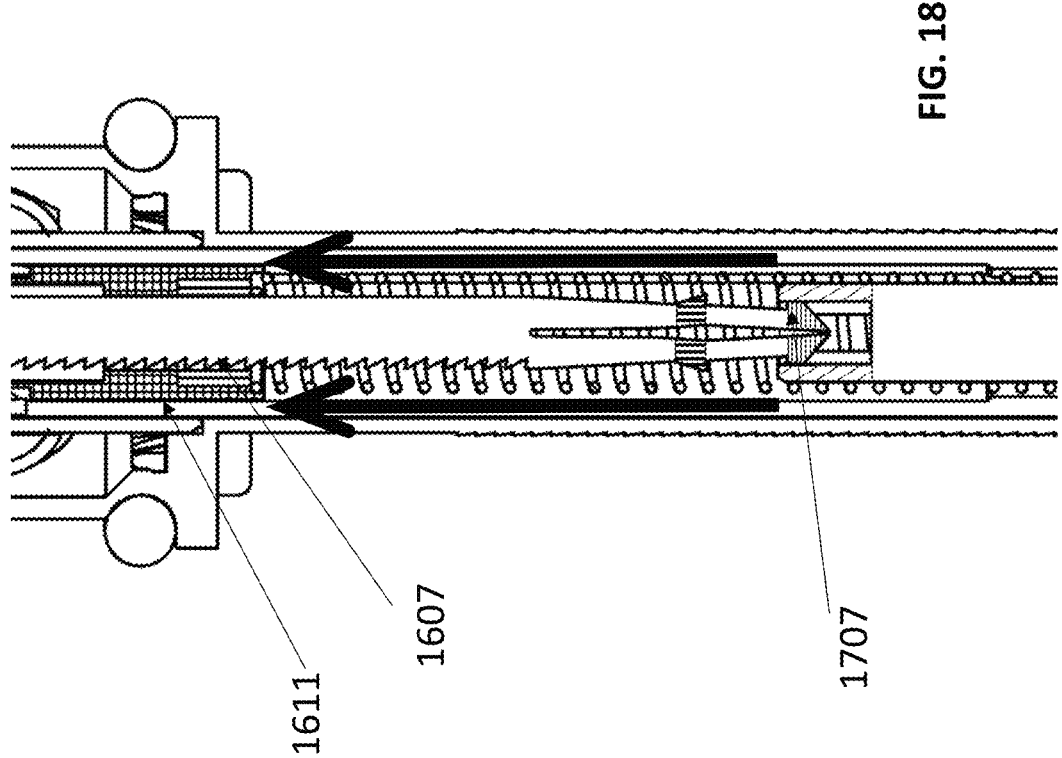
Figure 19B:
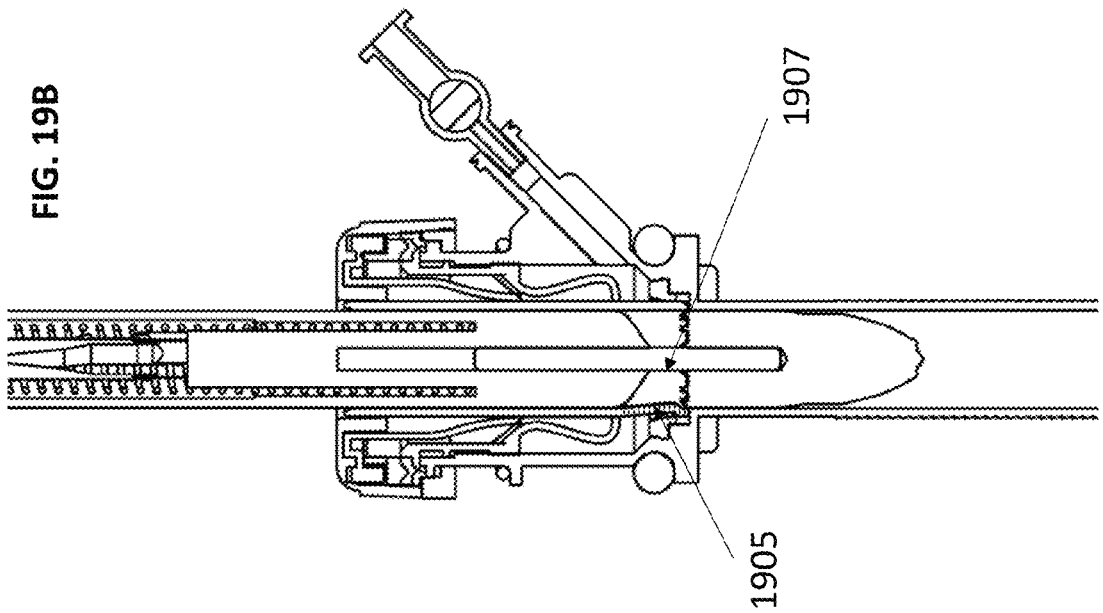
Figure 19A:
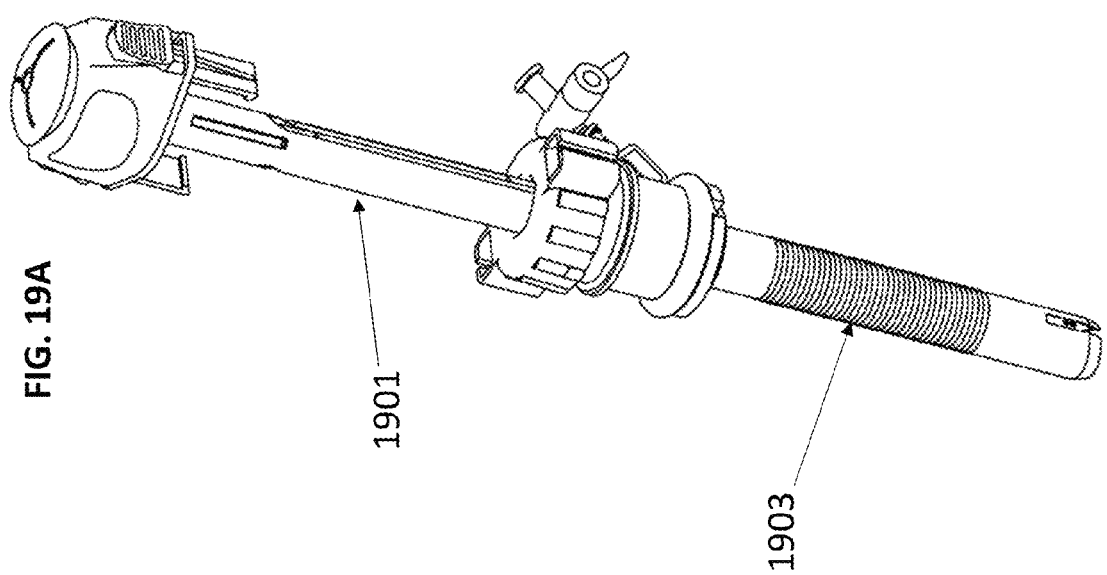
Figure 20:
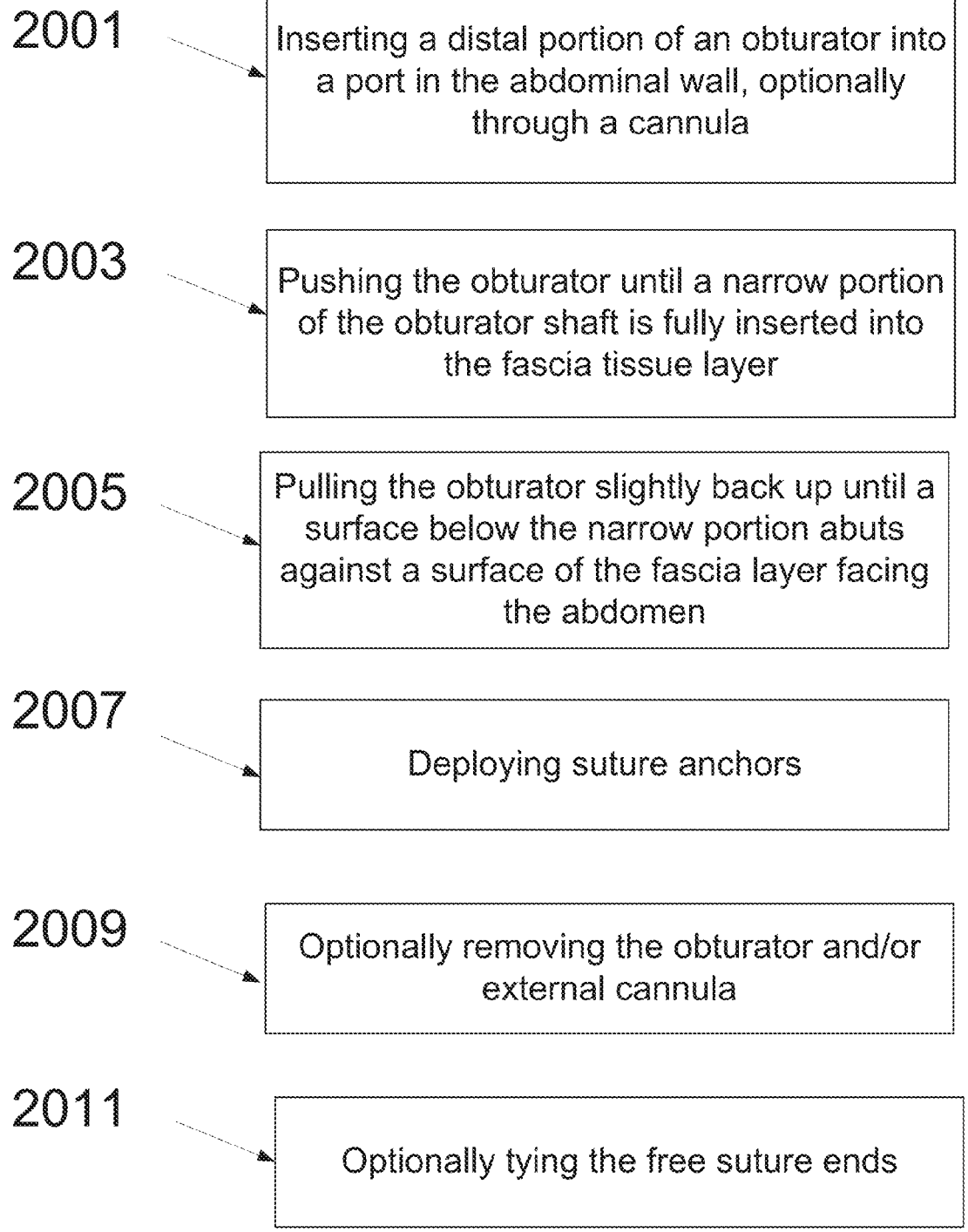
Figure 22:
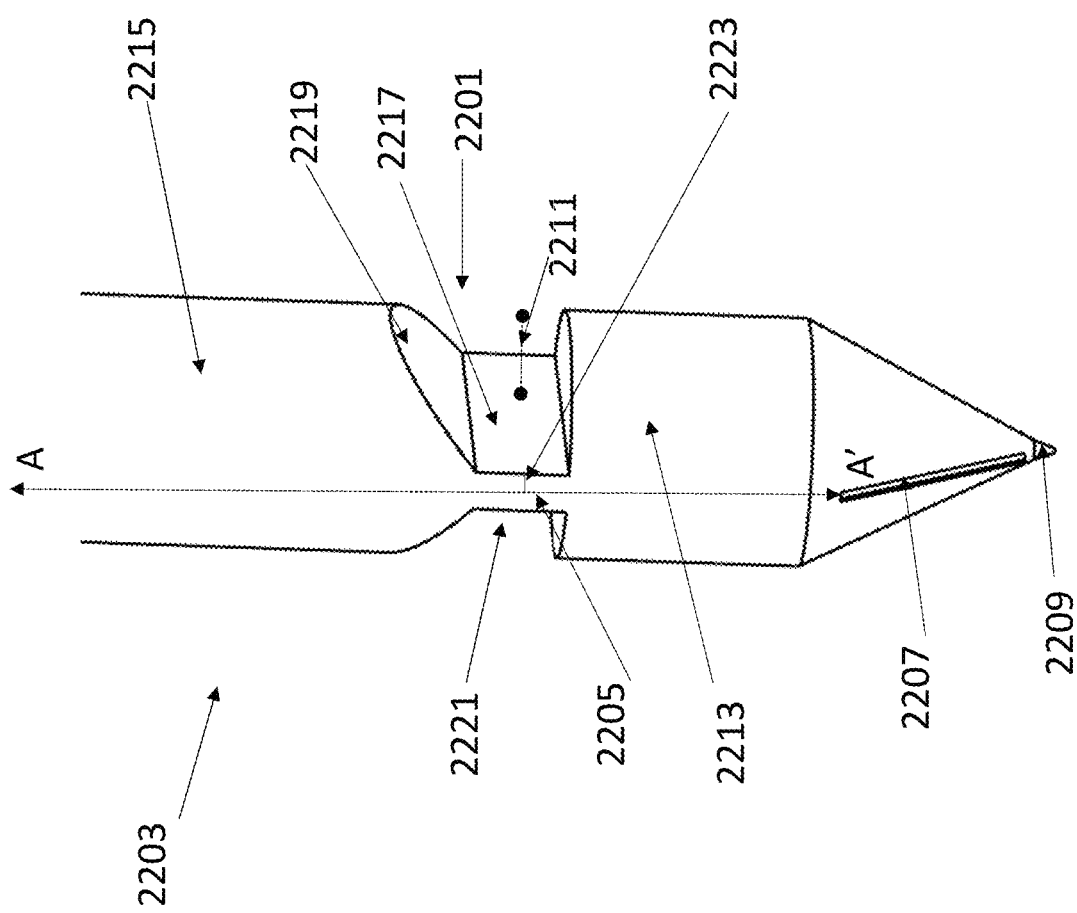
Figure 30B:
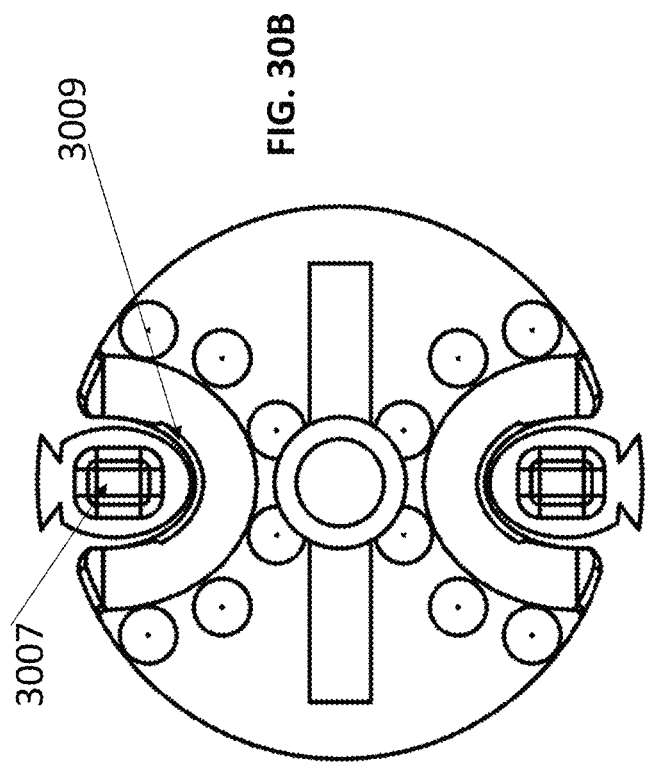
Figure 30C:
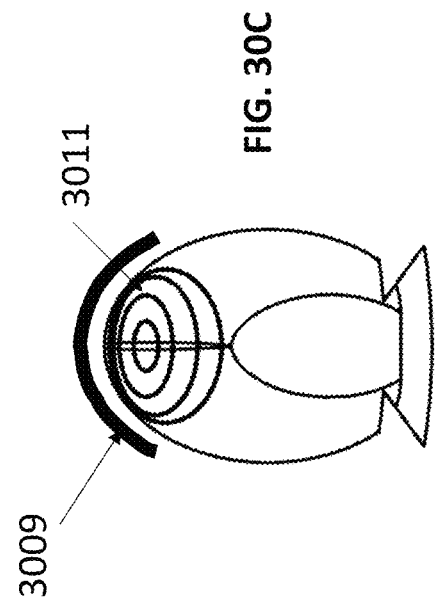
Figure 30A:
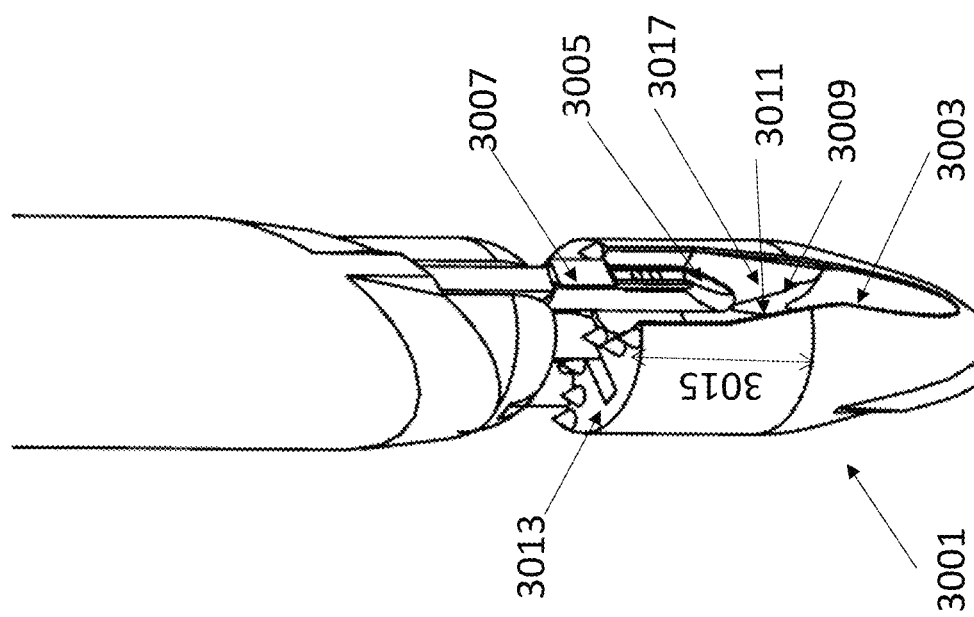
Figure 36B:
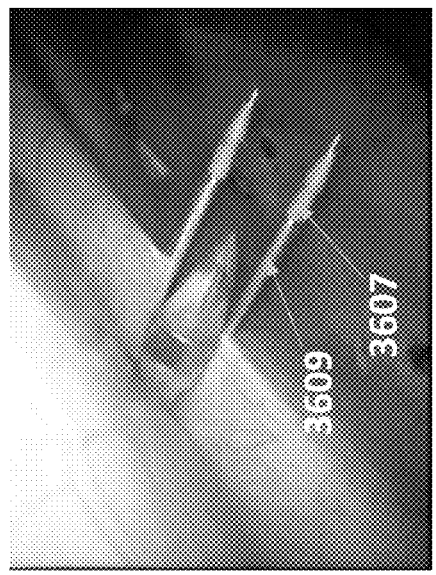
Figure 36A:
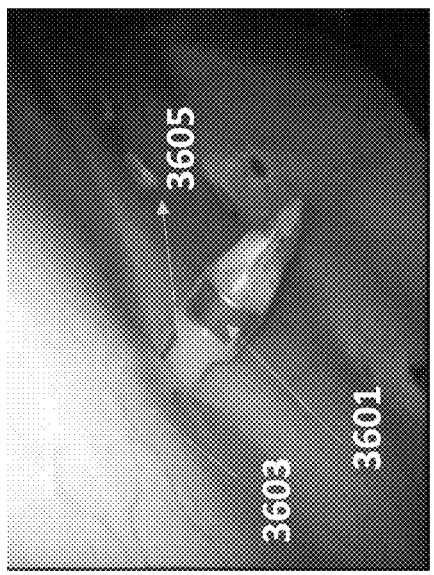

FIGS. 3A-K are a set of drawings showing an operating procedure of a trocar and external cannula assembly, according to some embodiments of the invention;

FIGS. 4A-B are a perspective view and a cross section view of a surface at a distal portion of a trocar comprising projections for enhancing contact with the tissue, according to some embodiments of the invention;

FIGS. 5A-B are side views of a distal portion of a trocar comprising an expandable leaflet structure, according to some embodiments of the invention;

FIGS. 6A-C are perspective views of a distal portion of an integrated trocar and external cannula assembly comprising a parallel anchor deployment mechanism, and an enlarged view of an anchor, according to some embodiments of the invention;

FIGS. 7A-B are side views of a distal portion of an integrated trocar and external cannula assembly comprising an arched anchor deployment mechanism, according to some embodiments of the invention;

FIGS. 8A-B are a side view and perspective view of a distal portion of an integrated trocar and external cannula assembly comprising a plurality of anchors, according to some embodiments of the invention;

FIGS. 9A-C are drawings of a trocar comprising a sleeve, and an enlarged perspective view and cross section view of the sleeve, according to some embodiments of the invention;

FIG. 10 is a drawing of a ratchet-based applicator for anchor deployment, according to some embodiments of the invention;

FIGS. 11A-B are drawings of a spring element coupled to thrusting elements for anchor deployment, and an enlarged view of a sliding element positioned on top of the spring, according to some embodiments of the invention;

FIG. 12 is a drawing of an external cannula comprising anchors, according to some embodiments of the invention;

FIG. 13 is a cross section view of a head portion of the external cannula, according to some embodiments of the invention;

FIG. 14 is a drawing of an integrated trocar and external cannula assembly, according to some embodiments of the invention;

FIGS. 15A-D are a set of drawings showing the anchor deployment procedure, according to some embodiments of the invention;

FIGS. 16A-C are cross section views showing actuation of a ratchet mechanism during pulling back of the anchor applicator, according to some embodiments of the invention;

FIGS. 17A-D are side views of a distal portion (A-B) and cross section views (C-D) of the device during activation of the anchor applicator for deploying anchors, according to some embodiments of the invention;

FIG. 18 is a cross section view of the device after anchors have been deployed into the tissue and before removal of the trocar from the external cannula, according to some embodiments of the invention;

FIGS. 19A-B are drawings showing removal of the trocar from the external cannula (A) and a cross section of the device during removal (B), according to some embodiments of the invention;

FIG. 20 is a flowchart of a method for anchor deployment using a wound closure device, according to some embodiments of the invention;

FIGS. 21A-H are a set of drawings showing an operating procedure of a wound closure device, according to some embodiments of the invention;

FIG. 22 shows an exemplary geometry of a distal portion of a trocar, according to some embodiments of the invention;

FIG. 23 shows an exemplary geometry of a surface configured below a narrow portion of a trocar shaft, according to some embodiments of the invention;

FIGS. 24A-E are a set of drawings showing an operating procedure of an anchorless obturator for wound closure, according to some embodiments of the invention;

FIGS. 25A-D show a distal portion of a trocar structured to provide a tissue folding effect (25A, 25B), and an illustration of the penetration points of the anchors in the tissue obtained by using the tissue folding effect (25C,25D), according to some embodiments of the invention;

FIGS. 26A-I illustrate an anchor deployment procedure involving a tissue folding effect, and an exemplary structure and operating mechanism of a trocar and external cannula assembly, according to some embodiments of the invention;

FIGS. 27A-B show an exemplary handle and sliding element of a trocar, according to some embodiments of the invention;

FIGS. 28A-I are various anchor designs, according to some embodiments of the invention;

FIGS. 29A-F illustrate a dove tail coupling between the external cannula and the anchors (A-C), and an exemplary alignment configuration between a trocar and an external cannula (D-F), according to some embodiments of the invention;

FIGS. 30A-C show a proximally facing cutting element of a trocar, according to some embodiments of the invention;

FIGS. 31A-E illustrate an exemplary anchor deployment procedure in which a proximally facing cutting element interacts with an anchor to penetrate the tissue, according to some embodiments of the invention;

FIGS. 32A-D illustrate an anchor thrusting element configured for deploying an anchor at a distance from the trocar shaft, according to some embodiments of the invention;

FIGS. 33A-E show a trocar comprising a set of rotatable wings configured for extending radially outward with respect to the trocar shaft, according to some embodiments of the invention;

FIGS. 34A-E show a trocar comprising an axially extendible and compressible structure, according to some embodiments of the invention;

FIGS. 35A-E are an isometric and cross sectional views (A-B), respectively, of an external cannula comprising anchors, and an exemplary configuration of an external cannula comprising suture reels (C-E), according to some embodiments of the invention;

FIGS. 36A-B are photos of an in vivo experiment performed in a porcine model using a trocar and external cannula assembly, according to some embodiments of the invention;

FIGS. 37A-F are photos of another in vivo experiment performed in a porcine model, using a trocar and external cannula assembly, according to some embodiments of the invention; and FIGS. 38A-C are an exemplary configuration of a trocar received within an external cannula, wherein the trocar shaft does not comprise a narrow portion, according to some embodiments of the invention.

DESCRIPTION OF SPECIFIC EMBODIMENTS OF THE INVENTION

The present invention, in some embodiments thereof, relates to a trocar, and, more particularly, but not exclusively, to a trocar and external cannula assembly for use in a laparoscopic procedure.

Some embodiments of the invention relate to an integrated trocar and wound closure device, comprising a trocar and an external cannula assembly. Some embodiments of the invention relate to a wound closure device comprising an obturator, optionally positionable within an external cannula.

A broad aspect of some embodiments of the invention relates to deployment of anchors and/or sutures into a tissue, for example into the fascia tissue of an abdominal wall, for closing a wound.

An aspect of some embodiments relates to a trocar shaft comprising a narrowing in proximity to a distal end of the trocar. In some embodiments, as the trocar is inserted into the abdominal wall, the narrow portion is positioned in the fascia tissue layer. In some embodiments, the narrowing is narrow enough to allow fascia tissue to spring back around it. Optionally, the narrowing is formed one or more recesses along the shaft that can be filled, at least in part, with fascia tissue. In some embodiments, tissue is actively forced to fill the recess defined by the narrow portion.

In some embodiments, a cross sectional area of the narrowing is smaller than a cross sectional area of shaft portions defined above and/or below the narrowing, for example 30% smaller, 50% smaller, 70% smaller, or intermediate, higher or lower percentage smaller. As referred to herein, a cross sectional area may refer to a summed area, for example if the shaft comprises holes or other lumens.

In some embodiments, a periphery of the narrow portion is smaller than a periphery of shaft portions configured above and/or below the narrow portion. Optionally, the periphery of the narrow portion is small enough so that fascia enters one or more voids defined by the narrow portion. In some embodiments, a circumscribing shape of the narrow portion, for example a circumscribed circle, comprises a shorter perimeter than a perimeter of a circumscribing shape of the shaft portions configured above and/or below the narrow portion.

In some embodiments, the narrow portion is defined by one or more recesses. Optionally, the one or more recess are configured circumferentially along the walls of the shaft, forming concavities along at least a portion of the shaft, for example on opposite facing walls of the shaft. In some embodiments, a recess is initiated at a certain distance from a longitudinal axis running along the center of the shaft, for example a distance of 0.5 mm, 1 mm, 1.5 mm, 3 mm, 5 mm, or any intermediate, larger or smaller distances. In some embodiments, a depth of the recess in the radial direction (i.e. towards the longitudinal axis of the shaft) is deep enough to receive at least a portion of the fascia tissue that springs back around the shaft, for example having a depth of 1 mm, 2 mm, 3 mm, 4 mm, or any smaller, intermediate or higher depths. In some embodiments, a geometry of the recess is configured such as to fit a relatively flat or straight piece of fascia entering the recess. In some embodiments, a recess is dimensioned such as to fill an effective diameter of the shaft, such as a diameter of portions of the shaft configured above and/or below the narrow portion. Optionally, for example if the shaft is not cylindrical, the recess is dimensioned to fill an effective outline configuration of the shaft.

In some embodiments, the narrowing is narrow enough to cause the trocar to be stabilized in the abdominal wall by the fascia.

In some embodiments, surfaces defined by the narrowing, such as shaft surfaces above or below the narrowing that face the narrowing, provide sensible feedback to a user. Optionally, feedback is provided due to resistance of the surface abutting against the fascia.

In some embodiments, a length of the narrow portion is long enough to allow a fascia having a certain thickness, such as 0.5 mm, 1 mm, 3, mm, 5 mm, 1 cm, 2 cm, or intermediate, larger or smaller thickness to at least partially enter one or more voids defined by the narrow portion. In some embodiments, a length of the narrow portion ranges between 0.1-20 mm, 0.1-40 mm, for example ranging between 0.1-5 mm, 6-10 mm, 0.2-0.4 mm, 4-7 mm, 1-3 mm, or intermediate, higher or lower ranges. In some embodiments, a length of the narrow portion of the shaft is long enough to cause an anchor delivered from a shaft portion above and/or below the narrow portion, or from an external cannula, to be deployed at the fascia layer. Optionally, by being positioned within the fascia tissue layer, the narrow portion defines a location of anchor deployment. Optionally, by controlling the positioning of the trocar, a user may control the location of anchor deployment, for example ensure that the anchors penetrate or partially penetrate through the fascia. Optionally, a distance between deployed anchors is controlled, for example a distance between two oppositely deployed anchors.

In some embodiments, for example if the shaft has a circular profile, a diameter of the narrow portion of the shaft is at least 50% smaller than a diameter of portions of the trocar shaft configured above and/or below the narrow portion. In some embodiments, an aperture (i.e. wound) formed in the tissue, for example by incising and optionally expanding the aperture, is sized such that the fascia springs back around the narrow portion. Optionally, the aperture is expanded upon insertion of the wider portions of the shaft, such as portions above and/or below the narrow portion, and when the narrow portion is positioned at the fascia, the tissue bordering the aperture elastically springs back, thereby returning or partially returning back to the originally sized aperture. Optionally, spring back of the tissue stabilizes the trocar in position. As spring back of the tissue is associated with the elasticity of the tissue, the extent of spring back may vary, for example, between patients. Optionally, the narrow portion is narrow enough so that even in patients in which the extent of spring-back of the tissue is relatively low, at least some spring back occurs. Additionally or alternatively, the proximally facing surface below the narrow portion engages the tissue in a way that even if spring back does not occur or only slightly occurs, the trocar is stabilized in position by the proximally facing surface clinging onto the tissue.

In some embodiments, the shaft surfaces defined by the narrow portion, which face the narrow portion, resist removal of the fascia tissue from the narrow portion. Optionally, by positioning the trocar such that the fascia surrounds the narrow portion, a user faces increasing resistance upon pulling or pushing the trocar, the resistance caused by the surfaces abutting against the fascia.

In some embodiments, resistance is provided by the proximal facing surface of the trocar shaft below the narrow portion. In some embodiments, the proximally facing surface comprises a tissue engaging geometry which is effective to reduce or prevent movement of tissue received within the recess, such as radially outward movement of tissue, away from the recess. In some embodiments, contact between the proximal facing shaft surface and a surface of the fascia facing the abdominal direction is enhanced by friction, for example by the shaft's surface being textured, such as having a discrete or continuous pattern, for example a wavy surface pattern or any other type of pattern suitable for enhancing friction.

In some embodiments, the proximal facing shaft surface is adapted for at least partially entering the fascia tissue, for example by having one or more projections pointed towards the fascia tissue. Optionally, the projections prick into the fascia layer, and may also prick and/or pass through peritoneum adjacent the fascia. In some embodiments, unwanted withdrawal of the trocar from the abdomen is prevented due to resistive force caused by the proximal facing surface of the shaft being held against the fascia tissue. In some embodiments, the proximal facing surface of the shaft comprises a relatively flat geometry, for example for providing increased resistance upon pulling of the trocar in the proximal direction. Alternatively, the proximal facing surface is angled, slanted, hemi-spherical shaped or otherwise shaped.

In some embodiments, the trocar geometry indicates a current positioning of the trocar within the tissue. For example, in some embodiments, a user such as a surgeon can sense a current insertion depth of the trocar by encountering resistive force, formed as the wider shaft portions above and below the narrow portion are pushed through the wound. This may provide an advantage in cases where insertion of the trocar is performed blindly (i.e. in cases where a surgeon is not able to visually identify tissue layers, directly and/or using an imaging device).

In some embodiments, the trocar's shaft comprises a distal end portion, followed by a narrower portion. Optionally, the joint or point of change between the distal end portion and the narrow portion defines a surface configured for abutting against the fascia. Optionally, the narrow portion is followed, in the proximal direction, by an element configured for resisting movement of trocar deeper in the abdominal direction. Optionally, the resisting element is a widening or wider portion of the shaft. Optionally, the resisting element provides a sensible indication to a user about the current positioning of the trocar, for example with respect to the fascia.

An aspect of some embodiments relates to a trocar and external cannula assembly comprising anchor thrusting elements for anchor deployment. In some embodiments, an anchor thrusting element is an element shaped and/or sized and/or positioned at a configuration suitable for engaging an anchor, to advance the anchor towards the tissue and/or into the tissue. In some embodiments, the anchor thrusting elements are retractable, manually and/or automatically, for example by utilizing a spring assembly which retracts the thrusting elements once the anchors are positioned at the fascia tissue, for example positioned under the fascia layer. In some embodiments, the anchor thrusting elements are configured in parallel to a longitudinal axis of the trocar shaft. Alternatively, the anchor thrusting elements are arched around the trocar shaft, to deploy anchors at an angle to a longitudinal axis of the trocar shaft, optionally increasing a distance between the deployed anchors. It is noted that in some embodiments, the anchor thrusting element does not necessarily "thrust" the anchor towards the tissue, but rather only engages the anchor and/or advances it.

In some embodiments, the trocar is used with a plurality of external cannulas, for closing multiple wounds for example by inserting a single trocar each time to a different external cannula located at an abdominal port, and deploying anchors to close the wound at each port.

An aspect of some embodiments relates to a trocar and external cannula assembly configured for deploying anchors at a distance from each other by forming a tissue fold which temporarily approximates the penetration points in the tissue. In some embodiments, the tissue fold effect provides for advancing anchors substantially in parallel to the trocar shaft, yet deploying anchors at a distance from the trocar shaft and/or at a distance from each other.

In some embodiments, tissue is crimped to a substantial upside down U shape. Optionally, the tissue is penetrated at opposing bases of the upside down U shape, for example by the anchors. In some embodiments, tissue is crimped between the narrow portion of the trocar and an anchor and/or between the narrow portion of the trocar and an anchor thrusting element. Optionally, prior to penetration, advancement of the anchor in a distal direction pushes the tissue against the narrow portion, forming the tissue fold. Optionally, the tissue fold is symmetrically formed on opposing sides of the trocar shaft by advancement of opposite anchors. In some embodiments, at least a portion of the trocar shaft is configured at the center of the upside down U shape, potentially preventing an anchor from penetrating through to the opposite side of the fold.

Additionally or alternatively to crimping tissue between the anchors and/or anchor thrusting element and the narrow portion, a proximal shaft portion of the trocar may comprise one or more extensions aligned at least in part with the narrow portion, allowing tissue to be crimped between the shaft extension and the narrow portion.

An aspect of some embodiments relates to a spring-actuated trocar external cannula assembly, in which anchor deployment is not resisted by the spring. A potential advantage of advancing the anchors into the tissue without encountering resistance of the spring may include providing increased sensing and/or control to a user such as physician operating the trocar, as the resistance felt by the user is solely the resistance of the tissue, as opposed to a combined resistance of the tissue and the spring.

In some embodiments, the spring is positioned to provide a "snap-back" mechanism which automatically retracts the anchor thrusting elements in a proximal direction, leaving the anchors deployed in the tissue.

An aspect of some embodiments relates to a trocar and external cannula assembly comprising a maximal diameter (e.g. a diameter of the external cannula which surrounds the trocar shaft) which is less than, for example, 30 mm, 20 mm, 40 mm, or intermediate, larger or smaller diameters. In some embodiments, a plurality of components of the device are coupled to each other in an arrangement which maintains all components within the limits of the maximal diameter. In some embodiments, components of the device are configured to fit one within the other, for example a sliding element of the trocar is at least partially received within a lumen of a handle of the trocar. In another example, the external cannula comprises one or more recesses shaped and/or sized to receive at least a portion of an anchor. Optionally, the recess defines a dovetail coupling between the anchor and the external cannula.

An aspect of some embodiments relates to a trocar comprising one or more proximally facing elements, configured to interact with the anchor to assist the anchor in penetrating the tissue. In some embodiments, the proximally facing element contacts the tissue from a substantially opposite direction to the anchor. In some embodiments, the proximally facing element comprises a cutting edge and/or tip suitable for cutting tissue, for example upon advancement of the anchor past the edge of the proximally facing element. In some embodiments, tissue trapped in between the cutting element and the anchor is cut in a scissor-like effect as the anchor is advanced past the cutting edge. Additionally or alternatively, a cutting tip of the element is configured to pierce the tissue. Additionally or alternatively, a cutting tip of the element is configured to punch a hole in the tissue.

An aspect of some embodiments relates to a trocar and external cannula assembly in which the external cannula comprises anchors and/or sutures and the trocar comprises a mechanism for engaging the anchors to deploy them in the tissue. In some embodiments, a coupling between the anchors and the external cannula provides for insertion of the trocar into the cannula, for example to obtain a "ready to use" configuration of the assembly, without causing unwanted advancement of the anchors distally (e.g. advancement of the anchors before a distal portion of the device has been introduced through the fascia). In some embodiments, the anchors are fixed in position relative to the external cannula by a dovetail coupling, until being engaged by anchor thrusting elements which extend externally from the trocar shaft during operation to contact the anchors and advance them into the tissue. A potential advantage of an anchor advancing mechanism which is separated from the anchors in the external cannula may include the ability to re-use a trocar with a plurality of external cannulas (e.g. by introducing the trocar each time into a different cannula). This may be especially advantageous in procedures in which a plurality of ports are created in the abdomen and a plurality of external cannulas are positioned in the ports to allow passing of a laparoscope through. Another potential advantage of the trocar comprising an integrated anchor advancing mechanism may include an external cannula having a simple, cost-efficient structure, for example relative to an external cannula in which at least a part of the anchor advancing mechanism is an integrated in the cannula itself. Another potential advantage of a trocar comprising an integrated anchor advancing mechanism which is configured to engage anchors and/or sutures that are coupled to an external cannula may include an assembly comprising dimensions (e.g. total diameter, length) that do not exceed those of a standard trocar and cannula assembly, except that the trocar and cannula assembly according to some embodiments of the invention already includes the anchor and/or suture deployment mechanism integrated within the assembly. Optionally, by having all components of the deployment mechanism such as the anchor thrusting elements, anchors, sliding element which actuates advancement, and/or other elements within the boundaries of the assembly (e.g. without having components protruding radially outwards from the cannula), a periphery of the assembly comprises a smooth, rounded profile which may be effective to reduce tearing of the tissue, such as during penetration, and enable insertion of the assembly through a relatively small wound.

A potential advantage of deploying anchors and/or sutures using a trocar and/or trocar and external cannula assembly for example as described herein may include deploying the anchors and/or sutures at a predefined, limited depth in the tissue. Another potential advantage may include deploying the anchors and/or sutures while the trocar is retained in a stable position by the fascia tissue which surrounds the narrow portion, thereby reducing a risk of deploying the anchors at a non-desired position relative to the device. Another potential advantage may include continuous control over the anchor and/or suture deployment process by movement of the handle, which in turn is effective to advance the anchor thrusting elements towards the tissue. Another potential advantage of a deployment mechanism for example as described herein may include a mechanism based on linear, axial movement of components, potentially simplifying operation by a user.

The term "trocar", as referred to in some embodiments of the invention, may refer to a surgical instrument adapted for insertion through the abdominal wall. In some embodiments, the instrument comprises a sharp distal tip, for example for incising through the tissue and/or expanding a wound. Alternatively, the instrument comprises a blunt tip. Optionally, the instrument comprises a shielded sharp tip. In some embodiments, the instrument is insertable into a cannula. In some embodiments, the instrument is configured to engage anchors and/or sutures that are comprised within the external cannula to deploy them.

The term "trocar and external cannula assembly", as referred to in some embodiments of the invention, may refer to a trocar positioned within an external cannula. In some embodiments, the trocar and external cannula assembly comprises an integrated anchor deployment mechanism. It is noted that the term "assembly" may refer to one or both components of the assembly.

The term "obturator", as referred to in some embodiments of the invention, may refer to a surgical instrument adapted for insertion through the abdominal wall, for providing wound closure. Optionally, the instrument is inserted through an existing wound. In some embodiments, the instrument comprises anchors and/or sutures for deploying in the tissue. In some embodiments, the instrument is insertable through an external cannula. Optionally, in embodiments in which the obturator itself comprises anchors and/or sutures, the external cannula does not comprise anchor and/or sutures. In some embodiments, the instrument comprises a blunt tip.

The term "fascia layer", as referred to in some embodiments of the invention, may refer to one or more of fascia tissue, peritoneum tissue adjacent the fascia, fat layer adjacent the fascia, fat layer between the peritoneum and fascia, and/or any other combination of abdominal tissue.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Before explaining at least one embodiment of the invention in detail, it is to be understood that any description related to a trocar, as referred to herein, may also be applicable to a closure device, as referred to herein, or vice versa.

A General Description of a Distal Portion of a Trocar

Figure 1:
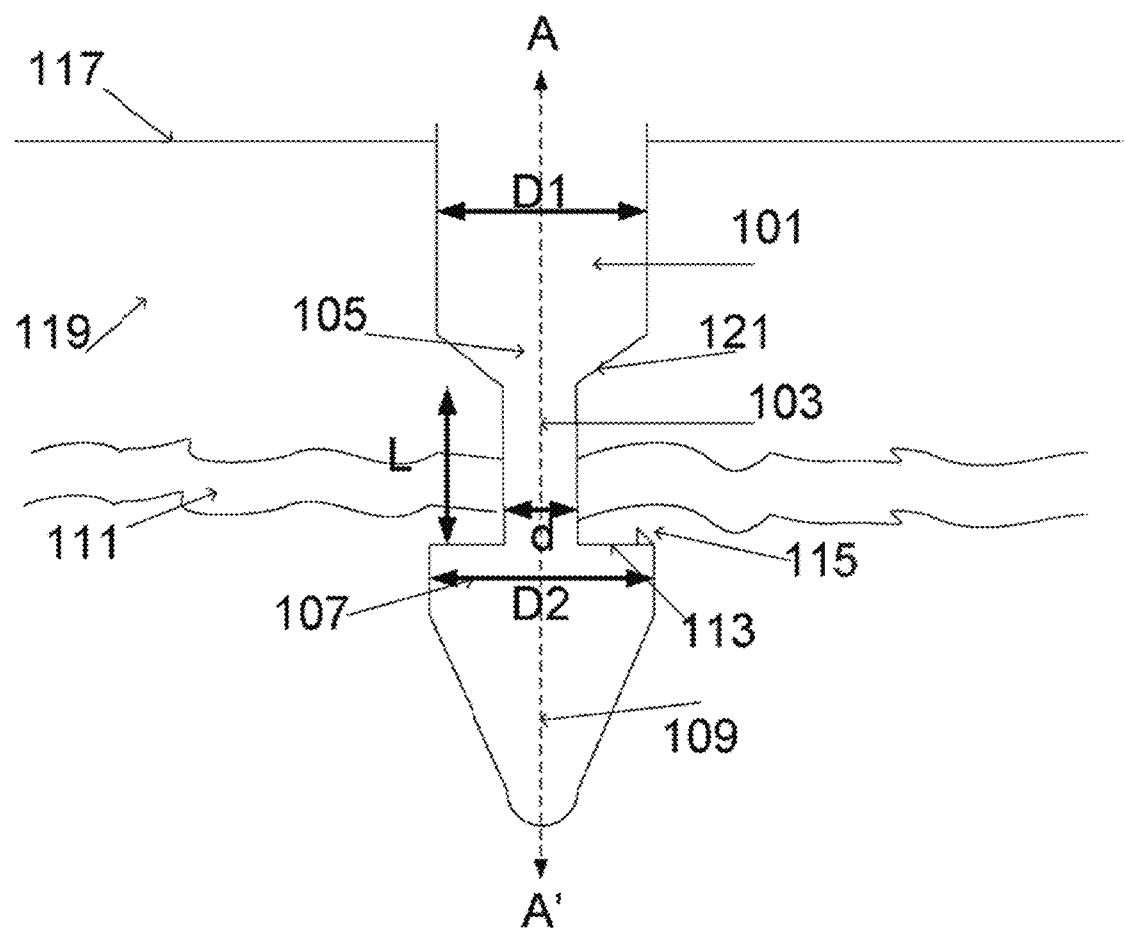
FIG. 1 is a drawing of a distal portion of a trocar, according to some embodiments of the invention.

Referring now to the drawings, FIG. 1 illustrates a distal portion of a trocar, according to some embodiments of the invention.

In some embodiments, the trocar comprises a shaft 101. In some embodiments, shaft 101 comprises at least one portion 103 that is narrower than portions of the shaft defined above and/or below the narrow portion, such as portion 105 and 107. In some embodiments, a cross sectional area of the narrow portion 103 is smaller than a cross sectional area of shaft portions 105 and/or 107, for example 30% smaller, 50% smaller, 60% smaller, 70% smaller, or intermediate, larger or smaller percentages smaller.

In some embodiments, shaft 101 is cylindrical. Optionally, narrow portion 103 has a diameter shorter than a diameter of portions of shaft defined by the narrow portion, such as portion 105 and portion 107.

Additionally or alternatively, in some embodiments, shaft 101 comprises one or more recesses which form the narrow portion. Optionally, the recesses are dimensioned for receiving fascia tissue. In some embodiments, the recesses are defined circumferentially around the shaft. Alternatively, the recesses are defined along portions of the shaft, for example encompassing 180 degrees, 270 degrees, or intermediate, larger or smaller portions of the shaft circumference. For example, two recesses may be configured along opposite facing walls of the shaft.

In some embodiments, a recess is initiated at a certain distance from a longitudinal axis AA' running along the center of the shaft, for example a distance of 0.5 mm, 1 mm, 1.5 mm, 3 mm or intermediate, longer or shorter distances. In some embodiments, a depth of the recess in the radial direction (i.e. towards the longitudinal axis of the shaft) is deep enough to receive at least a portion of the fascia tissue that springs back around the shaft, for example having a depth of 1 mm, 2 mm, 3 mm, 5 mm or any smaller, intermediate or higher depths. Optionally, a depth of the recess is determined so as to narrow a portion of the shaft for enabling fascia to spring back around it, yet leave enough distance from axis AA' to the initiation of the recess so that the formed narrow portion remains rigid enough, for example for transforming force from a proximal end to a distal end of the trocar.

In some embodiments, a geometry of the recess is configured such as to fit a relatively flat or straight piece of fascia entering the recess. In some embodiments, the narrow portion is proximal to a distal tip 109 of the trocar. For example, a distance between proximal facing surface 113 of shaft defined by the narrow portion and the end of distal tip 109 ranges between 5-50 mm, such as 15 mm, 30 mm, 45 mm.

In some embodiments, the walls of shaft portion 105 above the narrow portion are slanted, for example as shown at 121, thereby forming a tapered portion. Optionally, the walls are slanted at an angle of, for example, 20-80 degrees, such as 30 degrees, 60 degrees, 70 degrees with respect to a longitudinal axis of the trocar shaft. The slanted walls may facilitate insertion of the trocar into the abdominal wall.

In some embodiments, distal tip 109 is tapered. In some embodiments, distal tip 109 is a sharp tip, configured for puncturing a wound through an abdominal wall. Alternatively, tip 109 is a blunt tip, which can be inserted through an existing wound or port in the abdominal wall. In some embodiments, an aperture of the wound is sized according to a diameter of shaft 101, for example having a diameter similar to that of shaft portions 105 and/or 107. Optionally, an initial incision is expanded by the trocar shaft, and therefore the size of the aperture depends on the cross section of the trocar shaft. In some embodiments, the wound aperture comprises at least one diameter of at least 3 mm, such as 4 mm, 5 mm, 6 mm, 8 mm or intermediate, larger or smaller diameters. Alternatively, the profile of the aperture is not circular, for example being elliptical, rectangular or otherwise shaped. Optionally, the aperture comprises an arbitrary shaped profile.

In some embodiments, at least a portion of the trocar is inserted through an abdominal wall, for example through skin 117, and/or through a layer of fat 119, and/or through a fascia tissue layer 111.

In some embodiments, the proximal facing surface 113 of shaft portion 107, which upon insertion of the trocar abuts against the fascia tissue, for example abuts against an internal face of fascia layer 111, comprises at least one projection 115. Optionally, projection 115 slightly protrudes into the fascia tissue layer.

In some embodiments, a diameter d of narrow portion 103 is smaller than, for example, a diameter D1 of portion 105 of the shaft. In some embodiments, a diameter d of narrow portion 103 is smaller than, for example, a diameter D2 of portion 107 of the shaft. Optionally, diameter d is smaller than diameter D1 and/or diameter D2 by, for example, 50%, 60%, 70%, 80%, and/or intermediate, larger or smaller percentages. A diameter D1 may be determined according to a diameter of an external cannula through which the trocar is inserted, and may range between, for example, 12-20 mm, In some embodiments, diameter d ranges between, for example, 2-5 mm, for example 3 mm, 4 mm. In some embodiments, diameter D1 is equal to diameter D2. Alternatively, diameter D2 is smaller than diameter D1, for example 10%, 20%, or 40% smaller.

In some embodiments, diameter d is small enough so that upon insertion of the trocar into the abdominal wall, at least a portion of the tissue surrounding portion 103, bounces back around the trocar shaft. A potential advantage includes utilizing the natural elastic properties of the tissue for holding the trocar in position, and optionally for enabling anchor deployment at the fascia layer.

In some embodiments, a length L of narrow portion 103 ranges between, for example, 0.1-30 mm, such as 2 mm, 5 mm, 7 mm, 15 mm, 25 mm, or any intermediate, longer or shorter lengths. Various trocars may comprise narrow portions with different lengths. Optionally, a trocar having a certain narrow portion length is selected according to various parameters to be suited for the patient's needs, such as a size of an aperture in the tissue, a thickness of muscle layer, and/or the elasticity of the fascia layer. Optionally, one or more of the parameters described herein are correlated with the age of the treated patient.

In some embodiments, as portions 105 and/or 107 are forced through and/or are retracted from the wound, a user handling the device, for example a surgeon, encounters resistive force caused by pulling and/or pushing wider shaft portions 105 and/or 107 through the wound.

In some embodiments, an insertion depth of the trocar is defined by positioning narrow portion 103 such that it is surrounded by the fascia layer. Optionally, an insertion depth of the trocar determines a depth in which anchors are further deployed. Optionally, a depth of the deployed anchors is determined according to their range of movement. In some embodiments, the anchors are deployed at depth in which fascia wound closure does not cause damage to the underlying viscera. In some embodiments, the anchors are deployed at a depth that does not surpass tip 109. Alternatively, the anchors are deployed at a depth beyond tip 109 in the distal direction.

During insertion of the trocar, the trocar's geometry provides sensible feedback, enabling a user to deduce a current position (for example, current depth) of the trocar in the tissue at several stages during insertion. For example, a user senses less resistive force as narrow portion 103 passes through the fascia layer, since the narrow portion is pushed through an aperture that was formed by preceding portion 107, having a larger diameter than portion 103. If the trocar is further pushed into the tissue, wider portion 105 may again increase the resistive force sensed by the user when it reaches the aperture in fascia 111, indicating to the user that narrow portion 103 has been fully inserted through fascia 111. In another example, to complete the positioning of the trocar, a user may pull the trocar slightly back up, until encountering resistive force caused by surface 113 abutting against an internal face of fascia 111.

In some embodiments, a pulling force of up to 3 N, up to 10 N, up to 40 N, or any intermediate values can be applied without causing portion 107 to pass back up through fascia 111. Optionally, unwanted withdrawal of the trocar from the tissue is prevented.

A geometry providing positioning feedback which can be sensed by a user may provide an advantage in a situation in which insertion and positioning of the trocar is performed blindly. Another potential advantage may include controlling a positioning of the trocar, such as depth of insertion, even in patients having a relatively thick fat layer 119 between the skin 117 and the fascia 111.

In some embodiments, a geometry of surface 113 is configured to increase resistance to removal and/or movement of the trocar with respect to the fascia layer. In some embodiments, surface 113 is textured for increased friction, for example having a wavy surface or other surface pattern. In some embodiments, surface 113 is configured for clinging onto the fascia by comprising one or more projections 115. In some embodiments, projections 115 are arranged circumferentially. In some embodiments, projections 115 are arranged in an array configuration, and are distributed evenly on surface 113. In some embodiments, projections 115 are positioned only on a portion of surface 113, for example projections positioned on opposite portions of the surface, projections covering a quarter, a third, or a half of the donut-shaped surface 113, projections positioned on two symmetrical quarters of the surface, and/or other projection arrangements.

In some embodiments, at least a portion of trocar shaft 101 is rigid, for example for transferring pushing and/or pulling force applied to a proximal end of the shaft by a user. Additional or alternatively, shaft 101 comprises one or more flexible portions.

Figure 2:
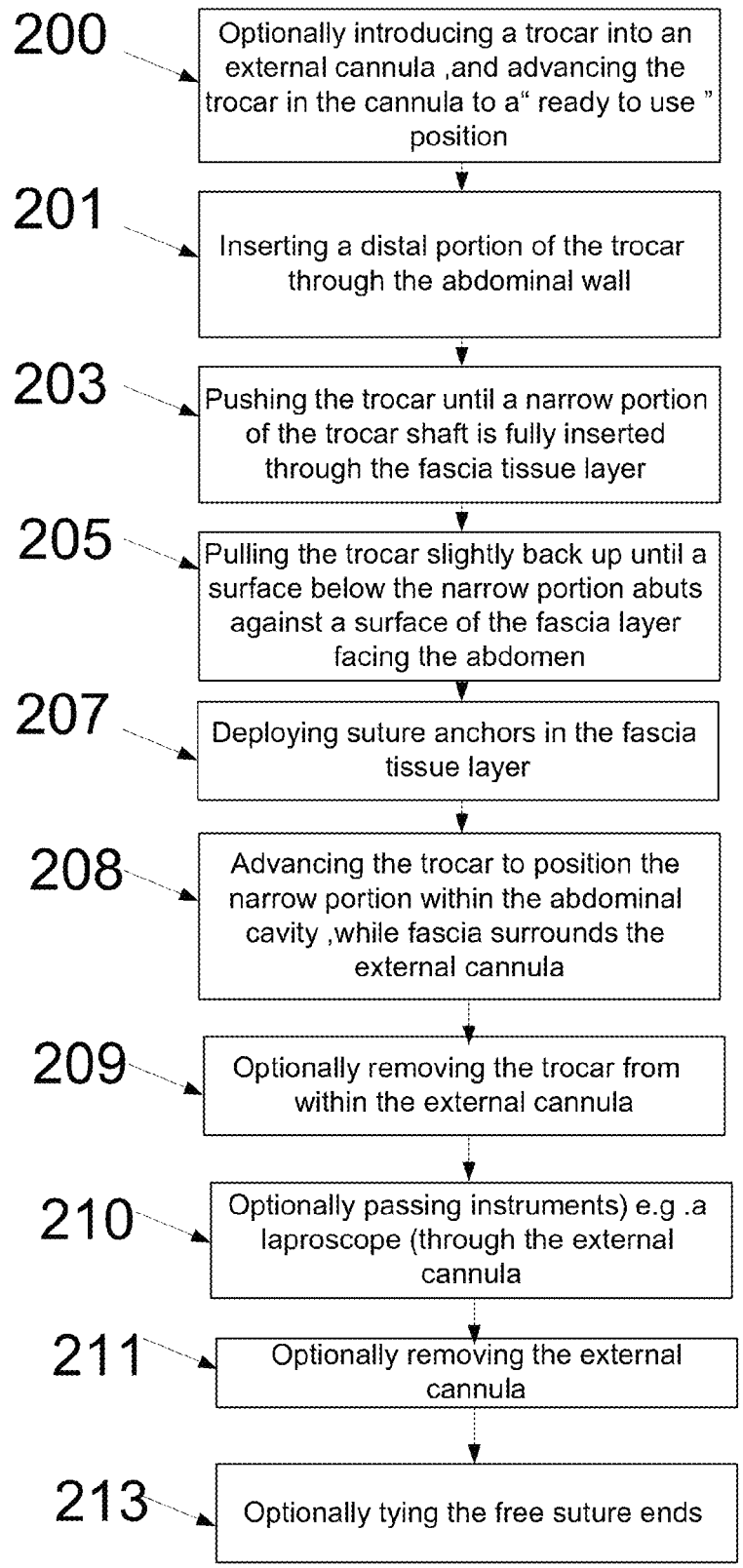
FIG. 2 is a flowchart of a method for inserting a trocar and external assembly into a tissue for anchor deployment, according to some embodiments of the invention.

An Exemplary Method for Inserting a Trocar and External Cannula Assembly into the Abdominal Wall FIG. 2 is a flowchart of a method for inserting a trocar and wound closure device into a tissue for anchor deployment, according to some embodiments of the invention.

In some embodiments, an assembly comprising a trocar and external cannula is pre-assembled, for example by introducing the trocar into the external cannula, and advancing the trocar to a "ready to use position" (200). Optionally, the "ready to use" position comprises a position in which the trocar is axially aligned with respect to the cannula at a configuration suitable for anchor deployment, e.g. a configuration in which anchor thrusting elements, for example as further described herein, are located right above the anchors (or, in some embodiments, even protruding into at least a proximal portion of the anchors) to allow deployment of the anchors into the tissue.

In some embodiments, a distal portion of the trocar is inserted into an abdomen (201). Optionally, a distal tip of the trocar forms a port in the abdominal wall, for example by comprising a blade. Alternatively, the distal portion of the trocar and/or external cannula is inserted through an existing port or incision.

In some embodiments, the trocar is pushed (e.g advanced relative to the external cannula) until a narrow portion of the trocar shaft has fully passed through the fascia tissue layer (203). Optionally, increased resistance felt by a user when a wider and/or widening portion of the trocar shaft reaches the wound in the fascia indicates that the narrow portion has been fully inserted.

In some embodiments, the trocar is slightly pulled back in an upright direction with respect to the abdomen (205). Optionally, a proximal facing surface of a wider portion of the shaft defined by the narrow portion is held up against an internal face of the fascia that faces towards the abdomen.

Optionally, the increased resistance formed when the surface is held back against the tissue indicates to a user that the trocar is positioned at a location (e.g. depth) suitable, for example, for anchor deployment. In some embodiments, anchors are deployed in the fascia tissue layer (207). Optionally, such positioning of the trocar ensures that anchors are deployed in the fascia layer, as opposed to, for example, a fat layer. Optionally, such positioning of the trocar ensures that a depth of the trocar, for example a depth of the trocar tip with respect to the skin, provides for anchor deployment in which the location of the anchors is defined regardless of a thickness of a fat layer between the fascia and the skin, or generally regardless of any distance between the fascia and the skin, which may range, for example, between 0-100 mm. The surface of the trocar shaft defined below the narrowing portion situates the trocar at a pre-defined location with respect to the fascia, even when abdominal walls of various thicknesses and/or anatomy are being treated.

In some embodiments, the suture anchors are delivered in parallel to the trocar shaft. Alternatively, the anchors are delivered at an angle to the trocar shaft. In some embodiments, a distance between the deployed anchors is equal to a diameter of the trocar shaft. Alternatively, a distance between the deployed anchors is larger than a diameter of the trocar shaft, for example if the anchors are delivered at an angle with respect the trocar shaft. Alternatively, in some embodiments, a distance between the deployed anchors is smaller than a diameter of the trocar shaft.

In some embodiments, once the anchors are deployed, the trocar is advanced distally such that the narrow portion is located within the abdominal cavity, while the external cannula is surrounded by fascia tissue (208).

In some embodiments, once the anchors are deployed, the trocar is optionally removed from within the external cannula (209). Optionally, the deployed anchors assist in fixating the external cannula at a certain position with respect to the tissue. Optionally, the deployed anchors stabilize the cannula. The external cannula may remain within the tissue after removal of the trocar, providing a port for insertion of a laparoscope or any other tool used during the procedure (210).

In some embodiments, for example at the end of the procedure, the external cannula is removed from the tissue (211). Optionally, the sutures that are attached to the anchors are tied to close a wound in the fascia tissue layer.

In some embodiments, insertion of the trocar and external cannula assembly complies with a commonly used insertion method referred to as "Hasson's technique", which includes dissecting through the abdomen until the fascia is identified, incising through the fascia to enter the peritoneal cavity, and positioning at least two sutures on both sides of the fascia wound to close it.

In some embodiments, a narrow portion of the assembly is defined by the external cannula with respect to the trocar, for example the trocar may not comprise a narrow portion (e.g. be formed as a uniform cylindrical shaft) and the external cannula can be positioned with respect to the trocar to define a narrow portion between them.

FIGS. 3A-K are a set of drawings showing an operating procedure of a trocar and external cannula assembly, according to some embodiments of the invention.

In some embodiments, the assembly comprises a trocar 301 (only a distal portion of the trocar is shown in this figure) and an external cannula 303.

In some embodiments, as seen for example in FIGS. 3A and 3B, a user, by gripping handle 305, pushes a distal portion of the trocar through the abdominal wall, for example through layers of skin 307, fat 309 and/or fascia tissue 311. Optionally, the trocar is pushed through a premade incision in the skin, for example formed by the surgeon using a scalpel. In some embodiments, the user rotates the trocar around its longitudinal axis during insertion, in a screw-like threading motion. Rotating the trocar may facilitate advancing it through the tissue layers.

In some embodiments, the assembly is pushed until a distal end of the external cannula 315 enters through fascia 311, for example protruding to a certain extent below fascia 311, such as to a distance of 10-80 mm below the fascia. In some embodiments, the assembly is pushed only until narrow portion 317 of the trocar shaft enters through fascia 311. Optionally, insertion of the assembly and/or one or both components of it (i.e. the trocar and/or the cannula) to the extent of the fascia layer can be achieved by sensible feedback provided by the narrow portion and/or surface below the narrow portion. Additionally or alternatively, insertion of the assembly to the extent of the fascia layer can be achieved by performing insertion under vision.

In some embodiments, for example to position the assembly for anchor deployment, the user slightly pulls the assembly in the proximal direction (away from the abdomen), as seen for example in FIGS. 3C and 3D. Optionally, the assembly is pulled until proximal facing surface 319 of trocar shaft portion 301 is held against fascia 311. Optionally, if surface 319 comprises projections (not shown in this figure), the pulling motion causes the projections to slightly penetrate through fascia 311, enhancing a contact between surface 319 and fascia 311.

In some embodiments, the user can verify the current depth of the trocar within the tissue, for example by increasing the pulling force so that the portion of fascia 311 which lies against surface 319, marked 321, is stretched in the proximal direction. Optionally, tissue 321 naturally springs back around narrow portion 317. Optionally, if surface 319 is textured and/or comprises projections (not shown in this figure) tissue 321 is maintained at the narrow portion, even when such an increased pulling force is applied. Optionally, the user senses increased resistance caused by stretched tissue portion 321, and discontinues pulling. Optionally, tissue 321 supports narrow portion 317, so that the assembly is stabilized in position.

In some embodiments, the assembly is configured for deploying anchors into the tissue. In some embodiments, anchors 323 are positioned along a distal portion of external cannula 315, as will be further elaborated. To begin the anchor deployment, in some embodiments, for example as seen in FIG. 3E, the user lifts up cap 325 of anchor applicator 327, pulling anchor applicator 327 up until it reaches a position in which it is adapted for forcing down anchor thrusting elements 331. To advance anchors 323 towards the tissue, for example as shown in FIG. 3F, the user pushes cap 325 back down in the abdominal direction, while simultaneously grasping the assembly and pulling in the proximal direction away from the abdomen. Optionally, fascia 311 is slightly stretched against surface 319. Anchors 323 are released below fascia 311, for example at a depth of 1-30 mm with respect to fascia 311, such as 2 mm, 5 mm, 15 mm, 25 mm. In some embodiments, during anchor deployment, the tips of the anchors do not extend beyond a distal tip of the trocar. Optionally, by limiting a depth of the deployed anchors, damage to the inner organs of the abdomen is prevented.

In some embodiments, anchors 323 comprise sutures 329, for example sutures that are threaded through holes in the anchors. Optionally, sutures 329 extend freely away from the external cannula once anchors 323 are released.

In some embodiments, for example as shown in FIG. 3G, anchor thrusting elements 331 return back up into the trocar's housing. Optionally, the anchor thrusting elements are pulled back automatically, for example by utilizing a spring mechanism, as will be further described.

In some embodiments, the user then pushes the assembly down in the abdominal direction (distal direction), for example as shown in FIG. 3H, for example to locate a distal end of external cannula 315 under the fascia layer, optionally penetrating through the peritoneum as well. Optionally, the user pushes until external cannula 315 is fully inserted along its length into the tissue.

In some embodiments, for example as shown in FIG. 3I, the user retracts the trocar from within external cannula 315. Optionally, anchors 323 are fully deployed at fascia 311. In some embodiments, a proximal end of sutures 329 remains attached to a proximal end of the external cannula, for example to cannula's proximal end. Alternatively, the proximal end of sutures 329 hangs freely. In some embodiments, sutures 329 extend externally to the cannula. Alternatively, sutures 329 extend within the cannula.

In some embodiments, deployed anchors 323 help stabilize the cannula in place, for example by having a suture extending between a proximal end of the cannula and an anchor deployed in the tissue.

In some embodiments, the port comprising external cannula 315 is used for passing tools into the abdomen, such as a laparoscope. Optionally, cannula 315 remains in the tissue until the end of the procedure.

In some embodiments, as shown for example in FIG. 3J, the external cannula is removed from the tissue. Optionally, upon removal, if the proximal ends of sutures 329 are attached to the cannula, the user separates the suture ends from the cannula, for example by pulling the suture ends to detach the sutures, or by cutting the suture ends. The deployed anchors 323 remain in the tissue. At this point, in some embodiments, the user grasps sutures 329 and ties them together, closing the wound 331 in fascia 311.

In some embodiments, a plurality of anchors such as 2, 3, 4, 6, or any intermediate or higher number are deployed in the tissue. In some embodiments, a single anchor comprises more than one threaded suture, such as 2, 3, 4 or higher number of sutures.

In some embodiments, at least a portion of the shaft of trocar 301 is hollow and is dimensioned for passing a tool through. Optionally, the assembly is configured for insertion into the tissue over a guide wire, passing within, for example, a lumen of the trocar's shaft.

In some embodiments, the trocar can be used separately from the external cannula. In some embodiments, the trocar can be inserted through any type of cannula, such as any previously known in the art cannula used for laparoscopic procedures. In some embodiments, the anchors and/or sutures are fixedly attached to the trocar, and not to the external cannula.

In some embodiments, for example when multiple ports are created in the tissue, a single trocar can be used with multiple external cannulas. An exemplary procedure includes inserting the trocar into an external cannula that has been previously positioned in the port, locking the trocar into the cannula in a configuration that allows anchor deployment, for example by positioning an anchor applicator above anchor thrusting elements, deploying the anchors from the external cannula into the tissue, retracting the trocar, and repeating the procedure at a second port comprising a different external cannula.

Alternatively, in some embodiments, the first cannula is assembled onto the trocar, for example as described above.

Various Embodiments of a Distal Portion of a Trocar

FIGS. 4A-B are a perspective view and a cross section of a distal portion of a trocar comprising projections for enhancing contact with the tissue, according to some embodiments of the invention.

In some embodiments, a proximal facing surface 401 of the trocar defined by the narrow portion 403 of the trocar shaft comprises one or more projections 405. Optionally, during positioning of the trocar, for example during the slight pull-back for positioning the trocar, projections 405 prick the layer of fascia facing the abdomen, and optionally anchor to the tissue to strengthen a contact between surface 401 and the fascia. Optionally, projections 405 assist in stabilizing the trocar.

In some embodiments, projections 405 are shaped as teeth, for example having a triangular profile, a conical profile, or other profiles. In some embodiments, a projection comprises a tapered end, facing the fascia layer. Alternatively, the tapered end faces the direction of surface 401. In some embodiments, projections 405 are distributed circumferentially, for example distributed along 10%, 30%, 60%, 80%, 100% or any intermediate, higher or lower percentages of a circumference of surface 401. In some embodiments projections 405 are distributed on different portions of surface 401, for example distributed around a base of narrow portion 403, distributed on a half of surface 401, on a quarter of surface 401, or on other sectors of the surface. In some embodiments, projections 405 cover at least 10%, at least 40%, at least 60%, at least 75% or intermediate, larger or smaller percentages of surface 401.

Additionally or alternatively, surface 401 is textured, for example being wavy and/or bumpy, for increasing friction between the shaft surface and the fascia.

In some embodiments, surface 401 is not planar, for example having a conical profile.

In some embodiments, distal tip 407 comprises a recess 11. In some embodiments, a blade, for example made of plastic or metal is positioned within the recess. In some embodiments, the blade is an integrated portion of the distal tip.

In some embodiments, the blade is configured for advancing through the abdominal wall layers, for example expanding the wound radially outwards, minimizing the tearing of tissue. Optionally, a plastic blade is preferable for such wound expansion.

In some embodiments, tip 407 is not adapted for cutting tissue, for example in a trocar suitable for use during a "Hasson technique" procedure. During such a procedure, a surgeon may cut the skin using a scalpel or any other cutting means. A trocar, in some embodiments, may comply with the "Hasson technique" by having a smooth and/or blunt distal tip, for example without any sharp edges, which may prevent the risk of damage to abdominal tissue or nearby organs.

In some embodiments, the blade is sharp enough for incising through the tissue. Optionally, the blade is made of metal. In some embodiments, shaft portion 409 comprises more than one recess 411, in which multiple cutting blades can be positioned. In some embodiments, the trocar comprises a mechanism such as a spring biased mechanism for preventing the cutting blades from protruding out of the recesses, unless force is applied, for example during insertion of the trocar. Optionally, this safety mechanism is designed to lock at least a portion of distal tip 407 against the blades, for example after one or more blades protrude from the tip, in a way that prevents additional protrusion of the one or more blades out of distal tip 407.

In some embodiments, shaft portions 409 and/or 413 (above narrow portion 403), comprise one or more recesses 415 alongside the shaft. In some embodiments, recess 415 extends longitudinally along portions 409 and 413, with a spacing or break formed at narrow portion 403. In some embodiments, recess 415 is dimensioned for receiving an anchor and/or an anchor thrusting element. Optionally, when the trocar is positioned within the external cannula, the anchor thrusting elements and/or the anchors are located in between an internal wall of the cannula and an external wall of the trocar. In some embodiments, recess 415 has a cylindrical concave surface, for example for receiving an anchor thrusting element shaped as a cylindrical rod.

In some embodiments, a distal end 417 of recess 415 is located above the distal end of the trocar, for example 5 mm, 2 mm, 6 mm, or intermediate, longer or shorter distances above the distal end of the trocar. Optionally, this configuration defines a depth in which anchors are deployed with respect to the fascia. Optionally, the anchors are deployed at a depth equal to length L measured between surface 401 and the distal end of the trocar. Alternatively, the anchors are deployed at depth shorter than length L, for example 10%, 30%, 40%, 50% shorter or intermediate, higher or lower percentages shorter. Alternatively, the anchors are deployed at a depth longer than length L, for example 10%, 30%, 40%, 80% longer or intermediate, higher or lower percentages longer. Optionally, anchor deployment at a depth longer than length L is achieved by pushing the anchor thrusting elements to an extent that surpasses the distal end of the trocar.

In some embodiments, a surface of shaft portion 413 opposite to surface 401 has a conical profile, for example as shown in FIG. 4B, for example to enable smooth insertion of the trocar through the tissue that bounced back, surrounding narrow portion 403. Optionally, the conical profile causes increasing resistance as the trocar is inserted into the tissue, providing a sensible indication to a user about the positioning of the trocar, for example indicating that the narrow portion in located at the fascia layer.

FIGS. 5A-B are side views of a distal portion of a trocar comprising an expandable leaflet structure, according to some embodiments of the invention.

In some embodiments, a surface of the trocar shaft defined below narrow portion 501 comprises an expandable structure, such as leaflet structure 503. In some embodiments, structure 503 comprises a plurality of leaflets 505. In some embodiments, the leaflets 505 are arranged circumferentially around the shaft's surface.

In some embodiments, a leaflet comprises two or more segments 507.

Optionally, the bonding between segments 507 is flexible, allowing a segment to bend with respect to the other. Alternatively, a leaflet comprises a single segment.

In some embodiments, a segment 507 of the leaflet has a thin, planar geometry, for example being shaped as a rectangle.

In some embodiments, the leaflet structure is adapted for two operational modes: a closed mode, shown in FIG. 5A, and an expanded mode, shown in FIG. 5B.

In some embodiments, in the closed mode, the leaflets are in an upright position. Optionally, in this mode, the leaflets do not extend beyond the trocar's perimeter. Optionally, during insertion of the trocar into the tissue, the leaflets are in the closed mode, so as to allow a smooth insertion of the trocar.

In some embodiments, upon the slight pull-back of the trocar, the leaflets are expanded. In some embodiments, in the expanded position, the leaflets are bended to form an angle between segments 507, for example a 30 degree, 50 degree, 80 degree, 90 degree or intermediate, larger or smaller angles. In some embodiments, in the expanded position, at least a portion of a leaflet 505 extends beyond a perimeter of the trocar. Optionally, the bend between the leaflets defines a relatively sharp edge 509, which may prick into the fascia.

In some embodiments, the leaflets are transformed from the closed mode to the open mode automatically, for example the leaflets are forced to bend by the face of the fascia upon pull back of the trocar. Alternatively, in some embodiments, a user can mechanically activate the expansion, for example by using a rod which is coupled to the leaflets, and can be pushed and/or pulled by a user to expand the leaflets.

In some embodiments, leaflet structure 503 prevents unwanted retraction of the trocar from the tissue, by leaning against the fascia and creating resistance in an opposite direction from the pulling direction.

In some embodiments, leaflet structure 403 is transformed from the open position to the closed position by means of a spring placed inside the distal tip of the trocar, for example for fully retracting the trocar from the tissue.

In some embodiments, a distal tip of the trocar 507 is blunt, for example being a ball-shaped tip.

It is to be noted that at least some of the structural features described herein, such as the expandable structure and/or the blunt tip, along with a narrow portion of the shaft, may be applicable to a wound closure device (e.g. an obturator for example as described herein), according to some embodiments of the invention.

FIGS. 6A-C are perspective views of a distal portion of a trocar and external cannula comprising a parallel anchor deployment mechanism, and an enlarged view of an anchor, according to some embodiments of the invention.

In some embodiments, one or more anchors 601 are positioned at a distal portion of the external cannula 603. In some embodiment, cannula 603 comprises a recess 605, in which the anchor is positioned. Optionally, the anchor is positioned in the recess such that it does not extend beyond a perimeter of the cannula. In some embodiments, an internal face of the anchor contacts a surface of the trocar shaft, for example a surface of a concave recess of the shaft.

In some embodiments, an anchor thrusting element 607 is used for advancing anchor 601 into the tissue. Optionally, in the insertion position, for example as shown in FIG. 6A, the anchor thrusting element is located above anchor 601 between the trocar shaft and the external cannula, and cannot be observed from the outside.

In some embodiments, during anchor deployment, anchor thrusting element 607 is pushed forward. Optionally, a distal end of element 607 is pushed into a lumen 609 of the anchor. In some embodiments, anchor thrusting element 607 is shaped as a cylindrical rod. Optionally, lumen 609 is dimensioned to receive element 607, for example having a cylindrical profile as well.

In some embodiments, one or more anchors 601 are deployed into the tissue. Optionally, the anchors are deployed in parallel to the longitudinal axis of the trocar. Optionally, the anchors are deployed at a horizontal distance of 3 to 10 mm such as 4 mm, 6 mm, 8 mm from the trocar distal tip. Optionally, a distance 611 between the tips of the deployed anchors, such as oppositely deployed anchors, ranges between 6 to 20 mm, such as 8 mm, 12 mm, 16 mm.

In some embodiments, an anchor 601, for example as shown in FIG. 6C, comprises a tapered end, for penetrating through the tissue. In some embodiments, anchor 601 comprises one, two, or a plurality of holes 615 for threading a suture. Optionally, threading the suture through the holes prevents undesired knots in the suture.

In some embodiments, anchor 601 comprises a blunt end, for example a rounded end. Optionally, lumen 609 extends between opposite ends of the anchor. In some embodiments, lumen 609 is dimensioned to receive anchor thrusting element 607 in a way that a distal end of element 607 passes beyond the distal end of the anchor. Optionally, for example in a configuration as described, a distal end of thrusting element 607 is tapered, for penetrating through the tissue ahead of anchor 601.

In some embodiments, additionally or alternatively to passing within a lumen of the anchor, a tapered thrusting element is configured to slide alongside an anchor. In some embodiments, the tapered thrusting element is configured as a tube that surrounds an anchor. Optionally, a distal end of the tube penetrates the tissue ahead of the anchor that is positioned within the lumen of the tube.

In some embodiments, anchor 601 is made of a hard material, such as titanium or plastic. In some embodiments, anchor 601 is made of a material adapted for being absorbed in tissue over time, for example Glycolide (PGA) so that it does not need to be removed from the tissue once the sutures are tied and the wound has been closed. In some embodiments, the sutures are made of a material adapted for dissolving the tissue over time, for example Glycolide (PGA).

FIGS. 7A-B are side views of a distal portion of a trocar comprising an arched anchor deployment mechanism, according to some embodiments of the invention.

FIG. 7B illustrates an embodiment where anchors 701 are deployed at an angle to trocar shaft 703. In some embodiments, an anchor thrusting element 705 is wound around shaft 703, between the shaft and the external cannula 707. Optionally, shaft 703 and/or cannula 707 comprise an arched concave recess, for leading thrusting element 705 in a winding pattern. Optionally, the thrusting elements are winded along a portion of the shaft. Optionally, the thrusting elements are configured in parallel to the shaft, alongside a portion of the shaft. Optionally, the thrusting elements are winded along one portion of the shaft, and configured in parallel alongside a different portion of the shaft. Optionally, the arched configuration of element pushes anchor 701 away from shaft 703, so that an angle α of, for example, 10 degrees, 30 degrees, 60 degrees is formed between anchor 701 and shaft 703, for example with respect to a longitudinal axis of the shaft.

In some embodiment, the arched anchor deployment mechanism increases a distance between the deployed anchors.

FIGS. 8A-B are a side view and perspective view of a distal portion of a trocar and external cannula comprising a plurality of anchors, according to some embodiments of the invention.

In some embodiments, the assembly comprises a plurality of anchors 801, such as 2, 4, 6, 7, 8, 9, 12 anchors or any intermediate or higher number of anchors. In some embodiments, each anchor is pushed by a corresponding anchor thrusting element 803. Alternatively, an anchor thrusting element is configured for pushing more than one anchor, for example by having a split end.

In some embodiments, the plurality of anchors are deployed together, for example to enable wound closure with multiple suture ties. Alternatively, a portion of the anchors, such as 2 anchors, are deployed at a first port location, and a portion of the anchors are deployed at a second port location, etc.

A Description of Various Components of a Trocar and External Cannula Assembly

FIGS. 9A-C are a drawing of a trocar comprising a sleeve, and an enlarged perspective view and cross section view of the sleeve, according to some embodiments of the invention.

In some embodiments, a trocar 901 comprises a sleeve 903. In some embodiments, sleeve 903 is threaded over a portion of the trocar shaft, for example covering a narrowing portion of the shaft and/or shaft portions located above and below the narrow portion.

In some embodiments, sleeve 903 enables insertion and/or retraction of trocar 901 from an external cannula (not shown in this figure), for example by changing a location of the sleeve along the trocar at various stages of the insertion and retraction procedure.

In some embodiments, sleeve 903 is configured for spatially orientating trocar 901 to a position inside the external cannula. In some embodiments, sleeve 903 comprises extensions 905 that extend outwardly from the trocar, for aligning the trocar with respect to the external cannula.

In some embodiments, sleeve 903 comprises extensions 907 that extend inwardly, for aligning a distal end of the anchor thrusting element during insertion of the trocar into the external cannula.

In some embodiments, sleeve 903 is adapted for sealing spaces between trocar 901 and the external cannula, for example for preventing air and/or gas such as $CO_2$ which is commonly used during laparoscopy procedures to escape from the abdomen.

In some embodiments, sleeve 903 comprises a tooth element 909. In some embodiments, tooth 909 comprises a set of protrusions, such as a protrusion facing internally towards the trocar shaft, and/or a protrusion facing externally towards the cannula. Optionally, one protrusion is utilized for insertion and/or retraction of the trocar, for example by being pushed inwards to allow movement of the trocar with respect to the external cannula. A second, opposite facing protrusion may be utilized for clasping to the trocar during retraction of trocar, so that during removal of the trocar from the external cannula the trocar 'collects' the sleeve from its top position between the trocar and the cannula.

FIG. 10 is a drawing of a ratchet-based applicator for anchor deployment, according to some embodiments of the invention.

In some embodiments, an anchor applicator 1001 is positioned within a trocar. In some embodiments, the anchor applicator comprises a handle 1003, a shaft 1005, and a distal portion comprising a set of teeth 1007 and/or teeth 1009.

In some embodiments, handle 1003 can be pulled in the proximal direction from the trocar, and then pushed back down to activate the anchor deployment.

In some embodiments, shaft 1005 comprises a toothed edge 1011. Optionally, edge 1011, together with a lever configured on an inner surface of the trocar shaft (not shown in this figure), comprise a ratchet assembly, as further explained herein.

In some embodiments, the upper set of teeth, 1007, are configured for locking into a sliding element (not shown in this figure), which in turn pushes the anchor thrusting elements forward when handle 1003 is pushed down.

In some embodiments, the lower set of teeth, 1009 provide a sliding release mechanism for retracting the thrusting elements back into the trocar. Optionally, teeth 1009 are forced back into a lumen of the trocar shaft, for example moving closer to each other. Optionally, such movement further causes teeth 1007 to move closer to each other, thereby releasing the locking of the sliding element.

FIGS. 11A-B are drawings of a spring element coupled to thrusting elements for anchor deployment, and an enlarged view of a sliding element positioned on top of the spring, according to some embodiments of the invention.

In some embodiments, a spring 1101 is positioned within a lumen of the trocar shaft. In some embodiments, anchor thrusting elements 1103 are positioned alongside the spring, for example directly above the anchors (not shown in this figure). In some embodiments, a sliding element 1107, shown in an enlarged view in FIG. 11B, is attached to the spring at a proximal end.

In some embodiments, teeth of an anchor applicator, for example teeth 1007 as explained above, are pushed against a surface 1105 of sliding element 1107, for example when the anchor applicator is pushed down to actuate anchor deployment. Sliding element 1107, in turn, further pushes down the anchor thrusting elements 1103 that are attached to it, advancing the anchors towards the tissue.

In some embodiments, once the anchor applicator has been pushed to its extent and the anchors are deployed, teeth such as teeth 1009 for example as explained above are pushed into a lumen of the trocar shaft, and compressed spring 1101 automatically returns back to its original position, causing elevation of anchor thrusting elements 1103 back into a lumen of the trocar shaft.

FIG. 12 is a drawing of an external cannula comprising anchors, according to some embodiments of the invention.

In some embodiments, a head portion at a proximal end of the cannula comprises an insertion hole 1201, through which the trocar and/or other surgical instruments are introduced to cannula. In some embodiments, the head portion comprises a valve 1203, for example for regulating $CO_2$ insertion.

In some embodiments, at least a portion of the cannula comprises anti-slip protrusions 1205.

In some embodiments, one or more anchors 1207 are positioned at a distal portion of the external cannula, for example at recesses as described herein.

FIG. 13 is a cross section view of a head portion of the external cannula, according to some embodiments of the invention.

In some embodiments, when the trocar surrounded by the sleeve is inserted into the external cannula, a perimeter of the sleeve covered portion of the trocar is larger than a perimeter of lumen 1301 of the cannula. Optionally, upon reaching surface 1303, an outward facing extension of the sleeve for example as shown hereinabove catches onto protrusion 1305 of the cannula, so that the sleeve is maintained in an upper position, sealing a spacing between the trocar and the cannula. Optionally, a sealing between the trocar and external cannula is provided by means other than the sleeve, for example an annular band (such as an o-ring) may be used at one or more locations along the trocar shaft.

FIG. 14 is a drawing of a trocar and external cannula assembly, according to some embodiments of the invention.

In some embodiments, a proximal portion of the assembly comprises the trocar handle 1401. In some embodiments, a retractable and pushable handle of an anchor applicator 1403, which is located inside a lumen of the trocar shaft, is configured within handle 1401. In some embodiments, any of the handles comprise an anti-slip surface such as surface 1411, for example to facilitate gripping of the handle.

In some embodiments, the trocar is inserted into the external cannula such that handles 1401 and 1403 are positioned above a cap 1405 of the cannula.

In some embodiments, a distal portion of the trocar, for example comprising narrow portion 1407 and tip 1409 protrudes externally from a distal opening of the external cannula.

In some embodiments, the anchor applicator is cannulated, for example to insert the assembly over a guide wire. Additionally or alternatively, the trocar handle surrounding the anchor applicator is cannulated, for example leading to a lumen within the trocar shaft that is not occupied.

An Exemplary Anchor Deployment Procedure

In the following description, FIGS. 16A-C, 17A-D and 18 describe each of the stages of an exemplary anchor deployment procedure, corresponding to the set of drawings shown in FIG. 15.

FIGS. 16A-C, corresponding with FIG. 15A, are cross section views showing actuation of a ratchet mechanism during pulling back of the anchor applicator, according to some embodiments.

In some embodiments, to begin the anchor deployment procedure, a user pulls back on the handle 1603 of an anchor applicator 1601. During pull back, applicator is lifted up freely, since lever 1605 is maintained away from a toothed edge 1607 of the anchor applicator, disengaging the ratchet assembly. Once applicator 1601 is lifted up it reaches a position in which its upper set of teeth 1609 lock against a surface of sliding element 1611 (shown in FIG. 16C).

Optionally, in the cocked stage, sliding element 1611 is positioned above the anchor thrusting elements, in a position suitable for advancing the anchor thrusting elements which in turn will deliver the anchors towards the tissue.

FIGS. 17A-D, corresponding with FIG. 15B, are side views of a distal portion (A-B) and cross section views (C-D) of the assembly during activation of the anchor applicator for deploying anchors, according to some embodiments of the invention.

Figure 17B:
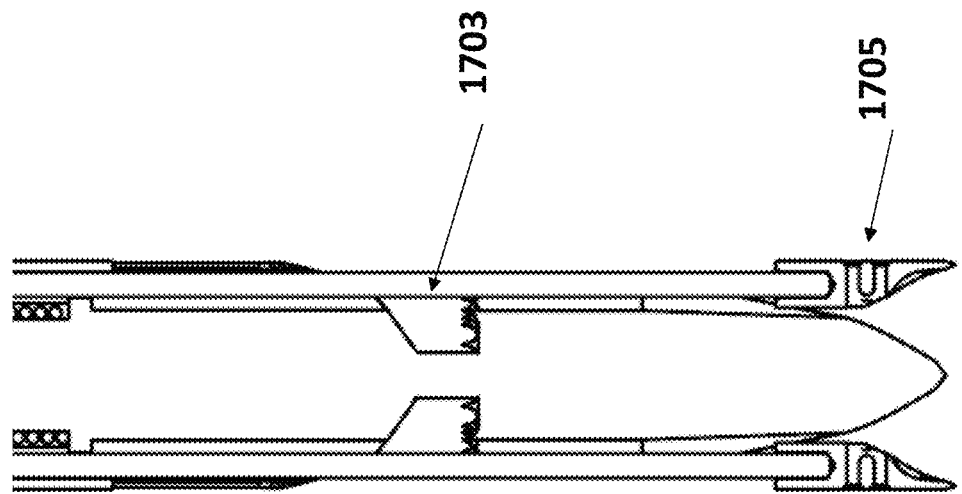
Figure 17A:
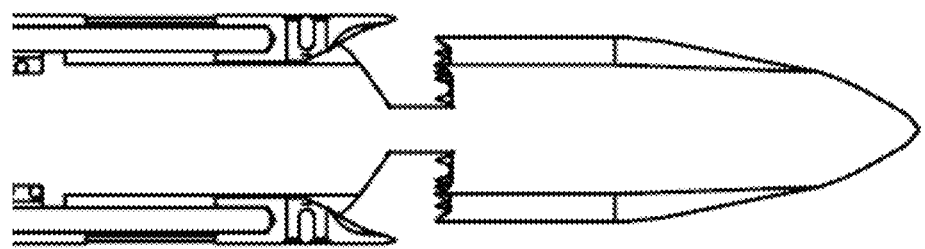

In some embodiments, a cocked stage of the assembly, shown, for example, in FIGS. 17A and 17C, comprises the anchor applicator 1601 being positioned such that teeth 1609 are locked onto the surface of the sliding element 1611, and a distal edge of the sliding element is configured above the anchor thrusting elements 1703, positioned alongside spring 1701.

In some embodiments, as a the user pushes a handle of applicator 1601, as shown in FIG. 15B, toothed edge 1607 of the applicator clicks against lever 1605, allowing for movement of the applicator in a single direction and limiting movement in an opposite direction. In some embodiments, lifting of applicator 1601 is prevented by the ratchet assembly, for example to prevent pull back of the applicator during anchor deployment, providing additional safety.

In some embodiments, feedback is provided to the user such as a physician to indicate a current operational mode of the device, for example tactile feedback (such as by resistance to pulling and/or advancing the handle), audible feedback (such as by a clicking sound of components being moved with relative to each other), visual feedback (such as by scaling marks on the handle indicating the extent of advancement). In an example, a clicking sound of lever 1605 against the teeth of edge 1607 is made as the applicator is advanced forward, indicating to a user that anchors 1705 are currently being pushed forward. In some embodiments, spring 1701 is compressed.

When applicator 1601 has been pushed to a lowest limit for example as shown in FIGS. 17B and 17D, anchors 1705 penetrate into the tissue, for example of the fascia layer. In some embodiments, lower set of teeth 1707 are forced into a lumen in the trocar shaft, reducing a diameter so that the sliding element 1611 can be free to move back up through the trocar shaft (positioned externally to the sliding element.

In some embodiment, anchor thrusting elements 1703 are automatically pushed back up into a lumen of the trocar shaft, for example by utilizing the elastic force of compressed spring 1701. In some embodiments, sliding element 1611 is pushed back up by spring 1701, lifting anchor thrusting elements 1705. Optionally, a distal end of the thrusting element 1703 disengages anchor 1705 that is now deployed in the tissue.

Alternatively, in some embodiments, a user can mechanically activate the return of the anchor thrusting elements, for example by rotating the applicator, for example by 50, 70, or 90 degrees, for releasing the ratchet mechanism, and/or simply pulling the applicator back.

FIG. 18, corresponding with FIG. 15C, is a cross section view of the assembly once anchors have been deployed into the tissue, and the sliding element 1611 was retracted back. The assembly is shown before removal of the trocar from the external cannula, according to some embodiments of the invention.

In some embodiments, a configuration of the assembly before removal of the trocar from the external cannula includes sliding element 1611 located in its upper, original position, such that lever 1605 (not shown in this figure) is distanced away from toothed edge 1607. In some embodiments, lower set of teeth 1707 are forced into a lumen of the trocar.

FIGS. 19A-B are a drawing showing removal of the trocar from the external cannula (A) and a cross section of the assembly during removal (B), according to some embodiments of the invention.

In some embodiments, trocar 1901 is retracted from external cannula 1903. In some embodiments, as the trocar is lifted up, a protrusion 1905 on a sleeve for example as described in FIG. 9 clings to the trocar during retraction. Optionally, clinging of protrusion 1905 is possible only as the narrow portion 1907 of the trocar reaches the sleeve. Optionally, removed trocar 1901 comprises the sleeve configured back in its original position, surrounding narrow portion 1907 and portions of the trocar shaft configured above and/or below the narrow portion.

FIG. 20 is a flowchart of a method for anchor deployment using a wound closure device comprising an obturator positionable within an external cannula, according to some embodiments of the invention.

In some embodiments, an obturator comprises an elongated shaft, and a distal portion of the shaft comprises a narrow portion having a diameter smaller than the diameter of portions of the shaft configured above and below the narrow portion.

In some embodiments, a proximal facing surface of the shaft defined below the narrow portion is configured for abutting against a surface of the fascia tissue layer facing the abdomen. In some embodiments, the surface of the shaft portion defined by the narrow portion comprises one or more projections. In some embodiments, the surface is textured. In some embodiments, the surface comprises an expandable structure.

In some embodiments, the obturator comprises a blunt distal tip, for example being a rounded tip.

In some embodiments, the obturator comprises one or more anchors positioned alongside the obturator shaft. Optionally, the anchors are positioned in parallel recesses. Additionally or alternatively, the anchors are positioned in arched recesses. In some embodiments, the obturator comprises anchor thrusting elements, for example configured above the anchors. In some embodiments, the anchor thrusting elements are positioned in recesses parallel to a longitudinal axis of the obturator. Alternatively, the anchor thrusting elements are positioned in recesses twisting helically around the obturator shaft.

In some embodiments, sutures are threaded through an anchor. Optionally, the free ends of the sutures extend within the external cannula, for example being connected the obturator's handle at a proximal end.

In some embodiments, a distal portion of the obturator is inserted into a port in the abdominal wall (2001). Optionally, the obturator is inserted through a cannula, for example a cannula that was previously positioned in the tissue. Alternatively, the obturator is inserted directly into the tissue, for example after a cannula has been removed from the port, to close the remaining wound.

In some embodiments, the obturator is pushed until the narrow portion of the obturator shaft is fully inserted into the fascia tissue layer (2003). Optionally, a user senses that the narrow portion has been fully inserted by encountering resistive force formed as the wider (or widening) portion above the narrow portion is pushed through the incision in the fascia.

In some embodiments, the user slightly pulls the obturator back up until the proximal facing surface of the shaft configured below the narrow portion is held against the fascia layer (2005). Optionally, projections on the surface prick into the fascia, enhancing a contact between the obturator and the tissue. A potential advantage of the surface abutting against the fascia tissue includes preventing unwanted removal of the obturator.

In some embodiments, suture anchors are deployed into the tissue, for example the fascia (2007). In some embodiments, sutures are deployed by lifting a cap at a proximal end of the obturator, and pushing the cap down to advance the anchor thrusting elements, which in turn push the anchors into the tissue. Optionally, the obturator comprises an anchor deploying mechanism for example as described herein in reference to the trocar and/or to a trocar and external cannula assembly.

In some embodiments, the obturator is removed from the tissue (2009). Optionally, the external cannula is removed from the tissue. In some embodiments, the suture ends are tied to close the wound (2011).

FIGS. 21A-H are a set of drawings showing an operating procedure of a wound closure device, according to some embodiments of the invention.

FIG. 21A shows a cannula 2101 positioned at an abdominal port. Optionally, the cannula has been used throughout a laparoscopic procedure, for example for insertion of a laparoscope through. FIG. 21B shows an obturator 2103 being inserted through cannula 2101. FIG. 21C shows obturator 2103 being positioned in the tissue such that the narrow portion 2105 is surrounded by the fascia tissue layer 2107, which optionally bounced back around it. In some embodiments, an expandable leaflet structure 2109 is positioned on a surface of the obturator shaft facing the fascia, shown in this figure in its opened position.

In some embodiments, a user pulls back cap 2111, positioned on proximal end of obturator 2103, to begin the anchor deployment. In some embodiments, as cap 2111 is pushed back down, anchor thrusting elements 2113, in this figure shown in helical recess around the obturator shaft, are forced towards anchors 2115 to push them into the tissue. FIG. 21D shows anchors 2115 deployed at fascia 2107, for example above, through, and/or directly below fascia 2107. Optionally, sutures 2117 extend within cannula 2101.

In some embodiments, anchor thrusting elements 2113 are retracted into a lumen of the obturator shaft, for example automatically retracted with the aid of a spring. FIG. 21E shows anchor thrusting elements 2113 within a lumen of the obturator shaft, and the expandable leaflet structure 2109 in its closed position, optionally in preparation for removal of the obturator from the tissue.

In FIG. 21F, the obturator is pushed slightly back down deeper into the tissue. Optionally, by pushing the obturator slightly deeper, closure of the expandable leaflet structure is ensured. Optionally, by pushing the obturator slightly deeper, a proximal end of sutures 2117 disengages a proximal end of obturator 2103 and/or cannula 2101.

In some embodiments, for example as shown in FIG. 21G, obturator 2103 is removed from cannula 2101. Optionally, the free ends of sutures 2117 extend externally from an insertion hole 2119 of the cannula.

FIG. 21H shows removal of cannula 2101. Optionally, for example if the suture ends remain attached to a proximal end of the cannula, removal of the cannula may pull on the sutures, strengthening a fixation of anchors 2115 to the tissue. Optionally, the sutures are tied together to close the wound after the cannula is removed. Alternatively, the sutures are ties through the cannula, and only then the cannula is removed.

An Exemplary Geometry of a Distal Portion of a Trocar

FIG. 22 shows an exemplary geometry of a distal portion of a trocar, according to some embodiments of the invention. In some embodiments, one or more recesses 2201 in trocar shaft 2203 form the narrow portion. Optionally, for example as shown in this figure, a recess comprises a rectangular profile. This figure shows two rectangular recesses, opposite from each other, forming a 'wall' 2205 of the shaft in between them, to be surrounded by fascia tissue entering the recesses.

In some embodiments, a depth of the recess in a radial direction, as shown for example by bar 2211, is large enough to allow fascia tissue to at least partially enter the recess. A depth of the recess, as referred to herein, may extend between a virtual continuation of a wider portion of the shaft such as portion 2213 configured below the narrow portion or portion 2215 configured above the narrow portion, and a surface 2217 of the shaft at the location of the narrow portion. Optionally, a depth of the recess ranges between 0.1-5 mm, such as 1 mm, 2 mm, 3.5 mm, or any smaller, larger or intermediate distances.

A width of the narrow portion, formed as 'wall' 2205, can be referred to as the summed distances of opposite faces of wall 2205, such as surface 2217 and surface 2221, from a longitudinal axis AA' of the shaft. Optionally, distance 2223 measured between surface 2217 and axis AA' of the shaft ranges between 0.3-5 mm, such as 0.5 mm, 1 mm, 3 mm.

In some embodiments, a slot 2207 is configured in proximity to the distal tip 2209 of the trocar. Optionally, the slot extends along a cross section of the trocar, for example extending through to an opposite side of the shaft. In some embodiments, the slot is configured for receiving a blade. Optionally, the orientation of the slot is in line with the orientation of 'wall' 2205. In some embodiments, shaft portion 2215 comprises a tapered surface 2219, facing the one or more recesses.

An Exemplary Geometry of a Surface Configured Below a Narrow Portion of a Trocar Shaft FIG. 23 shows an exemplary geometry of a surface defined below a narrow portion of the trocar shaft, according to some embodiments of the invention. In some embodiments, surface 2301, comprises one or more lumens 2305. Optionally, an opening of the lumen faces the proximal direction. Optionally, during positioning of the trocar, for example when the trocar is slightly pulled up in the proximal direction, at least a portion of the fascia layer is pushed into one or more of the lumens, for example slightly entering the trocar shaft. A potential advantage of the tissue being pushed, at least partially, into the lumens includes enhanced contact between surface 2301 and the fascia layer, for example assisting in stabilizing the trocar during anchor deployment. In some embodiments, lumens 2305 comprise a portion of surface 2301, for example being 20%, 40%, 70%, 85% or intermediate, higher or lower percentages of surface 2301. The lumens may be shaped as sectors, rings, small circular holes, or any other configuration. In some embodiments, at least a portion of the trocar such as the distal portion is formed using molding techniques, and the lumens are formed by using a mold having the desired lumen pattern.

An Anchorless Obturator for Wound Closure

FIGS. 24A-E are a set of drawings showing an operating procedure of an anchorless obturator for wound closure, according to some embodiments of the invention.

In some embodiments, a distal portion 2401 of a shaft 2402 of the obturator comprises a narrow portion 2403, having a diameter smaller than a diameter of portions of the shaft configured above and below the narrow portion, such as portion 2405 and portion 2407 respectively. In some embodiments, a proximal facing surface 2406 of shaft portion 2407 defined by the narrow portion is adapted for abutting against a surface of fascia 2409, for example comprising one or more projections 2411.

Various embodiments may comprise shafts of various cross sections, for example having an elliptical form or any other configuration suitable for insertion through a wound 2423.

In some embodiments, the obturator comprises one or more needles 2412. Optionally, the needles are positioned within and/or at the surface of shaft portion 2407. For example, in some embodiments, needles 2412 are attached to a pitchfork shaped structure 2413 that is positioned within shaft 2402. In some embodiments, a central portion 2415 of structure 2413 extends longitudinally in the proximal direction, for example extending beyond narrow portion 2403. Optionally, portion 2415 extends all the way through shaft 2402 to reach a proximal end of the obturator, for enabling manipulation by a user.

In some embodiments, side portions 2417 of structure 2413 extend within shaft portion 2407. Optionally, a needle 2412 is removably attached to a proximal end of portion 2417, for example with the sharp tip of the needle facing the proximal direction.

In some embodiments, a needle 2412 is threaded with one or more sutures 2419. Optionally, a length of a suture extends between both needles. In some embodiments, suture 2419 is seated within portion 2427 of the shaft. Optionally, suture 2419 is folded so that it is compatibly packed within portion 2427. Additionally or alternatively, portion 2427 may comprise a groove for receiving the suture. The groove may be configured internally with shaft portion 2427, externally on a surface of shaft 2427, or a combination thereof. In some embodiments, for example if portion 2427 comprises a blade and/or a recess for receiving a blade, suture 2419 may be seated at a more proximal portion of shaft.

In some embodiments, suture 2419 is a single stranded suture. Alternatively, suture 2419 is a double stranded suture. Optionally, suture 2419 is formed with a loop 2429 for engaging needle 2412.

In some embodiments, shaft portion 2405 comprises one or more recesses 2421 for receiving needles 2412 and/or portions 2417, for example as will be further shown.

Figure 24A:
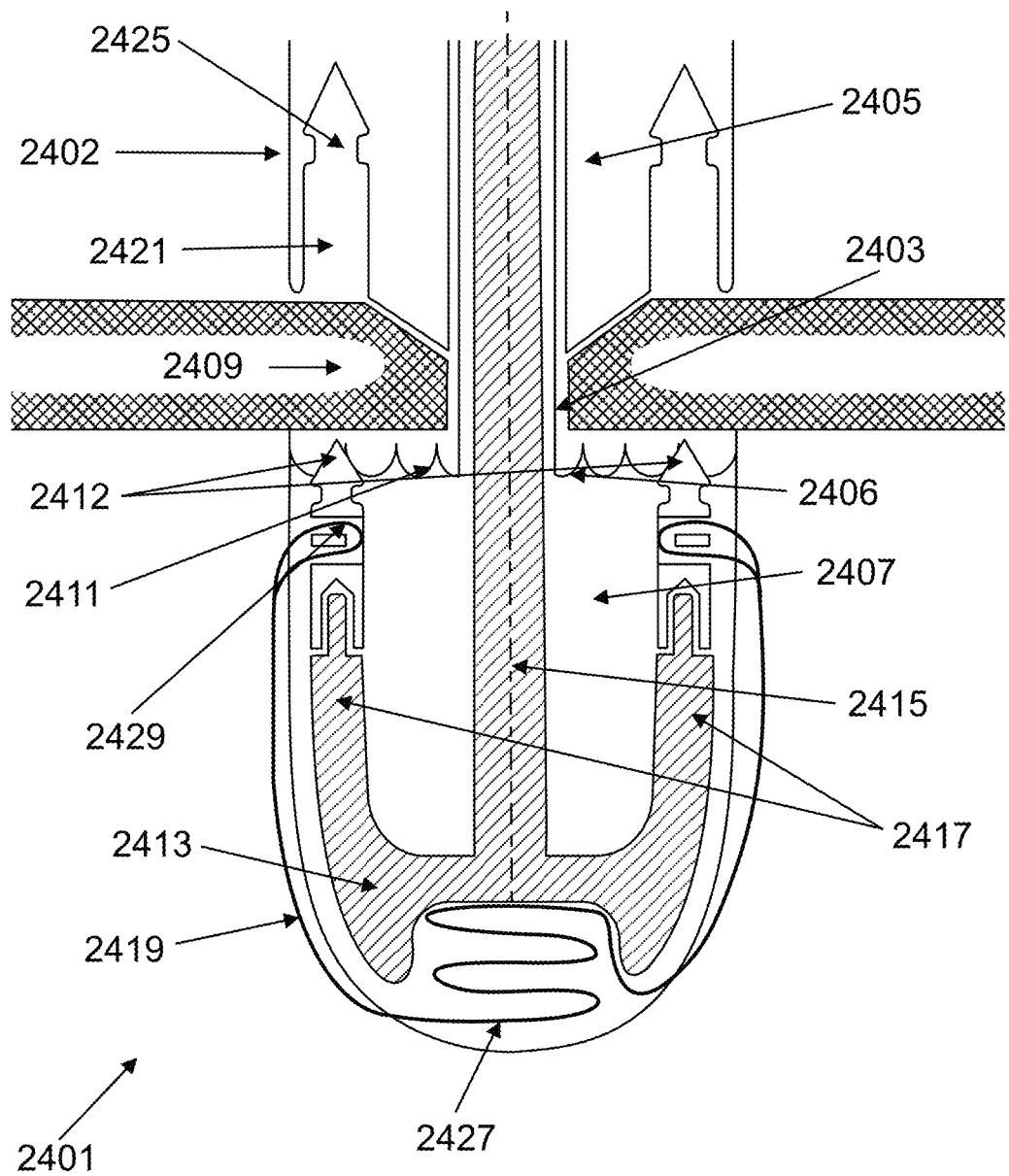

In some embodiments, as shown, for example, in FIG. 24A, the obturator is inserted into the abdominal wall, and positioned such that fascia tissue 2409 surrounds narrow portion 2403. Optionally, surface 2406 is abuts against the distal facing surface of fascia 2409, while projections 2411 may prick into the fascia for enhancing a contact.

Figure 24B:
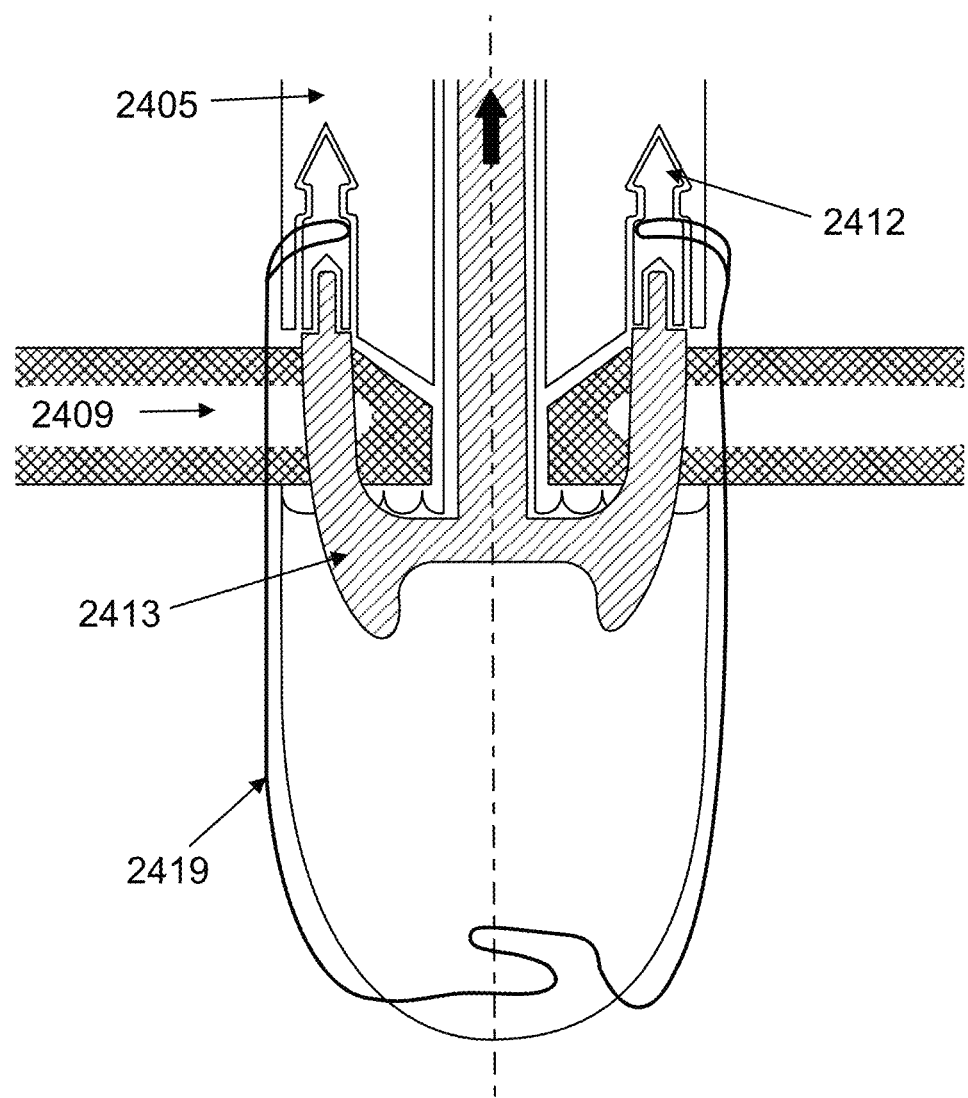

In some embodiments, as shown, for example, in FIG. 24B, pitchfork structure 2413 is pulled in the proximal direction, causing needles 2412 to penetrate through fascia 2409 in the proximal direction. In some embodiments, needles 2412 exit fascia 2409 and enter recesses 2421 in shaft portion 2405. Suture 2419 is pulled in the proximal direction through fascia 2409 by needles 2412. Optionally, a needle 2412 is configured for rotating around its longitudinal axis, for example during penetration of the fascia. A potential advantage of a rotating needle includes facilitating penetration of the needle into the fascia. Optionally, rotation is obtained by winding a suture around the needle such that when the needle is pushed into or through the fascia, and force such as friction (for example by a clasp or other means suitable for restraining a portion of the suture) is applied to a continuing portion of the suture at any location along the suture, the winding of the suture causes the needle to rotate as it advances.

Figure 24C:
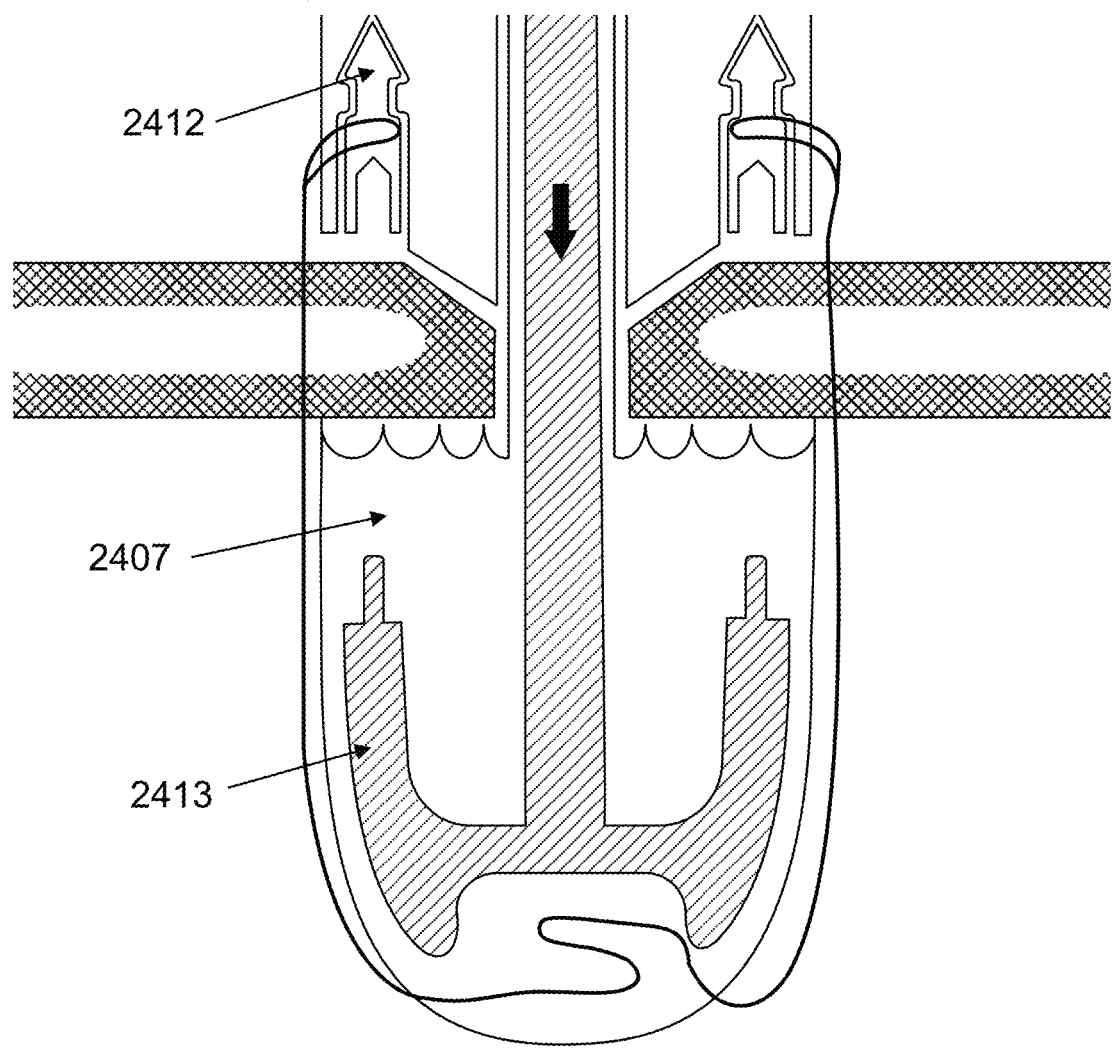

In some embodiments, as shown, for example, in FIG. 24C, pitchfork structure 2413 is pushed in the distal direction, optionally returning to its original position within shaft portion 2407. Needles 2412 remain within recesses 2421, for example being caught by a clasp, a pin, a hook or other means suitable for maintaining a coupling between the needle and the recess wall. In some embodiments, recess 2421 comprises one or more notches 2425, for example for engaging the needle when it enters the recess. Optionally, the engagement between the recess and the needle is a frictional engagement.

Figure 24D:
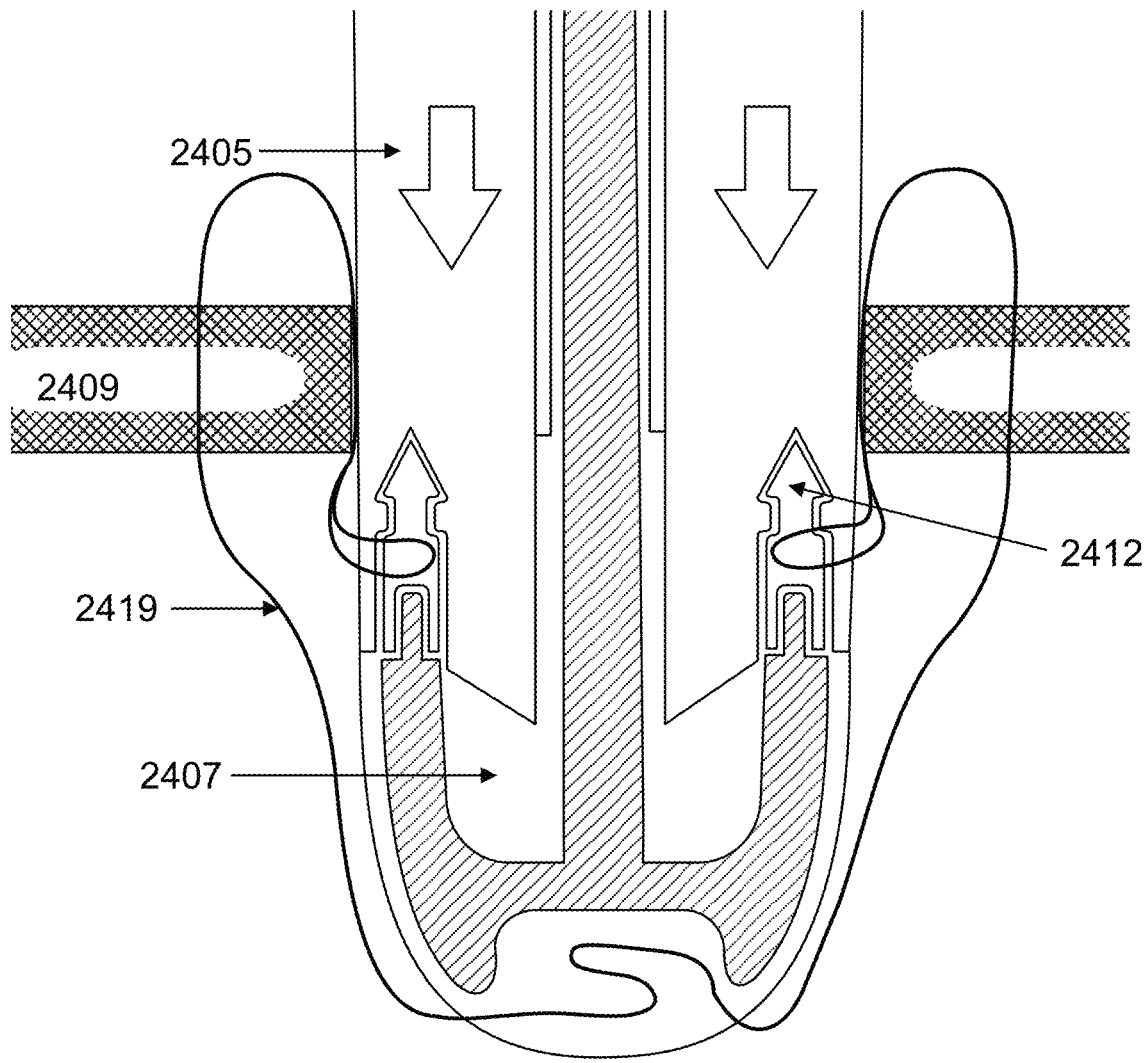

In some embodiments, as shown, for example, in FIG. 24D, shaft portion 2405 is pushed through fascia 2409 to engage portion 2407. Optionally, side portions 2417 enter, at least in part (e.g. their proximal ends), recesses 2421. Optionally, suture 2419 remains attached to needles 2412, for example at its ends, so that it crosses fascia 2409 a second time, this time in the distal direction, by pushing portion 2405 to engage portion 2407.

In some embodiments, the obturator, optionally in its 'compact' configuration, where portion 2405 engages portion 2407, is pulled in the proximal direction to be removed from the abdomen. The ends of suture 2419 may slide away from needles 2412 upon removal of the obturator, and/or be cut from the needles, and/or be detached from the needles by other means suitable for decoupling the sutures.

Figure 24E:
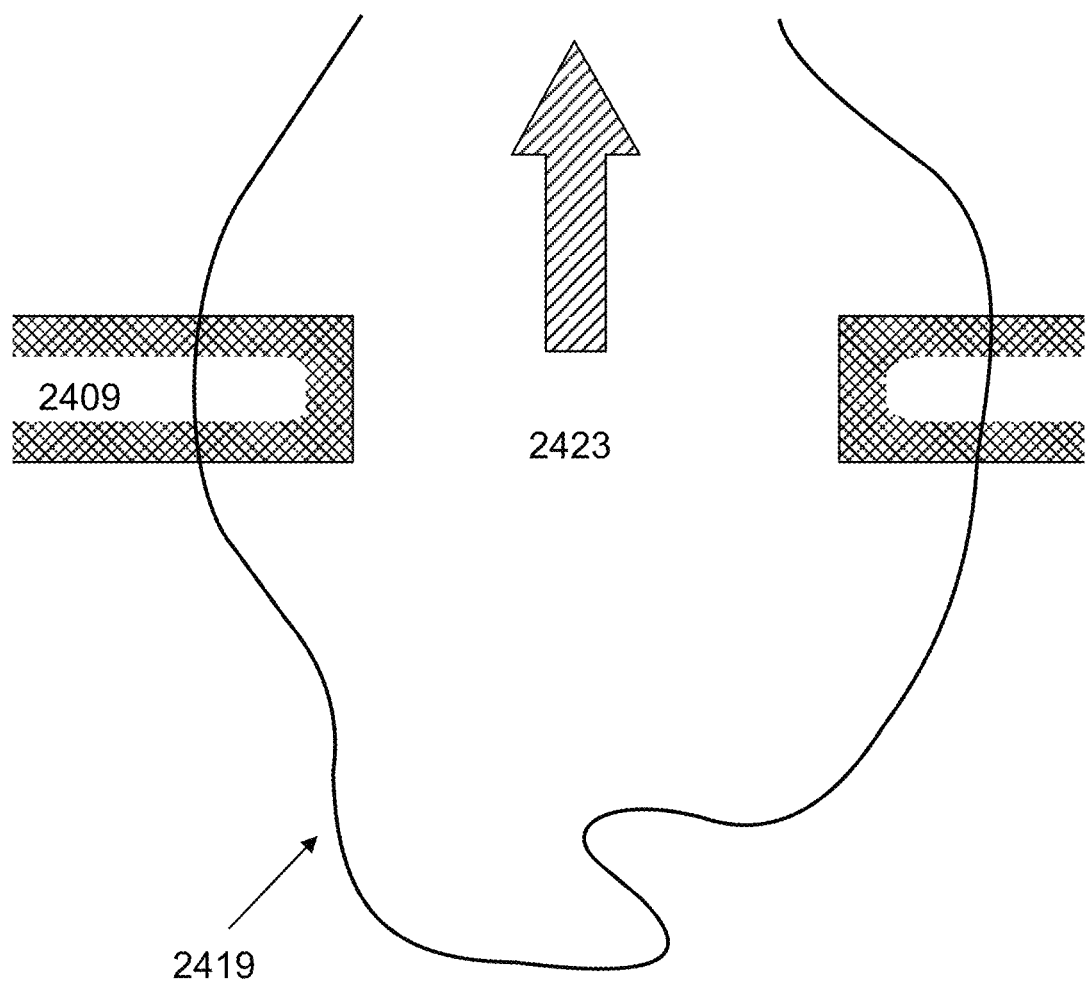

In some embodiments, as shown, for example, in FIG. 24E, suture 2419 remains attached to fascia 2409. Optionally, the ends of suture 2409 (or, alternatively, two or more sutures) extend from opposite sides of wound 2423. In some embodiments, the ends are tied together for closing the wound.

A potential advantage of deploying a suture with an anchorless obturator, for example as described above, includes avoiding the deployment of closure-assisting elements such as anchors and/or needles that remain within the tissue. For example, in an obturator as described, the needles are removed along with the obturator, leaving solely the suture positioned at a location of the fascia.

FIGS. 25A-D show a distal portion of a trocar structured to provide a tissue folding effect (25A, 25B), and an illustration of the penetration points of the anchors in the tissue obtained by using the tissue folding effect (25C,25D), according to some embodiments of the invention.

In some embodiments, a geometry of the distal portion of the trocar is suitable for creating a tissue folding effect upon penetration into the fascia. In the exemplary configuration shown herein, a narrow portion 2501 of the trocar shown in FIG. 25A comprises a shaft portion 2503 formed with one or more recesses 2507, and a tubular portion 2509 extending proximally to portion 2503. It is also possible to refer to the narrow portion as tubular portion 2509 alone, while shaft portion 2503 may be defined as a portion created by removal of material from a shaft portion configured directly below the narrow portion, comprising the proximally facing surface that abuts against the fascia. In some embodiments, portion 2509 is not tubular, for example comprising a rectangular, triangular, trapezoidal and/or other cross section profile.

In some embodiments, as shown for example in FIG. 25B, during advancement of anchors 2511 to deploy them in the fascia tissue 2513 and before actual penetration of the tissue, the anchors force fascia tissue 2513 in a distal direction, as indicated by arrows 2517, forming a tissue fold 2519 between the anchor 2511 and shaft portion 2503 of the narrow portion 2501.

In some embodiments, a proximal facing surface 2521 of shaft portion 2503, optionally comprising one or more projections 2535, abuts against fascia 2513 and thereby defines a force on the tissue acting in a proximal direction which opposes the distally directed force applied by the anchors and/or by the anchor thrusting elements on the tissue during advancement of the anchors. These opposing forces that act on the tissue may contribute to the formation of fold 2519.

In some embodiments, once fold 2519 is obtained, the anchors are advanced further to penetrate the crimped tissue.

A potential advantage of forming a tissue fold prior to deployment of the anchors in the tissue may include increasing a distance between the deployed anchors, for example as compared to anchors deployed without folding the tissue. By temporarily approximating, using the fold, tissue portions that the anchors penetrate through, the anchors can be deployed at a greater distance from each other. FIG. 25C shows penetration points 2523 approximated towards each other by tissue fold 2519. Optionally, penetration points 2523 are located at the bases of an upside down U shape of the crimped tissue. In some embodiments, the trocar is structured to maintain penetration points 2523 apart from each other, for example by shaft portion 2503, reducing the risk of having an anchor penetrate through to the opposing side of the tissue fold.

In FIG. 25D the fold is released. Optionally, the fold is released once the anchors penetrated the tissue thus no longer imposing a stretching force on the tissue in the distal direction, leaving points 2523 at a greater distance 2525 from each other. Optionally, distance 2525 ranges between, for example, 5-50 mm, such as 10 mm, 25 mm, 40 mm or intermediate, larger or smaller distances.

In some embodiments, anchors 2511 are delivered into the tissue along a linear path. In some embodiments, by creating the tissue fold, an effect of diagonally deployed anchors is obtained, without actually deploying the anchors at an angle relative to the axis of the trocar. Alternatively, anchors are deployed at an angle relative to the trocar axis. Alternatively, a tissue fold is created and the anchors are deployed at an angle relative to the trocar axis, potentially increasing a distance 2525 between the deployed anchors to an even larger distance.

In some embodiments, a size of the tissue portion which is folded in between anchors 2511 and shaft portion 2503 of narrow portion 2501 is determined by a distance 2527 between proximal facing surface 2521 of shaft portion 2503 and surface 2529 of distal tip 2531 on which the tissue abuts against.

Additionally or alternatively to anchors, in some embodiments, tissue fold 2519 is obtained by one or more extensions (not shown in figure) of proximal shaft 2533, extending in the direction of the narrow portion 2501, along at least a portion of the length of the narrow portion. Optionally, the extensions are substantially aligned with the narrow portion 2501. In some embodiments, tissue is crimped between the extensions of proximal shaft 2533 and shaft portion 2503 and/or tubular portion 2509.

In some embodiments, increasing a distance between the deployed anchors is obtained by other structures and/or methods, such as by clamping the tissue using a clamp or similar device.

In some embodiments, shaft portion 2503 comprises a rectangular cross section profile, for example as shown herein. Alternatively, shaft portion 2503 comprises a circular, squared, and/or any other cross section profile. Optionally, an area of proximally facing surface 2521 of shaft portion 2503 (for example without the projections 2523) is smaller than a surface are of surface 2529 of distal tip 2531.

In some embodiments, surface 2529 of distal tip 2531 comprises a surface structure suitable for increasing contact with the tissue, for example comprising one or more projections (not shown in this figure). Optionally, surface 2529 is textured, for example comprising bumps and/or waves.

FIGS. 26A-I illustrate an anchor deployment procedure involving a tissue folding effect on the fascia, and an exemplary structure and operating mechanism of a trocar and external cannula assembly, according to some embodiments of the invention.

The following figures generally illustrate a trocar 2602 positioned within an external cannula 2604, for deploying suture anchors in the fascia.

In some embodiments, as shown for example in FIG. 26B, a distal portion 2601 of the trocar configured distally to the narrow portion 2603 is advanced into the fascia 2605. In some embodiments, a handle 2607 comprising a spring 2609 contained within a lumen of the handle is pulled in a proximal direction, tensioning spring 2609. A sliding element 2611 configured within a lumen of handle 2607 and coupled to a distal end of spring 2609 remains static while the handle is pulled in a proximal direction, until a proximal set of grab teeth 2619 of the sliding element extend radially outwards and lock into a position in which distally facing surfaces in the wall of the handle contact the proximal ends of the grab teeth 2619. Anchor thrusting elements 2613 are positioned at a location suitable for applying force onto the anchors to advance them distally.

In FIG. 26C, handle 2607 is pushed in a distal direction, to begin advancement of anchors 2615 towards the tissue by forcing sliding element 2611 distally, thereby forcing anchor thrusting elements 2613 in a distal direction by the sliding element. During advancement of anchors 2615, fascia 2605 is stretched in a distal direction, and a tissue fold 2617 is formed between anchors 2615 and narrow portion 2603, for example as shown in FIG. 26D.

In some embodiments, once tissue fold 2617 is obtained, handle 2607 is further pushed downwards to cause anchors 2615 to penetrate the fascia, as shown for example in FIG. 26E. A potential advantage of pushing handle 2607 in a distal direction while the spring remains static (e.g. not stretched and/or compressed by the pushing of the handle) may include providing more accurate sensing and control to a user such as a physician operating the trocar, as the resistance encountered by the user when forcing the anchors into the tissue is solely the resistance of the tissue, and not a combined resistance of the tissue and the spring or other mechanical component of the trocar thereof.

In some embodiments, upon further advancement of the anchors distally, grab teeth 2619 of sliding element 2611 are pushed radially inward, for example by a step or protrusion configured on an inner wall of trocar shaft 2621. At this point, occurring between the configurations shown in FIGS. 26F and 26G, sliding element 2611 can again fit within the lumen of handle 2607, allowing spring 2609 to bounce back to its initial, non-extended configuration within the lumen of the handle. As spring 2609 returns to an initial position, as shown for example in FIG. 26G, sliding element 2611 is pulled back in a proximal direction by the spring, carrying along anchor thrusting elements 2613.

In some embodiments, following the "snapping point" in which the spring returns to its original length, as shown in FIG. 26G, tissue fold 2617 in fascia 2605 is substantially released, leaving anchors 2615 comprising sutures 2623 deployed at a distance from each other in the fascia. At this stage, the trocar and external cannula assembly may be advanced further distally, for example as shown in FIG. 26H, to position the external cannula in fascia 2605. In FIG. 26I, after trocar 2602 has been pulled in a proximal direction and detached from the external cannula 2604, cannula 2604 remains in the tissue, providing a port for insertion of tools such as a laparoscope into the abdomen. In some embodiments, upon removal of cannula 2604 from the tissue, sutures 2623 are tied together to close the wound in fascia 2605.

In some embodiments, as shown in the exemplary structure described herein, a maximal diameter 2625 (FIG. 26A) of the trocar and external cannula assembly ranges between, for example, 6-25 mm, such as 10 mm, 15 mm, 23 mm or intermediate, larger or smaller diameters. In some embodiments, one or more components of the assembly are configured to fit within one another so as to maintain a relatively small total diameter, for example, the sliding element as described hereinabove fitting at least in part within a lumen of the handle.

FIGS. 27A-B show an exemplary handle and sliding element of a trocar, according to some embodiments of the invention.

In some embodiments, handle 2701 for example as shown in FIG. 27A comprises a gripping portion 2703, and a shaft 2705. In some embodiment, shaft 2705 is at least partially cannulated, comprising a lumen 2707 extending along at least a portion of the length of handle 2701, such as 30%, 50%, 75% or intermediate, larger or smaller percentages of the length of handle 2701. In some embodiments, handle 2701 comprises a surface 2709 extending across a distal end of handle 2701. Optionally, surface 2709 is shaped for engaging the anchor thrusting elements and pulling them in a proximal direction when handle 2701 is pulled back. In cases in which the "snapping" for example as described hereinabove does not occur, and the anchor thrusting elements are not automatically pulled back by the sliding element, surface 2709 may engage the anchor thrusting elements and force them in a proximal direction as the handle is pulled, providing additional safety in case the assembly malfunctions (e.g. in case the spring fails to return to its non-extended configuration).

In some embodiments, sliding element 2711 for example as shown in FIG. 27B is configured for fitting within lumen 2707 of handle 2701. In some embodiments, sliding element 2711 comprises a shaft 2712, a proximal set of grab teeth 2713. Optionally, teeth 2713 extend radially outwards with respect to shaft 2712, and are configured to spring back towards the shaft when external force is applied onto the teeth, for example by the inner walls of the trocar shaft (not shown in this figure), the inner walls of lumen 2707 of handle 2701, and/or by step-like projections configured along the movement path of sliding element 2711 within the trocar. In some embodiments, sliding element 2711 comprises, at a distal end, a set of elements 2715 configured to engage the proximal surface of the anchor thrusting elements, to advance them distally. Optionally, elements 2715 protrude radially outward with respect to shaft 2712.

In some embodiments, a position of sliding element 2711 with respect to lumen 2707 of handle 2701 is determined by the configuration of proximal teeth 2713, for example providing for the sliding element to enter lumen 2707 and slide within it when teeth 2713 are pushed inwards towards shaft 2712, and maintaining sliding element 2711 at a distal position when teeth 2713 extend outwardly. In some embodiments, elements 2715 are configured for engaging the anchor thrusting elements, to provide for pushing the anchor thrusting elements distally by advancing sliding element 2711.

A potential advantage of a trocar comprising components that are sized and/or shaped to fit one within the other (for example sliding element 2711 being shaped and sized to fit within lumen 2707 of handle 2701) may include a compact arrangement of components that allows for a trocar of relatively small diameter to provide various anchor deploying and tissue penetrating functions, as well as providing for smooth axial movement of the components relative to each other.

FIGS. 28A-I are various anchor designs, according to some embodiments of the invention.

In FIGS. 28A-E, an exemplary hollow anchor 2801 is shown. In FIGS. 28F-I, an exemplary self penetrating anchor 2817 is shown.

In some embodiments, an anchor such as hollow anchor 2801 and/or self penetrating anchor 2817 is formed with a lumen 2803 extending along a part of the length of the anchor, for example as shown in FIG. 28G, or along a complete length of the anchor, as shown for example in FIG. 28B. In some embodiments, lumen 2803 is shaped and/or sized to receive an anchor thrusting element 2807.

In some embodiments, for example as shown in FIG. 28B, anchor thrusting element 2807 is advanceable through a distal opening 2809 of the anchor. Optionally, a distal portion 2811 of anchor thrusting element 2807 comprises a smaller cross sectional area than a more proximal portion 2823 of the thrusting element, to advance past the anchor and potentially penetrate the tissue before the anchor. A potential advantage of a hollow anchor 2801 configured for receiving an anchor thrusting element 2807 may include reducing the load applied onto the anchor, as at least a portion of the load is transferred to the anchor thrusting element 2807 positioned within it. Another potential advantage of a hollow anchor may include the ability to penetrate the tissue using a sharp pointed anchor thrusting element, optionally made of metal (for example instead of penetrating the tissue with the anchor itself). The anchor thrusting element further leads the anchor into the abdominal cavity.

In some embodiments, anchor 2801 and/or anchor 2817 comprises one or more inner channels 2821 for passing suture 2813 through, as shown for example in FIGS. 28C and D, and FIGS. 28G-I. In some embodiments, for example in hollow anchor 2801, an inner channel is formed within and/or along an inner wall of lumen 2803.

Optionally, suture 2813 is threaded through the anchor prior to performing the procedure. Additionally or alternatively, suture 2813 is threaded during the procedure.

In some embodiments, anchor 2801 and/or anchor 2817 comprises a substantially flat surface 2815, configured for abutting against the fascia tissue that faces the abdomen, for example when the anchor is pulled in response to the suture 2813 being pulled on, such as during wound closure.

In some embodiments, an anchor comprises a sharp needle-like distal tip 2819 suitable for penetrating the tissue. Alternatively, the anchor comprises a blunt tip. Optionally, a blunt tip provides for stretching the tissue before actual penetration, thereby potentially producing the tissue folding effect for example as described herein.

FIGS. 29A-C illustrate a dove tail interface between the external cannula and the anchors, according to some embodiments of the invention.

In some embodiments, a coupling between an anchor 2901 and the external cannula 2903 in which trocar 2911 is received is configured to sustain anchor 2901 in a fixed position relative to the external cannula when trocar 2911 is moved within the cannula, for example during advancement of the trocar in the cannula to obtain a "ready to use" configuration. In some embodiments, a location (e.g. axial and/or circumferential location) of the coupling between anchor 2901 and external cannula 2903 is determined such as to allow the anchor thrusting elements of the trocar to engage the anchors during operation, while preventing undesired advancement of the anchors distally, such as during advancement of the trocar to a "ready to use" configuration. In some embodiments, as shown for example in the cross section of the trocar and external cannula assembly along lines A-A, tail portion 2905 of anchor 2901 comprises a first width 2907 and a second, larger width 2909 at the outermost portion of anchor 2901. Optionally, width 2909 is larger by at least 10%, 40%, 60% or intermediate, larger or smaller percentages larger than width 2907. Inner wall 2915 of external cannula 2903 is respectively formed with a recess 2917 of similar shape and size, adapted to receive the tail portion 2905 of the anchor.

Similarly, in the more distal cross section along lines B-B of the trocar and cannula assembly, the profile of recess 2917 changes to match a more distal portion of anchor 2901, such as a portion in which a suture 2919 is passed.

In some embodiments, a proximal portion of external cannula 2903 (not shown in this figure) comprises a geometry suitable for aligning trocar 2911 with respect to external cannula 2903. In an example, the proximal portion of the external cannula comprises one or more recesses and/or projections configured to engage respective projections and/or recesses of trocar 2911.

Figure 29F:
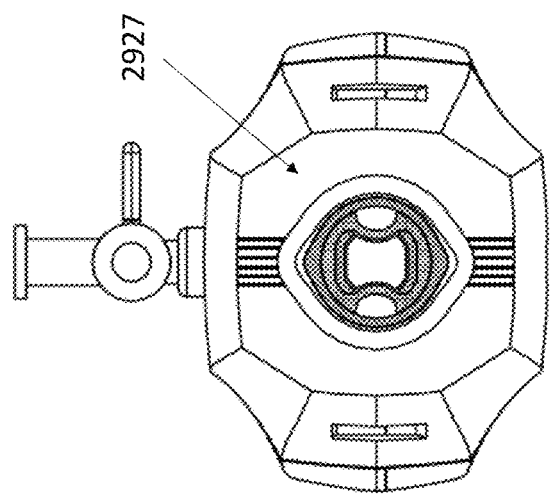
Figure 29E:
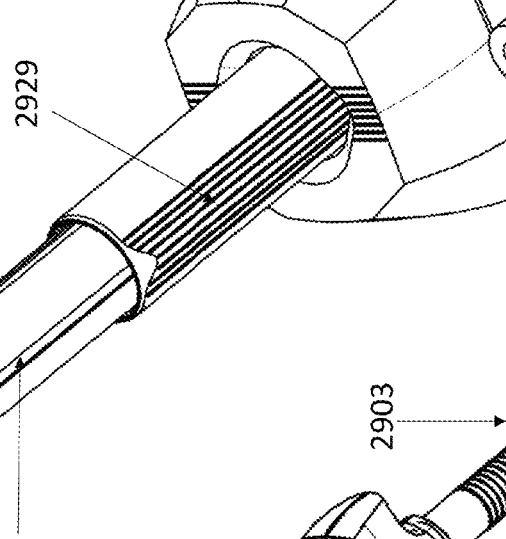
Figure 29D:
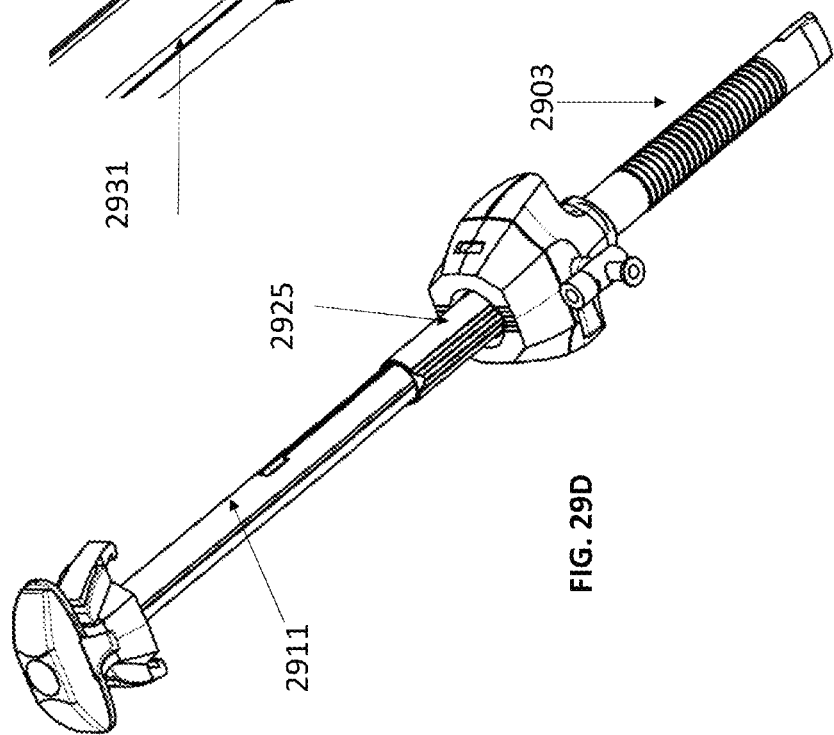

Additionally or alternatively, for example as shown in FIGS. 29D-F, a sleeve 2925 (shown in FIG. 29D and enlarged in FIG. 29E) is positioned between the external cannula and the trocar. Optionally, a proximal portion 2927 of cannula 2903, shown at a cross section in FIG. 29F, comprises a geometry suitable for aligning the sleeve with respect to the cannula, so that trocar 2911 positioned in the sleeve is aligned at a selected alignment with respect to the cannula by the sleeve. In this example, sleeve 2925 comprises one or more elongated protrusions 2929 on the outside surface of the sleeve, and optionally an elongated protrusion in the inner surface of the sleeve (not shown) which can be received within a matching elongated recess 2931 of trocar 2911. Respectively, at least the proximal portion of 2927 comprises, on its inner surface, matching recesses for receiving the elongated protrusions of the sleeve. It is noted that the alignment geometry may comprise other shapes and/or profiles of respective recesses and projections configured on the trocar, sleeve, and/or cannula.

FIGS. 30A-C show a proximally facing cutting element of a trocar, according to some embodiments of the invention.

In some embodiments, a distal portion 3001 of a trocar for example as shown in FIG. 30A comprises one or more proximally facing cutting elements 3003. In some embodiments, cutting element 3003 comprises at least one cutting edge 3009 and/or tip 3011 adapted for cutting and/or piercing and/or puncturing the tissue.

In some embodiments, cutting element 3003 is positioned opposite a distal tip 3005 of anchor 3007. In some embodiments, the cutting element remains static during operation, while anchor 3007 is advanced distally until interacting with cutting edge 3009 which cuts and/or pierces the tissue from a substantially opposite direction to the penetration direction of the anchor, i.e. in a substantially distal to proximal direction. A potential advantage of contacting the tissue to be penetrated from opposite sides of the tissue may include producing a more accurately located wound. Another potential advantage may include faster penetration of the anchor.

In some embodiments, distal trocar portion 3001 comprises a recess 3017 in which anchor 3007 is received. In some embodiments, cutting element 3003 is configured within recess 3017, for example extending from a distal end of the recess in the proximal direction towards the anchor. Optionally, cutting element 3003 is at least partially circular in profile, and defines a volume in which at least a portion of the length of anchor 3007 is received.

In some embodiments, a depth of the penetration point of the tissue is determined by a relative distance 3015 between proximally facing surface 3013 of distal portion 3001, on which the fascia abuts against, and cutting edge 3009 of cutting element 3003.

The cross section shown in FIG. 30B illustrates an interface between cutting edge 3009 of the cutting element, and anchor 3007. FIG. 30C illustrates distal tip 3011 of the anchor approaching cutting edge 3009.

In some embodiments, an interface between cutting edge 3009 and anchor 3007 produces a scissor like effect, as anchor 3007 glides against cutting edge 3009, cutting the tissue in between. Additionally or alternatively, a punch type or pin hole type wound is formed by the interaction between anchor 3007 and edge 3009. Alternatively, a wound is created edge 3009 alone. Alternatively, a wound is created by anchor 3007 alone.

Alternatively, element 3003 is not a cutting element, and does not comprise a cutting edge. Optionally, element 3003 is positioned at least in part in the advancing path of anchor 3007, to interact with the anchor when the anchor penetrates the tissue. Optionally, element 3003 receives anchor 3007 within it, at least in part.

A potential advantage of utilizing a proximally facing cutting element during tissue penetration may include reducing a risk of damaging the tissue, which may occur when a distally facing cutting element is used and is unintentionally advanced into the tissue.

FIGS. 31A-E illustrate an exemplary anchor deployment procedure in which proximally facing cutting elements interact with the anchors to penetrate the tissue, according to some embodiments of the invention.

In some embodiments, for example as shown in FIG. 31A, a distal trocar portion 3101 is advanced into fascia 3103, and is positioned such that fascia 3103 leans against proximally facing shaft wall 3105. One or more proximally facing cutting elements 3113 are now positioned within and/or under fascia 3103, with a cutting edge 3115 and/or tip facing a proximal direction.

At this stage, as shown for example in FIG. 31B, anchors 3107 are advanced towards the fascia, optionally forming a tissue fold 3109 for example as described herein. In some embodiments, the tissue fold is created within a recess 3111 of the trocar portion 3101, and tissue is crimped between an anchor 3107 and a wall of recess 3111.

In some embodiments, the extent of tissue fold 3109 increases, for example as shown in FIG. 31C, as the anchors are pushed further distally causing more tissue to fit between the anchor and the recess.

In some embodiments, for example as shown in FIG. 31D, anchors 3107 are advanced to contact and/or pass cutting edge 3115 of cutting element 3113, penetrating fascia 3103. In some embodiments, anchors 3107 are advanced past the cutting elements 3113. Optionally, anchors 3107 are advanced past a distal end 3117 of the trocar. Alternatively, the anchors do not advance beyond a distal end of the trocar. Optionally, an anchor is at least partially received within the lumen of cutting element 3113.

In FIG. 31E, fascia 3103 has returned back to a substantially flat state, while the anchor thrusting elements 3119 have been pulled in a proximal direction away from the tissue, leaving anchors 3107 deployed in the tissue.

In some embodiments, for example when the trocar is retracted from the tissue, damage to the tissue which may be caused by moving cutting elements 3113 in a proximal direction is reduced or prevented by delivering the distal trocar portion 3101 through the external cannula (not shown in this figure), which acts as a barrier between the cutting elements and the tissue during retraction.

It is noted that the tissue folding effect is not a necessary condition for the functioning of the proximally facing cutting elements, and is simply presented in this illustration as an additional option which may or may not be obtained during use of the trocar assembly.

Figure 32A:
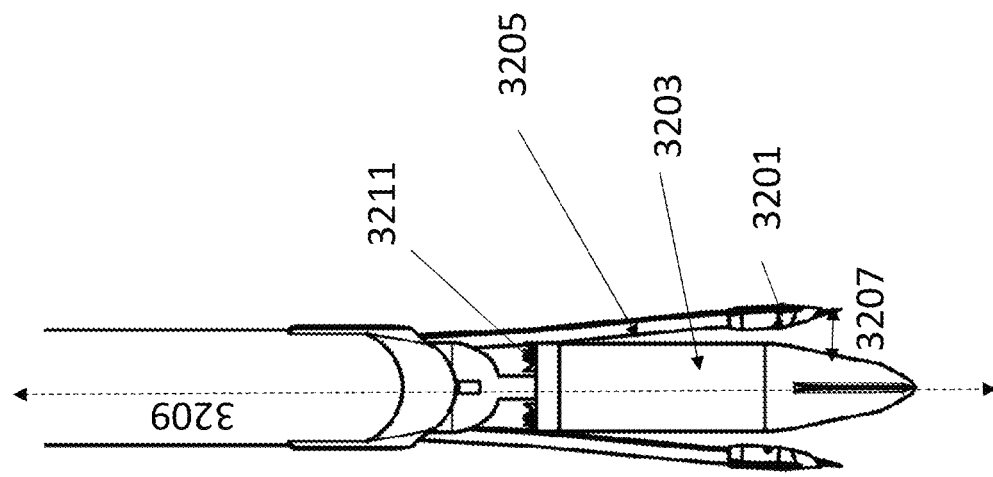
Figure 32B:
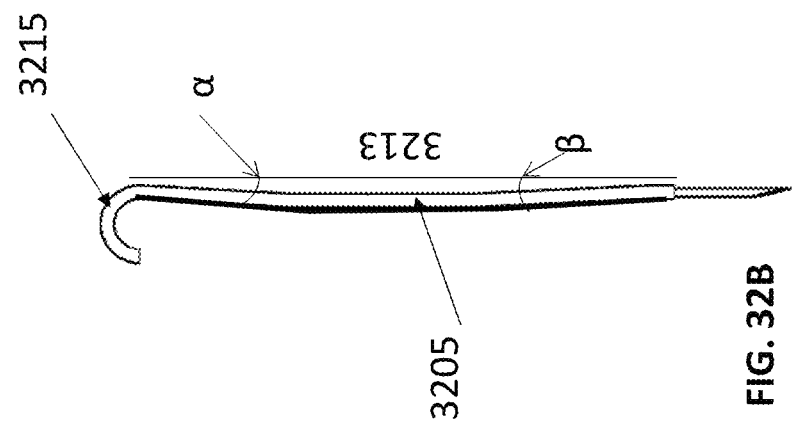

FIGS. 32A-B illustrate an anchor thrusting element configured for deploying an anchor at a distance from the trocar shaft, according to some embodiments of the invention.

In some embodiments, in which deploying an anchor 3201 at a distance 3207 relative to the trocar shaft 3203 is desirable, an anchor thrusting element 3205 is forced at one or more locations along its length to produce an angle relative to the longitudinal axis of the trocar 3209, thereby deploying the anchor radially further away from the trocar. Optionally, as the anchor thrusting element is advanced distally to push the anchor, one or more components of the trocar force the anchor thrusting element to move away from axis 3209. For example, thrusting element 3205 may be forced aside as it encounters shaft wall 3211 during advancement. Additionally or alternatively, thrusting element 3205 may be forced aside due to resistive force of the tissue.

Additionally or alternatively, an arched anchor thrusting element is used, for example as shown in FIG. 32B. Optionally, thrusting element 3205 is formed with one or more curves, as indicated by angles α and β, shown relative to a straight line 3213. Optionally, angle α and/or angle β range between, for example, 5-20 degrees, such as 7 degrees, 10 degrees, 15 degrees or intermediate, larger or smaller numbers. In some embodiments, element 3205 comprises a curved proximal head 3215, for example having circular or semi circular profile. Optionally, by applying force at various locations along head 3215, for example by teeth of the sliding element, such as described herein, a distal portion of element 3205 is directed offset from a linear path, positioning element 3205 at an angle relative to the trocar shaft.

An exemplary structure and mechanism providing for advancing anchor thrusting element 3205 at an angle relative to longitudinal axis 3209 is shown in FIGS. 32C and D. FIG. 32C shows elements 3205 prior to advancement, according to some embodiments of the invention. FIG. 32D shows elements 3205 in an advanced position for deploying the anchors in the tissue. When referring to the advancement path of the anchor thrusting element, point 3230 marks an axially movable location which is geometrically defined by the sliding element 3221 which travels distally within the trocar shaft. Point 3232 marks a static location defined between the trocar shaft and external cannula 3225, through which the anchor thrusting element is forced to pass. In some embodiments, both points 3230 and 3232 are located along an axis parallel to longitudinal axis 3209 of the trocar. When the arched thrusting element 3205 is advanced by the sliding element, point 3230 moves closer to point 3232, and element 3205 is forced to extend radially outward with respect to axis 3209.

FIGS. 33A-E show a trocar comprising a set of rotatable wings configured for extending radially outward with respect to the trocar shaft, according to some embodiments of the invention. In some embodiments, a trocar comprises one or more elements configured for defining and/or limiting a penetration area of the anchors into the tissue. In some embodiments, a trocar comprises one or more elements suitable for increasing a surface area that the fascia is stretched against, potentially facilitating penetration of the anchors through the stretched tissue.

In FIGS. 33A-E, a set of wings configured for performing one or both the above described functions are shown. FIG. 33A shows a set of wings 3301 rotatably attached to a shaft portion 3303, in a closed configuration. In some embodiments, the wings are configured distally to the narrow portion 3305, so that when the anchors (not shown in this figure) are advanced distally, they are guided to pass through a frame 3311 defined by the wings when in an open configuration.

FIG. 33B shows a cross section of the shaft portion 3303 onto which the wings are assembled. In some embodiments, a wing 3301 comprises a substantial U-shape, so that when rotated to an open configuration, for example as shown in FIG. 33C and in the cross section of FIG. 33D, wing 3301 defines the frame 3311, optionally in the form of a circular area, between wing 3301 and a wall 3307 of a recess 3309 of shaft portion 3303.

In some embodiments, for example as shown in FIG. 33C, wings 3301 are rotated between the open and close configurations by a rod 3313. Optionally, rotation of rod 3313 is actuated, for example during anchor deployment, by transferring the linear movement of the sliding element and handle to rotational movement. This may be obtained, for example, by a separate proximally extending element (e.g. a lever, an additional rod) operatively coupled to rod 3313 and to the handle and/or sliding element.

FIGS. 34A-E show a trocar comprising an axially extendible and compressible structure, according to some embodiments of the invention.

Figure 34E:
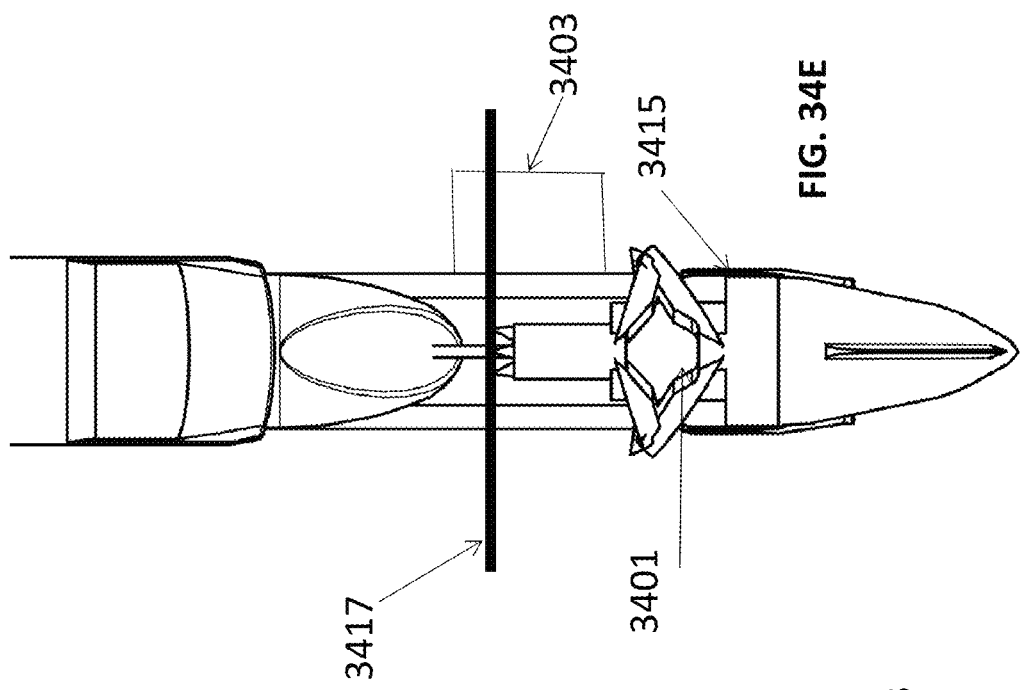
Figure 34C:
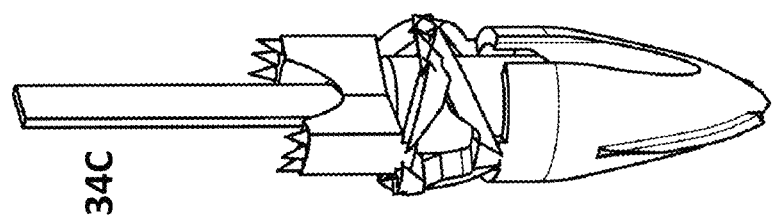
Figure 34D:
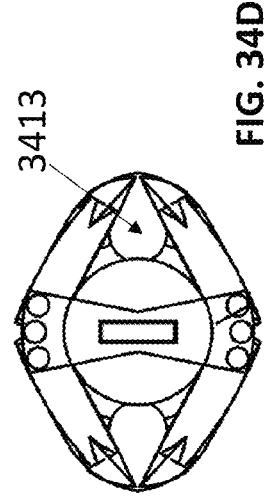
Figure 34A:
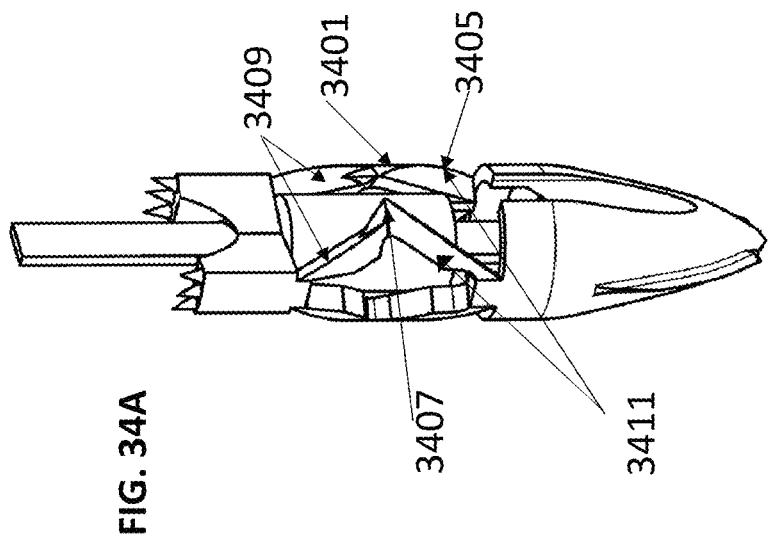
Figure 34B:
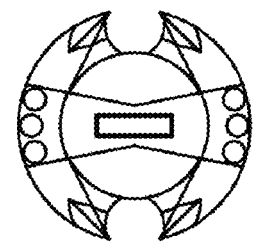

In some embodiments, an axially extendible and/or compressible structure 3401 is configured distally to narrow portion 3403 of the trocar. In some embodiments, structure 3401 is formed of a plurality of arms 3405, such as 4, 2, 6 or intermediate, larger or smaller number of arms, coupled by one or more movable joints 3407. In some embodiments, axially opposing sets of arms such as 3409 and 3411 can be approximated towards each other, for example as shown in FIG. 34C and in the cross section of FIG. 34D, to produce a frame 3413 in between the approximated arms through which an anchor 3415 can be passed through, for example as shown in FIG. 34E.

In some embodiments, structure 3401 is compressed by the fascia 3417, for example when the trocar is slightly pulled in a proximal direction following initial insertion of the trocar.

In some embodiments, a diameter of a substantially circular frame defined between the arms ranges between, for example, 3-8 mm, such as 4 mm, 6 mm, 7 mm or intermediate, larger or smaller diameters. In some embodiments, the defined frame is not circular but comprises other shapes, such as squared, trapezoidal, or arbitrary.

In some embodiments, tissue trapped in the frame is slightly stretched between the arms. A potential advantage of slightly stretching the tissue may include facilitating penetration of the tissue and ensuring that the anchor is fully inserted into the tissue, for example that the anchor has crossed the complete thickness of the fascia layer.

Figure 35B:
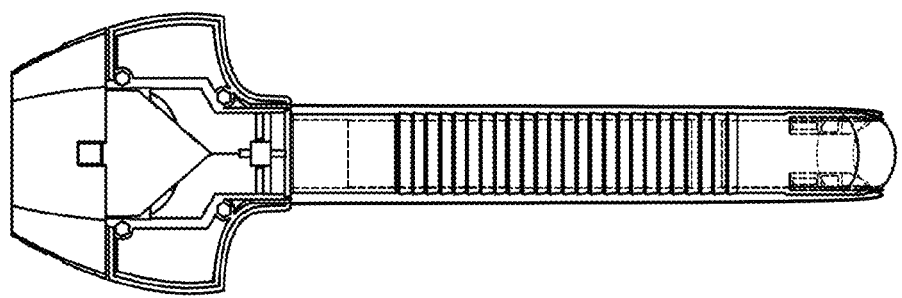
Figure 35A:
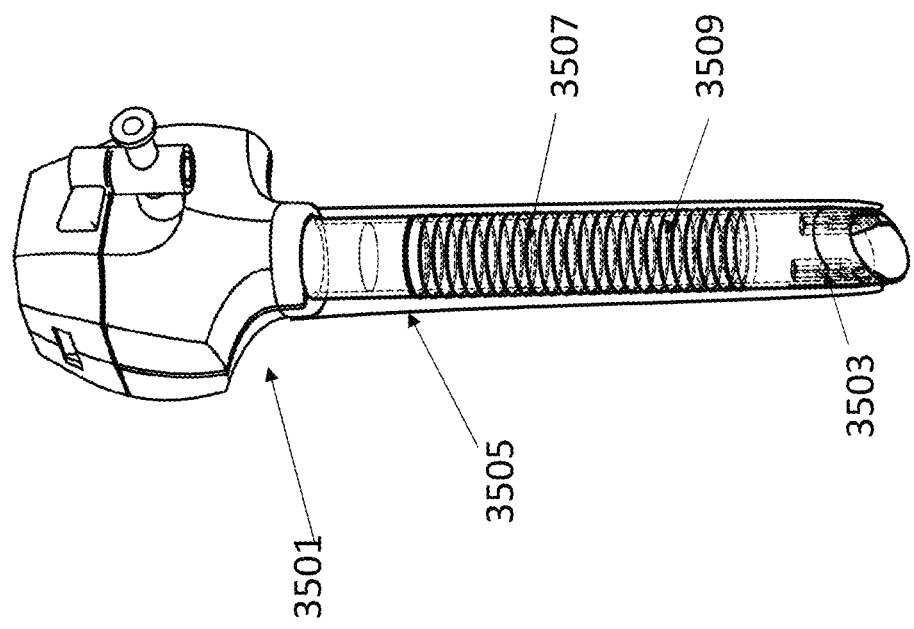

FIGS. 35A-B are an isometric and cross sectional views, respectively, of an external cannula 3501, according to some embodiments of the invention.

In some embodiments, one or more anchors 3503 in which sutures 3505 are threaded are removably attached to an inner wall of cannula 3501, for example at a distal portion of the hollow cylindrical shaft of the cannula 3507. In some embodiments, a coupling between the anchors and the cannula is structured to allow advancement of the anchors along a defined track. Such track is provided, for example, by an elongated trapezoidal recess which defines a dovetail coupling, for example as described hereinabove.

In some embodiments, hollow cylindrical shaft 3507 comprises a textured surface, for example comprising bumps or protrusions, such as ring shaped protrusions 3509, which increase the contact area between the external walls of the cannula and the tissue. A potential advantage of the textured surface may include increasing resistance of the cannula against unintentional pull-out of the cannula from the tissue. The textured surface may be effective to reduce slippage of the cannula when in tissue and/or obtain a stronger hold of the cannula in the surrounding tissue.

In some embodiments, for example as shown in FIGS. 35C-E, cannula 3507 comprises one or more reels 3515 of sutures, such as shown in FIG. 35D. Optionally, the sutures are rolled-up in a proximal portion of the cannula, on reels horizontally positioned for example on both sides of the cannula head. In some embodiments, reels 3515 comprise a mechanism for providing automatic pull-back of the sutures, for example during anchor deployment. Optionally, the mechanism comprises the use of one or more clocksprings 3517, for example as shown in FIG. 35E, operatively coupled to the reel. A potential advantage of storing the sutures on reels 3515 may include reducing the risk of the suture being entangled and/or curled up, reducing the risk of sutures interrupting the passing of tools through the cannula, reducing the risk of sutures interrupting the advancement of the trocar through the cannula, and/or other advantages. In some embodiments, for example at the end of the procedure when the external cannula is removed from the tissue, the suture ends are released from the cannula and can be tied together by a user.

FIGS. 36A-B are photos of an in vivo experiment performed in a porcine model using a trocar and external cannula assembly, according to some embodiments of the invention. FIG. 36A shows, from an abdominal direction, a distal portion 3601 of a trocar advanced through the fascia and peritoneum 3603. In some embodiments, a distal shaft portion 3605 is shaped to create a tissue folding effect, for example as described hereinabove. In FIG. 36B, anchors 3607 are advanced into the tissue by anchor thrusting elements 3609. Optionally, as shown for example in FIG. 36B, the anchors are deployed at a slight angle from a longitudinal axis of the trocar, extending radially away. A similar configuration of the trocar and external cannula assembly used in this experiment is shown, for example, on FIG. 25A.

FIGS. 37A-F are photos of another in vivo experiment performed in a porcine model, using a trocar and external cannula assembly, according to some embodiments of the invention. In FIG. 37A, a distal tip 3701 of the trocar 3713 (pointed to in FIG. 37D, to distinguish from the external cannula) is pulled in a proximal direction following initial insertion of the trocar into the abdominal cavity to cause the proximally facing surface to abut against fascia 3703 (optionally including the thin peritoneum layer). Optionally, one or more projections of the proximally facing surface slightly prick the fascia, to obtain a stronger hold. In FIG. 37B, anchors 3705 are advanced distally with the aid of anchor thrusting elements 3707. Optionally, the tissue is stretched by the anchors in a distal direction before the actual penetration. In FIG. 37C, the anchor thrusting elements 3707 are retracted proximally back into the shaft of the trocar, leaving anchors 3705 (along with sutures 3709 that are threaded through the anchors) in the lumen of the abdomen, adjacent (e.g. directly underneath) the fascia. In FIG. 37D, the assembly comprising the trocar 3713 and external cannula 3711 is advanced distally to prepare for retraction of the trocar 3713 from the external cannula 3711. At this stage, anchors 3705 are pulled proximally to lean against the fascia 3703, such as by the automatic suture pull back mechanism further described herein and/or manually by the user. In FIG. 37E, trocar 3713 has been retracted from external cannula 3711 and the cannula remains positioned in the tissue, providing a port for delivery of surgical tools such as a laparoscope. In FIG. 37F, cannula 3711 is removed from the tissue, and sutures 3709 are tied together to close the wound, for example by the user such as a physician.

FIGS. 38A-C are an exemplary configuration of a trocar 3801 received within an external cannula 3803, wherein the trocar shaft does not comprise a narrow portion, according to some embodiments of the invention. In the exemplary configuration shown in the figures, a distal portion of trocar 3801 is advanced through fascia layer 3805. Optionally, for example as shown in FIG. 28B, an expanding element 3807 coupled to and/or integrated with a shaft of trocar 3801 is expanded, for example expanded radially outwards relative to the trocar shaft, so that fascia 3805 abuts against the expanded element. In some embodiments, for example as shown in FIG. 38C, anchor thrusting elements 3809 are advanced, for example out of the trocar shaft and optionally radially outward with respect to the trocar shaft to engage anchors 3811 and deliver the anchors to the tissue. Optionally, anchors 3811 are removably attached to external cannula 3803 prior to their engagement by the anchor thrusting elements, for example the anchors are coupled to an inner wall of the cannula at a distal end of the cannula.

In some embodiments, a kit comprising trocar 3801 and one or more external cannulas 3803 is provided.

It is expected that during the life of a patent maturing from this application many relevant trocar and/or wound closure devices will be developed and the scope of the term trocar and/or wound closure device is intended to include all such new technologies a priori.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A trocar adapted for insertion through a fascia layer of an abdominal wall, comprising:
    a proximal end configured for handling by a user;
    a distal end configured to be inserted into said abdominal wall; and
    a shaft extending in between said proximal end and distal end;
wherein said shaft comprises:
a narrow portion proximal to said distal end, said narrow portion defining at least one recess shaped and sized to receive fascia tissue;
    a widening configured proximally to said narrow portion, said widening comprising a geometry defining a distally facing surface; wherein said trocar is configured to advance at least one anchor into the tissue; and wherein a shaft portion configured distally to said narrow portion comprises a plurality of fixed projections having tips in the proximal diction, said projections long enough to hold said fascia tissue during advancement of said at least one anchor into said fascia tissue.

2. The trocar according to claim 1, wherein said recess ends, at a distal end of said recess, with a generally proximally facing surface of said shaft, said surface comprising a tissue engaging geometry configured to restrict movement of fascia tissue received within said recess away from said recess.

3. The trocar according to claim 2, wherein said generally proximally facing surface comprises an expandable structure which when expanded increases contact with fascia tissue facing the abdomen, said expandable structure comprising a closed configuration for insertion or removal of the trocar, and an open configuration for preventing the trocar from being pulled in a proximal direction away from the fascia.

4. The trocar according to claim 3, wherein said expandable structure defines at least one frame through which an anchor is passed to be deployed in tissue.

5. The trocar according to claim 1, wherein a length of said narrow portion is between 0.5-30 mm, and wherein said recess is initiated at a distance of at least 0.5 mm from a longitudinal axis of said shaft, said recess having a depth of at least 1 mm in the radial direction.

6. The trocar according to claim 1, wherein a summed cross sectional area of said narrow portion is at least 50% less than a summed cross sectional area of at least one of a shaft portion configured proximally to said narrow portion, and a shaft portion configured distally to said narrow portion.

7. The trocar according to claim 1, wherein said narrow portion is long enough so as to receive a fascia tissue portion having a thickness of at least 0.5 mm.

8. The trocar according to claim 1, wherein said shaft is cylindrical, and said at least one recess is circumferential.

9. The trocar according to claim 8, wherein a diameter of a shaft portion configured directly below said narrow portion is larger than a diameter of said wound so that tissue that has been stretched by said shaft portion during insertion springs back around said narrow portion when said narrow portion is positioned in fascia.

10. The trocar according to claim 1, wherein said projections are configured to prick the fascia to increase resistance.

11. The trocar according to claim 1, wherein a shaft portion configured proximally to said narrow portion comprises a conical profile or a hemispherical profile increasing in diameter in a proximal direction, to provide increasing resistance during insertion of said trocar into the abdominal wall.

12. The trocar according to claim 1, wherein said trocar comprises at least one anchor thruster advanceable distally relative to said shaft, and an anchor advancing assembly.

13. The trocar according to claim 12, wherein said anchor advancing assembly comprises a slider operably coupled to a handle for manipulation by a user, said slider comprising a geometry suitable to force said at least one anchor thruster distally when advanced within said shaft of said trocar.

14. The trocar according to claim 13, wherein said trocar comprises a spring and said at least one anchor thruster is automatically retracted by said spring.

15. The trocar according to claim 13, wherein said trocar is configured to provide wound closure by further comprising at least one suture anchor and a suture coupled to said anchor.

16. The trocar according to claim 15, wherein said trocar comprises at least one proximally facing cutting element positioned distally to said narrow portion, said at least one cutting element shaped to interact with said anchor to assist said anchor to penetrate the tissue.

17. The trocar according to claim 13, wherein said slider comprises a sliding element.

18. The trocar according to claim 12, wherein said anchor thruster comprises an anchor thrusting element.

19. The trocar according to claim 12, wherein said anchor thruster comprises an elongate form.

20. The trocar according to claim 1, further comprising one or more needles for deploying a suture in a tissue, said one or more needles positioned within a trocar shaft portion configured distally to the narrow portion, with a sharp end of the needles facing a proximal direction.

21. The trocar according to claim 1, wherein a shaft portion of said trocar configured distally to said narrow portion comprises one or more recesses in addition to said at least one recesses defined by said narrow portion, said one or more recesses shaped to form a tissue fold when said trocar is inserted into the tissue, said tissue fold formed over said one or more recesses and having a substantial upside down U-shape for increasing a distance between suture anchors deployed over opposing sides of said tissue fold.

22. A kit for use in a laparoscopic procedure, said kit comprising:
    a trocar according to claim 1;
    an external cannula sized to receive said trocar, said cannula comprising at least one anchor removably coupled to a wall of said cannula,
wherein said trocar comprises an anchor advancing assembly, said assembly comprising at least one anchor thruster configured for extending externally to a shaft of said trocar to engage said at least one anchor of said external cannula and advance said at least one anchor into tissue.

23. The kit according to claim 22, wherein said anchor thruster is shaped as a rod, and wherein a distal surface of said rod engages a proximal surface of said at least one anchor.

24. The kit according to claim 22, wherein said kit further comprises a plurality of external cannulas in which said trocar can be inserted.

25. The kit according to claim 22, wherein a coupling between said at least one anchor and said external cannula is structured not to interfere with insertion of said trocar into said cannula and advancement of said trocar to a ready to use position, in which said at least one anchor thruster is located substantially above said at least one anchor.

26. The kit according to claim 22, wherein said anchor advancing assembly is contained within said shaft of said trocar until operated to advance said at least one anchor into the tissue.

27. The kit according to claim 26, wherein said anchor advancing assembly further comprises a slider operably coupled to a handle for manipulation by a user, said slider comprising a geometry suitable to force said at least one anchor thruster distally when advanced within said shaft of said trocar.

28. The kit according to claim 22, wherein said anchor comprises a hollow body shaped and sized to receive said at least one anchor thruster, and at least one surface adapted for abutting against the fascia in a deployed position of said at least one anchor.

29. The kit according to claim 22, wherein an inner wall of said external cannula comprises at least one elongate recess in which at least a portion of said at least one anchor is received, said at least one elongate recess defining a path for advancement of said at least one anchor towards the tissue; said at least one elongate recess shaped to define a dovetail coupling between said at least one anchor and said external cannula.

30. The kit according to claim 22, further comprising a sleeve shaped and positioned to enable at least one of insertion of said trocar into said external cannula and retraction of said trocar from said external cannula.

31. The kit according to claim 30, wherein said sleeve is shaped and sized to seal a lumen between said trocar and said external cannula for preventing gas from escaping from within an abdomen in which said trocar and said external cannula are positioned.

32. The kit according to claim 22, wherein an inner wall of said external cannula comprises at least one elongate recess in which at least a portion of said at least one anchor is received, said at least one elongate recess defining a path for advancement of said at least one anchor towards the tissue; said at least one elongate recess shaped to define a dovetail coupling between said at least one anchor and said external cannula.

33. The trocar according to claim 1, wherein said distal tip is sharp enough for incising said abdominal wall to form said wound.

34. The trocar according to claim 33, wherein said distal tip comprises an integrated blade.

35. The trocar according to claim 1, wherein a distance between a proximal facing surface of said shaft defined by said narrow portion and a distal end of said trocar is smaller than 4 times a diameter of said shaft.

36. The trocar according to claim 1, wherein a distal end of said recess is spaced apart from said distal end of said trocar a maximal distance of less than 50 mm.

37. The trocar according to claim 1, wherein said trocar is configured to advance at least two anchors into the tissue; and wherein a shaft portion configured distally to said narrow portion defines a step relative to said narrow portion, said step shaped to cause fascia tissue to be crimped over said step so as to increase a distance between said at least two anchors when deployed in said tissue.

38. The trocar according to claim 37, further comprising a widening distally to said step, said widening defining surface positioned to counter act said at least two anchors to assist said anchors in penetrating the tissue.

39. The trocar according to claim 1, wherein said widening comprises a smooth, rounded profile suitable to be advanced through said insertion wound.

40. A method for providing sensible feedback to a user for positioning a trocar adapted for insertion into an abdominal wall, said trocar comprising a shaft formed with a narrow portion in proximity to a distal end of said trocar; comprising:

inserting said trocar through an abdominal wall;
pulling said trocar in a proximal direction until encountering resistance formed by a surface of said shaft defined distally to said narrow portion that abuts against a fascia layer of said abdominal walls, said surface comprising a plurality of fixed projections having tips in the proximal direction;
positioning said trocar so that said fascia layer enters one or more recesses defined by said narrow portion; and
advancing at least one anchor into said fascia layer while said projections hold said fascia.

41. The method according to claim 40, wherein said method further comprises deploying anchors at said fascia layer.

42. The method according to claim 40, wherein said inserting comprises encountering resistance formed by a distally facing surface configured proximally to said narrow portion, said resistance indicating to said user to cease advancing of said trocar into the tissue.

43. The method according to claim 40, wherein said inserting forms a wound having a first cross sectional area in said fascia layer; wherein during said positioning said fascia closes in over said narrow portion to define a wound having a second cross sectional area smaller than said first cross sectional area.

44. A trocar adapted for insertion through a fascia layer of an abdominal wall, comprising:

a proximal end configured for handling by a user;
a distal end configured to be inserted into said abdominal wall; and
a shaft extending in between said proximal end and distal end;
wherein said shaft comprises:
a narrow portion proximal to said distal end, said narrow portion defining at least one recess shaped and sized to receive fascia tissue;
a widening configured proximally to said narrow portion, said widening comprising a geometry defining a distally facing surface;
wherein a shaft portion configured distally to said narrow portion comprises one or more recesses in addition to said at least one recess defined by said narrow portion, said one or more recesses shaped to form a tissue fold when said trocar is inserted into the tissue, said tissue fold formed over said one or more recesses and having a substantial upside down U-shape for increasing a distance between suture anchors deployed over opposing sides of said tissue fold.

45. The trocar according to claim 44, wherein said at least one recess ends, at a distal end of said at least one recess, with a generally proximally facing surface of said shaft, said surface comprising a tissue engaging geometry configured to restrict movement of fascia tissue received within said at least one recess away from said at least one recess.

46. The trocar according to claim 45, wherein said tissue engaging geometry of said generally proximally facing surface comprises one or more projections, said one or more projections having tips in a direction of said fascia configured to prick the fascia to increase resistance.

47. The trocar according to claim 45, wherein said generally proximally facing surface comprises an expandable structure which when expanded increases contact with fascia tissue facing the abdomen, said expandable structure comprising a closed configuration for insertion or removal of the trocar, and an open configuration for preventing the trocar from being pulled in a proximal direction away from the fascia.

48. The trocar according to claim 47, wherein said expandable structure defines at least one frame through which an anchor is passed to be deployed in tissue.

49. The trocar according to claim 44, wherein a length of said narrow portion is between 0.5-30 mm, and wherein said at least one recess is initiated at a distance of at least 0.5 mm from a longitudinal axis of said shaft, said at least one recess having a depth of at least 1 mm in the radial direction.

50. The trocar according to claim 44, wherein a summed cross sectional area of said narrow portion is at least 50% less than a summed cross sectional area of at least one of a shaft portion configured proximally to said narrow portion, and a shaft portion configured distally to said narrow portion.

51. The trocar according to claim 44, wherein said narrow portion is long enough so as to receive a fascia tissue portion having a thickness of at least 0.5 mm.

52. The trocar according to claim 44, wherein said shaft is cylindrical, and said at least one recess is circumferential.

53. The trocar according to claim 52, wherein a diameter of a shaft portion configured directly below said narrow portion is larger than a diameter of said wound so that tissue that has been stretched by said shaft portion during insertion springs back around said narrow portion when said narrow portion is positioned in fascia.

54. The trocar according to claim 44, wherein a shaft portion configured proximally to said narrow portion comprises a conical profile or a hemispherical profile increasing in diameter in a proximal direction, to provide increasing resistance during insertion of said trocar into the abdominal wall.

55. The trocar according to claim 44, wherein said trocar comprises at least one anchor thruster advanceable distally relative to said shaft, and an anchor advancing assembly.

56. The trocar according to claim 55 wherein said anchor advancing assembly comprises a slider operably coupled to a handle for manipulation by a user, said slider comprising a geometry suitable to force said at least one anchor thruster distally when advanced within said shaft of said trocar.

57. The trocar according to claim 56, wherein said slider comprises a sliding element.

58. The trocar according to claim 55, wherein said trocar comprises a spring and said at least one anchor thruster is automatically retracted by said spring.

59. The trocar according to claim 55, wherein said trocar is configured to provide wound closure by further comprising at least one suture anchor and a suture coupled to said anchor.

60. The trocar according to claim 59, wherein said trocar comprises at least one proximally facing cutting element positioned distally to said narrow portion, said at least one cutting element shaped to interact with said anchor to assist said anchor to penetrate the tissue.

61. The trocar according to claim 55, wherein said anchor thruster comprises an anchor thrusting element.

62. The trocar according to claim 55, wherein said anchor thruster comprises an elongate form.

63. The trocar according to claim 44 further comprising one or more needles for deploying a suture in a tissue, said one or more needles positioned within a trocar shaft portion configured distally to the narrow portion, with a sharp end of the needles facing a proximal direction.

64. A kit for use in a laparoscopic procedure, said kit comprising:
 a trocar according to claim 44;
 an external cannula sized to receive said trocar, said cannula comprising at least one anchor removably coupled to a wall of said cannula,
wherein said trocar comprises an anchor advancing assembly, said assembly comprising at least one anchor thruster configured for extending externally to a shaft of said trocar to engage said at least one anchor of said external cannula and advance said at least one anchor into tissue.

65. The kit according to claim 64, wherein said anchor thruster is shaped as a rod, and wherein a distal surface of said rod engages a proximal surface of said at least one anchor.

66. The kit according to claim 64, wherein said kit further comprises a plurality of external cannulas in which said trocar can be inserted.

67. The kit according to claim 64, wherein a coupling between said at least one anchor and said external cannula is structured not to interfere with insertion of said trocar into said cannula and advancement of said trocar to a ready to use position, in which said at least one anchor thruster is located substantially above said at least one anchor.

68. The kit according to claim 64, wherein said anchor advancing assembly is contained within said shaft of said trocar until operated to advance said at least one anchor into the tissue.

69. The kit according to claim 68, wherein said anchor advancing assembly further comprises a slider operably coupled to a handle for manipulation by a user, said slider comprising a geometry suitable to force said at least one anchor thruster distally when advanced within said shaft of said trocar.

70. The kit according to claim 64, wherein said anchor comprises a hollow body shaped and sized to receive said at least one anchor thruster, and at least one surface adapted for abutting against the fascia in a deployed position of said at least one anchor.

71. The kit according to claim 64, further comprising a sleeve shaped and positioned to enable at least one of insertion of said trocar into said external cannula and retraction of said trocar from said external cannula.

72. The kit according to claim 71, wherein said sleeve is shaped and sized to seal a lumen between said trocar and said external cannula for preventing gas from escaping from within an abdomen in which said trocar and said external cannula are positioned.

73. The trocar according to claim 44, wherein said distal tip is sharp enough for incising said abdominal wall to form said wound.

74. The trocar according to claim 73, wherein said distal tip comprises an integrated blade.

75. The trocar according to claim 44, wherein a distance between a proximal facing surface of said shaft defined by said narrow portion and a distal end of said trocar is smaller than 4 times a diameter of said shaft.

76. The trocar according to claim 44, wherein a distal end of said at least one recess is spaced apart from said distal end of said trocar a maximal distance of less than 50 mm.

77. The trocar according to claim 44, wherein said trocar is configured to advance at least two anchors into the tissue; and
wherein a shaft portion configured distally to said narrow portion defines a step relative to said narrow portion, said step shaped to cause fascia tissue to be crimped over said step so as to increase a distance between said at least two anchors when deployed in said tissue.

78. The trocar according to claim 77, further comprising a widening distally to said step, said widening defining surface positioned to counter act said at least two anchors to assist said anchors in penetrating the tissue.

79. The trocar according to claim 44, wherein said trocar is configured to advance at least one anchor into the tissue; wherein a shaft portion configured distally to said narrow portion comprises a plurality of fixed projections having tips in the proximal direction, said projections long enough to hold said fascia tissue during advancement of said at least one anchor into said fascia tissue.

80. The trocar according to claim 44, wherein said widening comprises a smooth, rounded profile suitable to be advanced through said insertion wound.

81. A trocar adapted for insertion through a fascia layer of an abdominal wall, comprising:
a proximal end configured for handling by a user;
a distal end comprising an integrated blade configured to form an insertion wound in said abdominal wall; and
a shaft extending in between said proximal end and distal end;
wherein said shaft comprises:
a narrow portion proximal to said distal end, said narrow portion defining at least one recess shaped and sized to receive fascia tissue; and
a widening configured proximally to said narrow portion, said widening comprising a geometry defining a distally facing surface;
wherein said at least one recess ends, at a distal end of said recess, with a generally proximally facing surface of said shaft, said proximally facing surface comprising a tissue engaging geometry configured to restrict movement of fascia tissue received within said recess away from said recess; and wherein said generally proximally facing surface comprises an expandable structure which when expanded increases contact with fascia tissue facing the abdomen, said expandable structure comprising a closed configuration for insertion or removal of the trocar, and an open configuration for preventing the trocar from being pulled in a proximal direction away from the fascia.

82. The trocar according to claim 81, wherein said tissue engaging geometry of said generally proximally facing surface comprises one or more projections, said one or more projections having tips in a direction of said fascia are configured to prick the fascia to increase resistance.

83. The trocar according to claim 82, wherein said projections are configured to prick the fascia to increase resistance.

84. The trocar according to claim 81, wherein a length of said narrow portion is between 0.5-30 mm, and wherein said recess is initiated at a distance of at least 0.5 mm from a longitudinal axis of said shaft, said recess having a depth of at least 1 mm in the radial direction.

85. The trocar according to claim 81, wherein a summed cross sectional area of said narrow portion is at least 50% less than a summed cross sectional area of at least one of a shaft portion configured proximally to said narrow portion, and a shaft portion configured distally to said narrow portion.

86. The trocar according to claim 81, wherein said narrow portion is long enough so as to receive a fascia tissue portion having a thickness of at least 0.5 mm.

87. The trocar according to claim 86, wherein a diameter of a shaft portion configured directly below said narrow portion is larger than a diameter of said wound so that tissue that has been stretched by said shaft portion during insertion springs back around said narrow portion when said narrow portion is positioned in fascia.

88. The trocar according to claim 81, wherein said shaft is cylindrical, and said at least one recess is circumferential.

89. The trocar according to claim 81, wherein a shaft portion configured proximally to said narrow portion comprises a conical profile or a hemispherical profile increasing in diameter in a proximal direction, to provide increasing resistance during insertion of said trocar into the abdominal wall.

90. The trocar according to claim 81, wherein said trocar comprises at least one anchor thruster advanceable distally relative to said shaft, and an anchor advancing assembly.

91. The trocar according to claim 90, wherein said anchor advancing assembly comprises a slider operably coupled to a handle for manipulation by a user, said slider comprising a geometry suitable to force said at least one anchor thruster distally when advanced within said shaft of said trocar.

92. The trocar according to claim 91, wherein said trocar comprises a spring and said at least one anchor thruster is automatically retracted by said spring.

93. The trocar according to claim 91, wherein said trocar is configured to provide wound closure by further comprising at least one suture anchor and a suture coupled to said anchor.

94. The trocar according to claim 90, wherein said anchor thruster comprises an anchor thrusting element.

95. The trocar according to claim 90, wherein said anchor thruster comprises an elongate form.

96. The trocar according to claim 90, wherein said slider comprises a sliding element.

97. The trocar according to claim 81, wherein said trocar comprises at least one proximally facing cutting element positioned distally to said narrow portion, said at least one cutting element shaped to interact with said anchor to assist said anchor to penetrate the tissue.

98. The trocar according to claim 97, further comprising one or more needles for deploying a suture in a tissue, said one or more needles positioned within a trocar shaft portion configured distally to the narrow portion, with a sharp end of the needles facing a proximal direction.

99. The trocar according to claim 81, wherein said expandable structure defines at least one frame through which an anchor is passed to be deployed in tissue.

100. The trocar according to claim 81, wherein a shaft portion of said trocar configured distally to said narrow portion comprises one or more recesses in addition to said at least one recess defined by said narrow portion, said one or more recesses shaped to form a tissue fold when said trocar is inserted into the tissue, said tissue fold formed over said one or more recesses and having a substantial upside down U-shape for increasing a distance between suture anchors deployed over opposing sides of said tissue fold.

101. A kit for use in a laparoscopic procedure, said kit comprising:
 a trocar according to claim 81;
 an external cannula sized to receive said trocar, said cannula comprising at least one anchor removably coupled to a wall of said cannula,
wherein said trocar comprises an anchor advancing assembly, said assembly comprising at least one anchor thruster configured for extending externally to a shaft of said trocar to engage said at least one anchor of said external cannula and advance said at least one anchor into tissue.

102. The kit according to claim 101, wherein said anchor thruster is shaped as a rod, and wherein a distal surface of said rod engages a proximal surface of said at least one anchor.

103. The kit according to claim 102, further comprising a sleeve shaped and positioned to enable at least one of insertion of said trocar into said external cannula and retraction of said trocar from said external cannula.

104. The kit according to claim 103, wherein said sleeve is shaped and sized to seal a lumen between said trocar and said external cannula for preventing gas from escaping from within an abdomen in which said trocar and said external cannula are positioned.

105. The kit according to claim 101, wherein said kit further comprises a plurality of external cannulas in which said trocar can be inserted.

106. The kit according to claim 101, wherein said anchor advancing assembly is contained within said shaft of said trocar until operated to advance said at least one anchor into the tissue.

107. The kit according to claim 101, wherein a coupling between said at least one anchor and said external cannula is structured not to interfere with insertion of said trocar into said cannula and advancement of said trocar to a ready to use position, in which said at least one anchor thruster is located substantially above said at least one anchor.

108. The kit according to claim 107, wherein said anchor advancing assembly further comprises a slider operably coupled to a handle for manipulation by a user, said slider comprising a geometry suitable to force said at least one anchor thruster distally when advanced within said shaft of said trocar.

109. The kit according to claim 101, wherein said anchor comprises a hollow body shaped and sized to receive said at least one anchor thruster, and at least one surface adapted for abutting against the fascia in a deployed position of said at least one anchor.

110. The kit according to claim 101, wherein an inner wall of said external cannula comprises at least one elongate recess in which at least a portion of said at least one anchor is received, said at least one elongate recess defining a path for advancement of said at least one anchor towards the tissue; said at least one elongate recess shaped to define a dovetail coupling between said at least one anchor and said external cannula.

111. The trocar according to claim 81, wherein said distal tip is sharp enough for incising said abdominal wall to form said wound.

112. The trocar according to claim 81, wherein distance between a proximal facing surface of said shaft defined by said narrow portion and a distal end of said trocar is smaller than 4 times a diameter of said shaft.

113. The trocar according to claim 81, wherein a distal end of said recess is spaced apart from said distal end of said trocar a maximal distance of less than 50 mm.

114. The trocar according to claim 81, wherein said trocar is configured to advance at least two anchors into the tissue; and
 wherein a shaft portion configured distally to said narrow portion defines a step relative to said narrow portion, said step shaped to cause fascia tissue to be crimped over said step so as to increase a distance between said at least two anchors when deployed in said tissue.

115. The trocar according to claim 114, further comprising a widening distally to said step, said widening defining surface positioned to counter act said at least two anchors to assist said anchors in penetrating the tissue.

116. The trocar according to claim 81, wherein said trocar is configured to advance at least one anchor into the tissue; wherein a shaft portion configured distally to said narrow portion comprises a plurality of fixed projections having tips in the proximal direction, said projections long enough to hold said fascia tissue during advancement of said at least one anchor into said fascia tissue.

117. The trocar according to claim 81, wherein said widening comprises a smooth, rounded profile suitable to be advanced through said insertion wound.

\* \* \* \* \*